US006312921B1

(12) United States Patent
Jacobs et al.

(10) Patent No.: US 6,312,921 B1
(45) Date of Patent: Nov. 6, 2001

(54) SECRETED PROTEINS AND POLYNUCLEOTIDES ENCODING THEM

(75) Inventors: Kenneth Jacobs, Newton; John M. McCoy, Reading; Edward R. LaVallie, Harvard; Lisa A. Racie, Acton, all of MA (US); Cheryl Evans, Germantown, MD (US); David Merberg, Acton, MA (US); Sha Mi, Belmont, MA (US); Maurice Treacy, Chestnut Hill, MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 09/175,928

(22) Filed: Oct. 20, 1998

Related U.S. Application Data

(63) Continuation-in-part of application No. 09/080,478, filed on May 18, 1998, now abandoned, which is a continuation-in-part of application No. 08/976,110, filed on Nov. 21, 1997, now abandoned, which is a continuation-in-part of application No. 08/686,878, filed on Jul. 26, 1996, now Pat. No. 5,708,157, which is a continuation-in-part of application No. 08/702,081, filed on Aug. 23, 1996, now abandoned, which is a continuation-in-part of application No. 08/721,489, filed on Sep. 27, 1996, now Pat. No. 5,786,465, which is a continuation-in-part of application No. 08/721,924, filed on Sep. 27, 1996, now Pat. No. 5,969,125, which is a continuation-in-part of application No. 08/686,878, filed on Jul. 26, 1996, now Pat. No. 5,708,157.

(51) Int. Cl.[7] .............................. C12P 21/06; C12N 1/20; C12N 15/00; C07H 21/02; C07H 21/04

(52) U.S. Cl. .................. 435/69.1; 435/252.3; 435/320.1; 536/23.1; 536/23.5; 536/24.3; 530/350

(58) Field of Search ................... 435/69.1, 252.3, 435/320.1; 536/23.5, 23.1, 24.3; 530/350

(56) References Cited

U.S. PATENT DOCUMENTS

| 4,267,195 | 5/1981 | Bourdeau et al. | 426/2 |
| 5,708,157 | 1/1998 | Jacobs et al. | 536/23.5 |

FOREIGN PATENT DOCUMENTS

| 0606734A1 | 7/1994 | (EP) . |
| WO 97/08189 | 3/1997 | (WO) . |
| WO 98/45435 | 10/1998 | (WO) . |

OTHER PUBLICATIONS

Hillier et al., GenBank Accession No: AA426511 (EST Database); Oct. 16, 1997.*

Pauley et al. GenBank Accession No: AC000064 (GenEmbl Database); Nov. 13, 1996.*

Evans et al. GenBank Accession No: BO6164 (EST Database); Jul. 13, 1996.*

Marra et al, GenBank Accession No. AA497966, Jul. 1, 1997.

Grafham, D., GenBank Accession No. AL031177, Mar. 30, 1997.

Jackson et al, Cloning of a novel surface antigen from the insect stages of Trypanosoma brucei by expression in COS cells. JBC 268:1894–1900, Jan. 25, 1993.

Jacobs et al, A genetic selection for isolating cDNAs encoding secreted proteins. Gene 198:289–296, Oct. 1, 1997.

* cited by examiner

*Primary Examiner*—Karen Cochrane Carlson
*Assistant Examiner*—Rita Mitra
(74) *Attorney, Agent, or Firm*—Lahive & Cockfield, LLP; Amy E. Mandragouras; Debra J. Milasincic

(57) ABSTRACT

Novel polynucleotides and the proteins encoded thereby are disclosed.

16 Claims, 15 Drawing Sheets

AJ172 Expression in Human Term Placenta: *in situ* hybridization

AJ 172-Transfected COS Cells Fused Together

FIG. 6
AJ172-Mediated Fusion of COS to HELA Cells
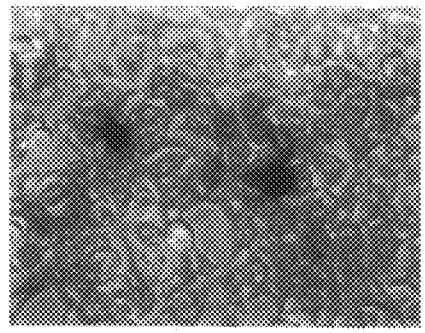
COS: AJ172 reverse orientation
+ HELA: PSGL-Fc
 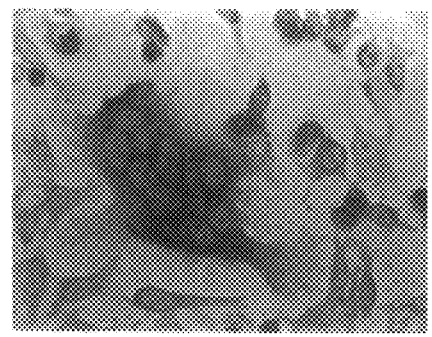
COS: AJ172
+HELA: PSGL-Fc AJ172-Expressing COS Cells Fuse to Liposomes Containing
A Green Fluorescent Protien Expression Plasmid Unfused COS cell    AJ172-fused COS cell

*AJ172 does not require a protein receptor to mediate membrane fusion*

FIG. 11
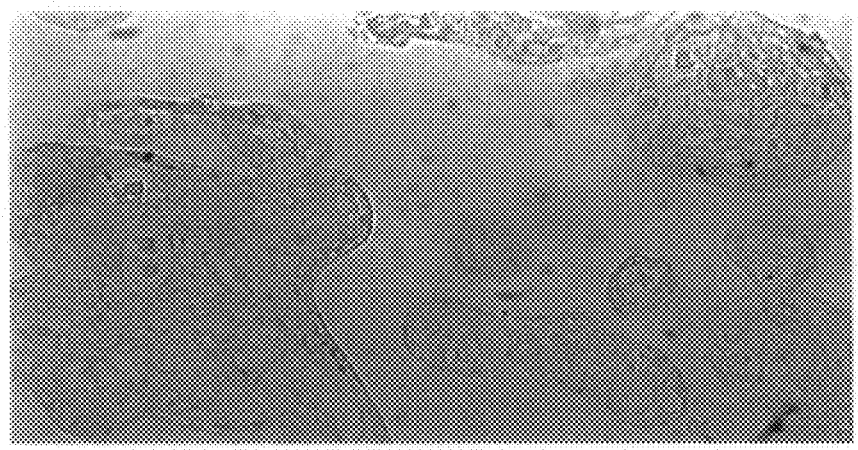
sense probe
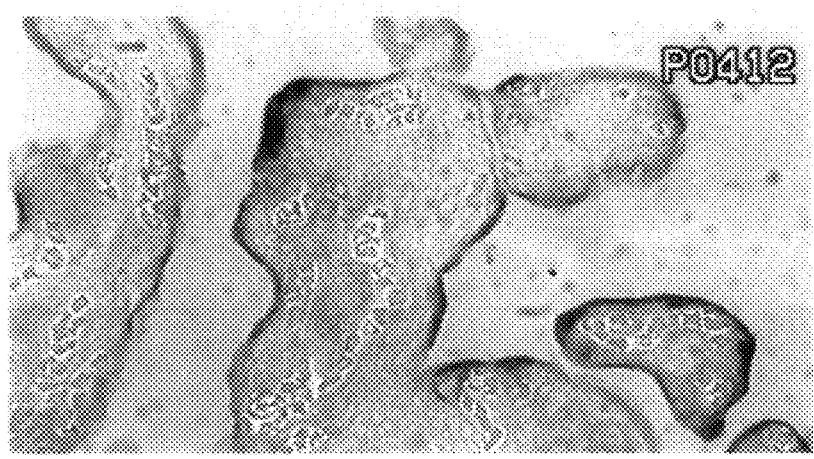
anti-sense probe

FIG. 14
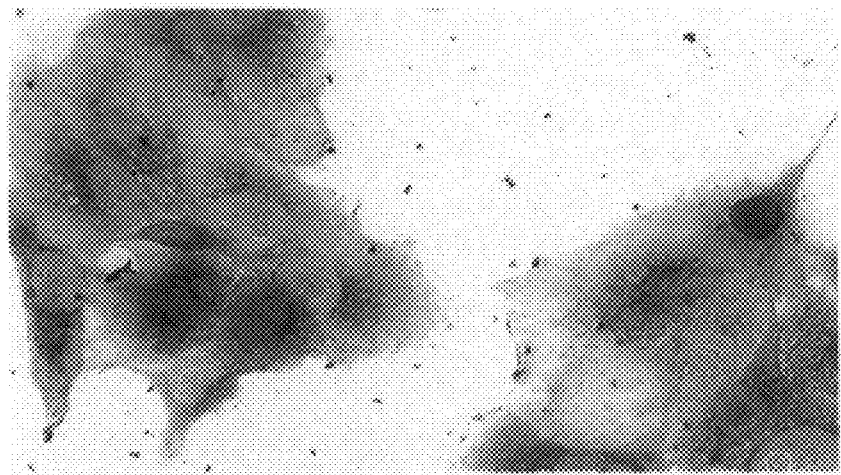
-forskolin
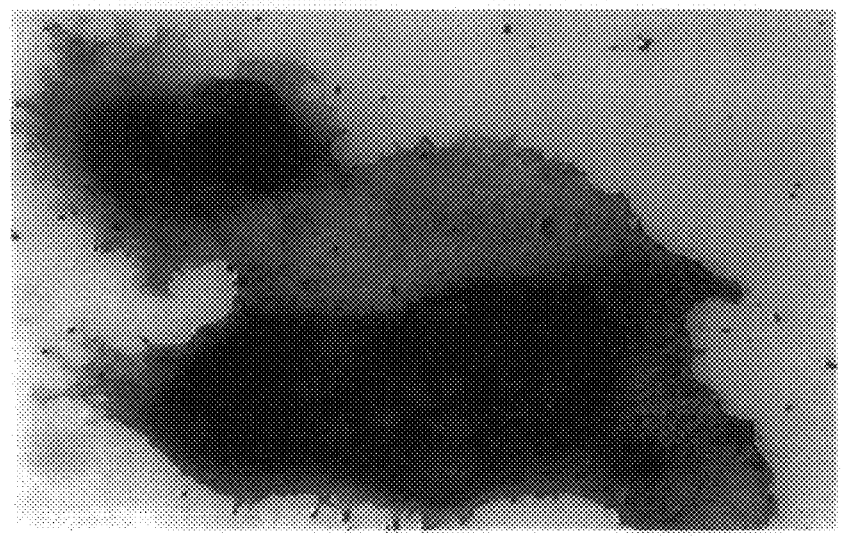
+forskolin

SEQUENCE LISTING

<160> NUMBER OF SEQ ID NOS: 62

<210> SEQ ID NO 1
<211> LENGTH: 2166
<212> TYPE: DNA
<213> ORGANISM: Homo sapiens

<400> SEQUENCE: 1

```
ggcaagctac tggcacctgc tgctctcaac taacctccac acaatggtgt tcgcattttg      60
gaaggtcttt ctgatcctaa gctgccttgc aggtcaggtt agtgtggtgc aagtgaccat     120
cccagacggt ttcgtgaacg tgactgttgg atctaatgtc actctcatct gcatctacac     180
caccactgtg gcctcccgag aacagctttc catccagtgg tctttcttcc ataagaagga     240
gatggagcca atttctattt acttttctca aggtggacaa gctgtagcca tcgggcaatt     300
taaagatcga attacagggt ccaacgatcc aggtaatgca tctatcacta tctcgcatat     360
gcagccagca gacagtggaa tttacatctg cgatgttaac aaccccccag actttctcgg     420
ccaaaaccaa ggcatcctca acgtcagtgt gttagtgaaa ccttctaagc ccctttgtag     480
cgttcaagga agaccagaaa ctggccacac tatttccctt tcctgtctct ctgcgcttgg     540
aacaccttcc cctgtgtact actggcataa acttgaggga agagacatcg tgccagtgaa     600
agaaaacttc aacccaacca ccgggatttt ggtcattgga aatctgacaa attttgaaca     660
aggttattac cagtgtactg ccatcaacag acttggcaat agttcctgcg aaatcgatct     720
cacttcttca catccagaag ttggaatcat tgttggggcc ttgattggta gcctggtagg     780
tgccgccatc atcatctctg ttgtgtgctt cgcaaggaat aaggcaaaag caaaggcaaa     840
agaaagaaat tctaagacca tcgcggaact tgagccaatg acaaagataa acccaagggg     900
agaaagcgaa gcaatgccaa gagaagacgc tacccaacta gaagtaactc taccatcttc     960
cattcatgag actggccctg ataccatcca agaaccagac tatgagccaa agcctactca    1020
ggagcctgcc ccagagcctg ccccaggatc agagcctatg gcagtgcctg accttgacat    1080
cgagctggag ctggagccaa aaacgcagtc ggaattggag ccagagccag agccagagcc    1140
agagtcgagg cctgggggttg tagttgagcc cttaagtgaa gatgaaaagg gagtggttaa    1200
ggcataggct ggtggcctaa gtacagcatt aatcattaag gaacccatta ctgccatttg    1260
gaattcaaat aacctaacca acctccacct cctccttcca ttttgaccaa ccttcttcta    1320
acaaggtgct cattcctact atgaatccag aataaacacg ccaagataac agctaaatca    1380
gcaagggttc ctgtattacc aatatagaat actaacaatt ttactaacac gtaagcataa    1440
caaatgacag ggcaagtgat ttctaactta gttgagtttt gcaacagtac ctgtgttgtt    1500
atttcagaaa atattatttc tctcttttta actactcttt ttttttattt tagacagagt    1560
cgcttgagcc caggaggtgg aggttgcagt gggccgagat tgtgccactg cactccaacc    1620
tgggtgacag agtgagattc catctgaaaa acaaaaacaa aaacagaaaa caaacaaaca    1680
aaaaacaaaa aatccccaca actttgtcaa ataatgtaca ggcaaacact ttcaaatata    1740
atttccttca gtgaatacaa aatgttgata tcataggtga tgtacaattt agttttgaat    1800
gagttattat gttatcactg tgtctgatgt tatctacttt gaaaggcagt ccagaaaagt    1860
```

-continued

```
gttctaagtg aactcttaag atctatttta gataatttca actaattaaa taacctgttt     1920
tactgcctgt acattccaca ttaataaagc gataccaatc ttatatgaat gctaatatta     1980
ctaaaatgca ctgatatcac ttcttcttcc cctgttgaaa agctttctca tgatcatatt     2040
tcacccacat ctcaccttga agaaacttac aggtagactt acctttcac ttgtggaatt      2100 aatcatattt aaatcttact ttaaggctca ataataata ctcataaaaa aaaaaaaaa       2160 aaaaaa                                                                 2166
```

<210> SEQ ID NO 2
<211> LENGTH: 387
<212> TYPE: PRT
<213> ORGANISM: Homo sapiens

<400> SEQUENCE: 2

```
Met Val Phe Ala Phe Trp Lys Val Phe Leu Ile Leu Ser Cys Leu Ala
  1               5                  10                  15

Gly Gln Val Ser Val Gln Val Thr Ile Pro Asp Gly Phe Val Asn
             20                  25                  30

Val Thr Val Gly Ser Asn Val Thr Leu Ile Cys Ile Tyr Thr Thr Thr
         35                  40                  45

Val Ala Ser Arg Glu Gln Leu Ser Ile Gln Trp Ser Phe Phe His Lys
     50                  55                  60

Lys Glu Met Glu Pro Ile Ser Ile Tyr Phe Ser Gln Gly Gln Ala
 65                  70                  75                  80

Val Ala Ile Gly Gln Phe Lys Asp Arg Ile Thr Gly Ser Asn Asp Pro
                 85                  90                  95

Gly Asn Ala Ser Ile Thr Ile Ser His Met Gln Pro Ala Asp Ser Gly
                100                 105                 110

Ile Tyr Ile Cys Asp Val Asn Asn Pro Pro Asp Phe Leu Gly Gln Asn
            115                 120                 125

Gln Gly Ile Leu Asn Val Ser Val Leu Val Lys Pro Ser Lys Pro Leu
        130                 135                 140

Cys Ser Val Gln Gly Arg Pro Glu Thr Gly His Thr Ile Ser Leu Ser
145                 150                 155                 160

Cys Leu Ser Ala Leu Gly Thr Pro Ser Pro Val Tyr Tyr Trp His Lys
                165                 170                 175

Leu Glu Gly Arg Asp Ile Val Pro Val Lys Glu Asn Phe Asn Pro Thr
            180                 185                 190

Thr Gly Ile Leu Val Ile Gly Asn Leu Thr Asn Phe Glu Gln Gly Tyr
        195                 200                 205

Tyr Gln Cys Thr Ala Ile Asn Arg Leu Gly Asn Ser Ser Cys Glu Ile
    210                 215                 220

Asp Leu Thr Ser Ser His Pro Glu Val Gly Ile Ile Val Gly Ala Leu
225                 230                 235                 240

Ile Gly Ser Leu Val Gly Ala Ala Ile Ile Ser Val Val Cys Phe
                245                 250                 255

Ala Arg Asn Lys Ala Lys Ala Lys Ala Lys Glu Arg Asn Ser Lys Thr
            260                 265                 270

Ile Ala Glu Leu Glu Pro Met Thr Lys Ile Asn Pro Arg Gly Glu Ser
        275                 280                 285

Glu Ala Met Pro Arg Glu Asp Ala Thr Gln Leu Glu Val Thr Leu Pro
    290                 295                 300

Ser Ser Ile His Glu Thr Gly Pro Asp Thr Ile Gln Glu Pro Asp Tyr
```

```
                305                 310                 315                 320
Glu Pro Lys Pro Thr Gln Glu Pro Ala Pro Glu Ala Pro Gly Ser
                    325                 330                 335
Glu Pro Met Ala Val Pro Asp Leu Asp Ile Glu Leu Glu Leu Glu Pro
            340                 345                 350
Glu Thr Gln Ser Glu Leu Glu Pro Glu Pro Pro Glu Pro Glu Ser
        355                 360                 365
Glu Pro Gly Val Val Val Glu Pro Leu Ser Glu Asp Glu Lys Gly Val
    370                 375                 380
Val Lys Ala
385

<210> SEQ ID NO 3
<211> LENGTH: 2946
<212> TYPE: DNA
<213> ORGANISM: Homo sapiens

<400> SEQUENCE: 3
tcgggctgcc ttatcgccaa gctccttcag gagaacaaag aacaggccat taccctggag      60
aagactggca actgatttta cccacaagcc caaacctcag ggatttcagt atctactagt     120
ctgggtagat actttcacgg gttgggcaga ggccttcccc tgtaggacag aaaaggccca     180
agaggtaata aaggcactag ttcatgaaat aattcccaga ttcggacttc cccgaggctt     240
acagagtgac aatagccctg ctttccaggc cacagtaacc cagggagtat cccaggcgtt     300
aggtatacga tatcacttac actgcgcctg aaggccacag tcctcaggga aggtcgagaa     360
aatgaatgaa acactcaaag gacatctaaa aaagcaaacc caggaaaccc acctcacatg     420
gcctgctctg ttgcctatag ccttaaaaag aatctgcaac tttccccaaa aagcaggact     480
tagcccatac gaaatgctgt atggaagccc cttcataacc aatgaccttg tgcttgaccc     540
aagacagcca acttagttgc agacatcacc tccttagcca aatatcaaca agttcttaaa     600
acattacaag gaacctatcc ctgagaagag ggaaaagaac tattccaccc ttgtgacatg     660
gtattagtca agtcccttcc ctctaattcc ccatccctag atacatcctg ggaaggaccc     720
tacccagtca ttttatctac cccaactgcg gttaaagtgg ctggagtgga gtcttggata     780
catcacactt gagtcaaatc ctggatactg ccaaaggaac ctgaaaatcc aggagacaac     840
gctagctatt cctgtgaacc tctagaggat ttgcgcctgc tcttcaaaca acaaccagga     900
ggaaagtaac taaaatcata aatccccatg gccctcccct atcatatttt tctctttact     960
gttcttttac cctctttcac tctcactgca cccctccat gccgctgtat gaccagtagc    1020
tccccttacc aagagtttct atggagaatg cagcgtcccg gaaatattga tgccccatcg    1080
tataggagtc tttctaaggg aaccccacc ttcactgccc acacccatat gccccgcaac    1140
tgctatcact ctgccactct tgcatgcat gcaaatactc attattggac aggaaaaatg    1200
attaatccta gttgtcctgg aggacttgga gtcactgtct gttggactta cttcacccaa    1260
actggtatgt ctgatggggg tggagttcaa gatcaggcaa gagaaaaaca tgtaaaagaa    1320
gtaatctccc aactcacccg ggtacatggc acctctagcc cctacaaagg actagatctc    1380
tcaaaactac atgaaacct ccgtacccat actcgcctgg taagcctatt taataccacc    1440
ctcactgggc tccatgaggt ctcggcccaa aaccctacta actgttggat atgcctcccc    1500
ctgaacttca ggccatatgt ttcaatccct gtacctgaac aatggaacaa cttcagcaca    1560
gaaataaaca ccacttccgt tttagtagga cctcttgttt ccaatctgga ataacccat    1620
```

-continued

```
acctcaaacc tcacctgtgt aaaatttagc aatactacat acacaaccaa ctcccaatgc    1680
atcaggtggg taactcctcc cacacaaata gtctgcctac cctcaggaat attttttgtc    1740
tgtggtacct cagcctatcg ttgtttgaat ggctcttcag aatctatgtg cttcctctca    1800
ttcttagtgc cccctatgac catctacact gaacaagatt tatacaatta tgtcatatct    1860
aagccccgca acaaaagagt acccattctt ccttttgtta taggagcagg agtgctaggt    1920
gcactaggta ctggcattgg cggtatcaca acctctactc agttctacta caaactatct    1980
caagaactaa atggggacat ggaacgggtc gccgactccc tggtcacctt gcaagatcaa    2040
cttaactccc tagcagcagt agtccttcaa aatcgaagag ctttagactt gctaaccgct    2100
gaaagagggg gaacctgttt attttttaggg gaagaatgct gttattatgt taatcaatcc    2160
ggaatcgtca ctgagaaagt taaagaaatt cgagatcgaa tacaacgtag agcagaggag    2220
cttcgaaaca ctggaccctg gggcctcctc agccaatgga tgccctggat tctcccttc     2280 ttaggacctc tagcagctat aatattgcta ctcctctttg gaccctgtat ctttaacctc    2340
cttgttaact ttgtctcttc cagaatcgaa gctgtaaaac tacaaatgga gcccaagatg    2400
cagtccaaga ctaagatcta ccgcagaccc ctggaccggc ctgctagccc acgatctgat    2460
gttaatgaca tcaaaggcac ccctcctgag gaaatctcag ctgcacaacc tctactacgc    2520
cccaattcag caggaagcag ttagagcggt cgtcggccaa cctccccaac agcacttagg    2580
ttttcctgtt gagatggggg actgagagac aggactagct ggatttccta ggctgactaa    2640
gaatccctaa gcctagctgg gaaggtgacc acatccacct ttaaacacgg ggcttgcaac    2700
ttagctcaca cctgaccaat cagagagctc actaaaatgc taattaggca aaaacaggag    2760
gtaaagaaat agccaatcat ctattgcctg agagcacagc aggagggaca atgatcggga    2820
tataaaccca gtcttcgag ccggcaacgg caacccccctt tgggtcccct ccctttgtat    2880
gggagctctg ttttcatgct atttcactct attaaatctt gcaactgcaa aaaaaaaaa    2940 aaaaaa                                                             2946
```

<210> SEQ ID NO 4
<211> LENGTH: 538
<212> TYPE: PRT
<213> ORGANISM: Homo sapiens

<400> SEQUENCE: 4

```
Met Ala Leu Pro Tyr His Ile Phe Leu Phe Thr Val Leu Leu Pro Ser
 1               5                  10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Val Lys Glu Val Ile Ser Gln Leu Thr Arg Val His Gly Thr Ser Ser
```

```
        130                 135                 140
Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Asn Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Ala Val Val Leu Gln Asn Arg Arg
    370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Glu Glu Ile Ser Ala Ala Gln Pro
        515                 520                 525

Leu Leu Arg Pro Asn Ser Ala Gly Ser Ser
    530                 535

<210> SEQ ID NO 5
```

```
<211> LENGTH: 338
<212> TYPE: DNA
<213> ORGANISM: Homo sapiens
<220> FEATURE:
<221> NAME/KEY: unsure
<222> LOCATION: (259)
<220> FEATURE:
<221> NAME/KEY: unsure
<222> LOCATION: (261)
<220> FEATURE:
<221> NAME/KEY: unsure
<222> LOCATION: (282)
<220> FEATURE:
<221> NAME/KEY: unsure
<222> LOCATION: (285)
<220> FEATURE:
<221> NAME/KEY: unsure
<222> LOCATION: (312)
<220> FEATURE:
<221> NAME/KEY: unsure
<222> LOCATION: (334)

<400> SEQUENCE: 5
agcggccgcg ccatccccat caagcagggg atcctgctaa agcggagcgg caagtccctg      60
aacaaggagt ggaagaagaa gtatgtgacg ctctgtgaca acgggctgct cacctatcac     120
cccagcctgc atcttggtgc gctgtctgtg ccctctgcca acagtggagg cagcgaggat     180
gaagaggagt ggcaagggt gtcttggatg tggaaaaaaa tgtgggttgt ggggttgggc     240
tgggttttgg tttcagtana ngaaacacag ccagctggag ancanaactc acggggggttg     300 gtggcttttc anaatcaccc ggctggtggc tganctaa                             338

<210> SEQ ID NO 6
<211> LENGTH: 387
<212> TYPE: DNA
<213> ORGANISM: Homo sapiens
<220> FEATURE:
<221> NAME/KEY: unsure
<222> LOCATION: (30)
<220> FEATURE:
<221> NAME/KEY: unsure
<222> LOCATION: (163)

<400> SEQUENCE: 6
aagtaggcaa gggataataa ccaaagaagn aaatttcatg aagactagac atcataaagc      60
ataattttaa tagtcactca accaagtatt ttttattttt tatggatact ctgaatggca     120
attaaatgtg aaaccccagtt tcttgggcaa gtcaaattst ggnatcacat ccacctaaat     180
taaaatgact agctcgtatt tcccccatct tcaagtttca catcctggtc atcaaaagac     240
tcgacagcaa gacttagaat gmaaaagggt acttgtttat attaatattt tttacttgaa     300
cacgtgtagc ttgcagcagg ttcttgatga atgtgctttg tgtccaaaat gcctccccat     360
tgtacacagg tgtacaccat gcatgca                                         387

<210> SEQ ID NO 7
<211> LENGTH: 67
<212> TYPE: PRT
<213> ORGANISM: Homo sapiens
<220> FEATURE:
<221> NAME/KEY: UNSURE
<222> LOCATION: (26)

<400> SEQUENCE: 7

Met Thr Ser Ser Tyr Phe Pro His Leu Gln Val Ser His Pro Gly His
  1               5                  10                  15

Gln Lys Thr Arg Gln Gln Asp Leu Glu Xaa Lys Arg Val Leu Val Tyr
```

```
            20                  25                  30
Ile Asn Ile Phe Tyr Leu Asn Thr Cys Ser Leu Gln Gln Val Leu Asp
             35                  40                  45

Glu Cys Ala Leu Cys Pro Lys Cys Leu Pro Ile Val His Arg Cys Thr
 50                  55                  60

Pro Cys Met
 65

<210> SEQ ID NO 8
<211> LENGTH: 348
<212> TYPE: DNA
<213> ORGANISM: Homo sapiens
<220> FEATURE:
<221> NAME/KEY: unsure
<222> LOCATION: (59)
<220> FEATURE:
<221> NAME/KEY: unsure
<222> LOCATION: (70)
<220> FEATURE:
<221> NAME/KEY: unsure
<222> LOCATION: (72)
<220> FEATURE:
<221> NAME/KEY: unsure
<222> LOCATION: (87)
<220> FEATURE:
<221> NAME/KEY: unsure
<222> LOCATION: (89)
<220> FEATURE:
<221> NAME/KEY: unsure
<222> LOCATION: (92)
<220> FEATURE:
<221> NAME/KEY: unsure
<222> LOCATION: (94)
<220> FEATURE:
<221> NAME/KEY: unsure
<222> LOCATION: (134)
<220> FEATURE:
<221> NAME/KEY: unsure
<222> LOCATION: (138)
<220> FEATURE:
<221> NAME/KEY: unsure
<222> LOCATION: (202)
<220> FEATURE:
<221> NAME/KEY: unsure
<222> LOCATION: (216)
<220> FEATURE:
<221> NAME/KEY: unsure
<222> LOCATION: (223)
<220> FEATURE:
<221> NAME/KEY: unsure
<222> LOCATION: (303)

<400> SEQUENCE: 8
caaaccctaa accctggcag gaagcatgtc gaggaaggag ttccggcaac tccagaggnt      60
ccgacagaan tntgggctga gcctggntnt cntntccagc aagggtttcg cctgagcccc    120
aagggcatcg ggantggnga ctcacctatg gatgggggcc gggagacag gacacacaga     180 agatgagttt gtgggccagc cntgagcccc gcgccngatt ttngccggcc caagagagcc    240
cgccgcagct tcccccattt tgcagccagc ggagccattc acacaatcac cttctgttaa    300
ttntatctgc aacatcaatt aaattgtttg tagaaactaa aaaaaaaa                 348

<210> SEQ ID NO 9
<211> LENGTH: 3153
<212> TYPE: DNA
<213> ORGANISM: Homo sapiens

<400> SEQUENCE: 9
taatcatgcc tcttggaagt aagttaacgg gcgtgattgt ggaaaatgar aatattacca    60
```

-continued

```
aagaaggtgg cttaktggac atggccaaga agaaaatga cttaaatgca gagcccaatt    120
taaagcagac aattaaagca acagtagara atggcaagaa ggatggcatt gctgttgatc    180
atgttgtagg cctgaataca gaaaaatatg ctgaaactgt cmaacttaag cataaaagaa    240
scccaggtaa agtaaaagac atwtcmattg atgttgaaag aaggaatgaa acagtgagg     300
tagacaccag tgctggaagt ggctctgcac cctctgtttt acaccaaagg aacggacaaa    360
ctgaggatgt ggcaactggg cctaggagag cagaaaagac ttctgttgcc actagtactg    420
aagggaagga caaagatgtc accttaagtc cagtgaaggc tgggcctgcc acaaccactt    480
cttcagaaac aagacaaagt gaggtggctt tgccttgcac cagcattgag gcagatgaag    540
gcctcataat aggaacacat tccagaaata atcctcttca tgttggtgca gaagccagtg    600
aatgcactgt ttttgctgca gctgaaaaag gtggggctgt tgtcacagag ggatttgctg    660
aaagtgaaac cttcctcaca agcactaagg aaggggaaag tggggagtgt gctgtggctg    720
aatctgagga cagagcagca gacctactgg ctgtgcatgc agttaaaatc gaagccaatg    780
taaatagcgt tgtgacagag gaaaaggatg atgctgtaac cagtgcaggc tctgaagaaa    840
aatgtgatgg ttctttaagt agagactcag aaatagttga aggaactatt acttttatta    900
gtgaagttga aagtgatgga gcagttacaa gtgctggaac agagataaga gcaggatcta    960
taagcagtga agaggtggat ggctcccagg gaaatatgat gagaatgggt cccaaaaaag   1020
aaacagaggg cactgtgaca tgtacaggag cagaaggcag aagtgataac tttgtgatct   1080
gctcagtaac tggagcaggg ccccgggagg aacgcatggt tacaggtgca ggtgttgtcc   1140
tgggagataa tgatgcacca ccaggaacaa gtgccagcca agaaggagat ggttctgtga   1200
atgatggtac agaaggtgag agtgcagtca ccagcacggg gataacagaa gatggagagg   1260
ggccagcaag ttgcacaggt tcagaagatw gcakcgaagg ctttgctata agttctgaat   1320
cggaagaaaa tggagagagt gcaatggaca gcacagtggc caaagaaggc actaatgtac   1380
cattagttgc tgctggtcct tgtgatgatg aaggcattgt gactagcaca ggcgcaaaag   1440
aggaagacga ggaaggggag gatgttgtga ctagtactgg aagaggaaat gaaattgggc   1500
atgcttcaac ttgtacaggg ttaggagaag aaagtgaagg ggtcttgatt tgtgaaagtg   1560
cagaagggga cagtcagatt ggtactgtgg tagagcatgt ggaagctgag gctggagctg   1620
ccatcatgaa tgcaaatgaa ataatgttg acagcatgag tggcacagag aaaggaagta   1680
aagacacaga tatctgctcc agtgcmaaag ggattgtaga aagcagtgtg accagtgcag   1740
tctcaggaaa ggatgaagtg acaccagttc caggaggttg tgagggtcct atgactagtg   1800
ctgcatctga tcaaagtgac agtcagctcg aaaagttga agataccact atttccactg   1860
gcctggtcgg gggtagttac gatgttcttg tatctggtga agtcccagaa tgtgaagttg   1920
ctcacacatc accaagtgaa aaagaagatg aggacatcat cacctctgta gaaaatgaag   1980
agtgtgatgg tttcatggca actacagcca gtggtgatat taccaaccag aatagcttag   2040
cagggggtaa aaatcaaggc aaagttttga ttatttccac cagtaccaca aatgattaca   2100
cccctcaggt aagcgcaatt acagatgtgg aaggaggtct ttcagatgct ctgagaactg   2160
aagaaaatat ggaaggtacc agagtaacca cagaagaatt tgaggccccc atgcccagtg   2220
cagtctcagg agatgacagc caactcactg ccagcagaag tgaagagaaa gatgagtgtg   2280
ccatgatttc cacaagcata ggggaagaat tcgaattgcc tatctccagt gcaacaacca   2340
tcaagtgtgc tgaaagtttc agccggttgc tgcagcagtg aagaaaggg ctacaggtcc   2400
```

-continued

```
agtcttgata agcaccgccg actttgaggg gcctatgccc agtgcgcccc cagaagctga    2460
aagtcctctt gcctcaacca gcaaggagga gaaggatgaa tgtgctctca tttccactag    2520
catagcagaa gaatgtgagg cttctgtttc cggtgtagtt gttgaaagtg aaaatgagcg    2580
agctggcaca gtcatggaag aaaaagacgg gagtggcatc atctttacga gctcggtgga    2640
agactgtgag ggcccagtgt ccagtgctgt ccctcaagag gaaggcgacc cctcagtcac    2700
accagcggaa gagatgggtg acaccgccat gatttccaca agcacctctg aagggtgtga    2760
agcagtcatg attggtgctg tcctccagga tgaagatcgg ctcaccatca caagagtaga    2820
agacttgagc gatgctgcca tcatctccac cagcacagca gaatgtatgc caatttccgc    2880
cagcattgac agacatgaag agaatcagct gactgcagac aacccagaag ggaacggtga    2940
cytgtcagcc acagaagtga gcaagcacaa gktccccatg cccagcytaa ttgctgagaa    3000
taactgtcgg tgtcctgggc cagtcagggg aggcaaagaa ctgggtcccg tgttggcagt    3060
gagcaccgag gagggcaca acgggccatc agtccacaag ccctctgcag ggcaaggcca    3120
tcaagtgctg tttgtgcgga aaaaaaaaaa aaa                                3153
```

<210> SEQ ID NO 10
<211> LENGTH: 800
<212> TYPE: PRT
<213> ORGANISM: Homo sapiens
<220> FEATURE:
<221> NAME/KEY: UNSURE
<222> LOCATION: (24)
<220> FEATURE:
<221> NAME/KEY: UNSURE
<222> LOCATION: (73)
<220> FEATURE:
<221> NAME/KEY: UNSURE
<222> LOCATION: (79)
<220> FEATURE:
<221> NAME/KEY: UNSURE
<222> LOCATION: (429)..(430)

<400> SEQUENCE: 10

```
Met Pro Leu Gly Ser Lys Leu Thr Gly Val Ile Val Glu Asn Glu Asn
 1               5                  10                  15

Ile Thr Lys Glu Gly Gly Leu Xaa Asp Met Ala Lys Lys Glu Asn Asp
                20                  25                  30

Leu Asn Ala Glu Pro Asn Leu Lys Gln Thr Ile Lys Ala Thr Val Glu
            35                  40                  45

Asn Gly Lys Lys Asp Gly Ile Ala Val Asp His Val Gly Leu Asn
        50                  55                  60

Thr Glu Lys Tyr Ala Glu Thr Val Xaa Leu Lys His Lys Arg Xaa Pro
 65                  70                  75                  80

Gly Lys Val Lys Asp Ile Ser Ile Asp Val Glu Arg Arg Asn Glu Asn
                85                  90                  95

Ser Glu Val Asp Thr Ser Ala Gly Ser Gly Ser Ala Pro Ser Val Leu
               100                 105                 110

His Gln Arg Asn Gly Gln Thr Glu Asp Val Ala Thr Gly Pro Arg Arg
           115                 120                 125

Ala Glu Lys Thr Ser Val Ala Thr Ser Thr Glu Gly Lys Asp Lys Asp
       130                 135                 140

Val Thr Leu Ser Pro Val Lys Ala Gly Pro Ala Thr Thr Ser Ser
145                 150                 155                 160

Glu Thr Arg Gln Ser Glu Val Ala Leu Pro Cys Thr Ser Ile Glu Ala
               165                 170                 175
```

-continued

```
Asp Glu Gly Leu Ile Ile Gly Thr His Ser Arg Asn Asn Pro Leu His
            180                 185                 190
Val Gly Ala Glu Ala Ser Glu Cys Thr Val Phe Ala Ala Glu Lys
        195                 200                 205
Gly Gly Ala Val Val Thr Glu Gly Phe Ala Glu Ser Glu Thr Phe Leu
        210                 215                 220
Thr Ser Thr Lys Glu Gly Glu Ser Gly Glu Cys Ala Val Ala Glu Ser
225                 230                 235                 240
Glu Asp Arg Ala Ala Asp Leu Leu Ala Val His Ala Val Lys Ile Glu
                245                 250                 255
Ala Asn Val Asn Ser Val Val Thr Glu Glu Lys Asp Asp Ala Val Thr
            260                 265                 270
Ser Ala Gly Ser Glu Glu Lys Cys Asp Gly Ser Leu Ser Arg Asp Ser
        275                 280                 285
Glu Ile Val Glu Gly Thr Ile Thr Phe Ile Ser Glu Val Glu Ser Asp
        290                 295                 300
Gly Ala Val Thr Ser Ala Gly Thr Glu Ile Arg Ala Gly Ser Ile Ser
305                 310                 315                 320
Ser Glu Glu Val Asp Gly Ser Gln Gly Asn Met Met Arg Met Gly Pro
                325                 330                 335
Lys Lys Glu Thr Glu Gly Thr Val Thr Cys Thr Gly Ala Glu Gly Arg
            340                 345                 350
Ser Asp Asn Phe Val Ile Cys Ser Val Thr Gly Ala Gly Pro Arg Glu
        355                 360                 365
Glu Arg Met Val Thr Gly Ala Gly Val Val Leu Gly Asp Asn Asp Ala
        370                 375                 380
Pro Pro Gly Thr Ser Ala Ser Gln Glu Gly Asp Gly Ser Val Asn Asp
385                 390                 395                 400
Gly Thr Glu Gly Glu Ser Ala Val Thr Ser Thr Gly Ile Thr Glu Asp
                405                 410                 415
Gly Glu Gly Pro Ala Ser Cys Thr Gly Ser Glu Asp Xaa Xaa Glu Gly
            420                 425                 430
Phe Ala Ile Ser Ser Glu Ser Glu Glu Asn Gly Glu Ser Ala Met Asp
        435                 440                 445
Ser Thr Val Ala Lys Glu Gly Thr Asn Val Pro Leu Val Ala Ala Gly
    450                 455                 460
Pro Cys Asp Asp Glu Gly Ile Val Thr Ser Thr Gly Ala Lys Glu Glu
465                 470                 475                 480
Asp Glu Glu Gly Glu Asp Val Val Thr Ser Thr Gly Arg Gly Asn Glu
                485                 490                 495
Ile Gly His Ala Ser Thr Cys Thr Gly Leu Gly Glu Glu Ser Glu Gly
            500                 505                 510
Val Leu Ile Cys Glu Ser Ala Glu Gly Asp Ser Gln Ile Gly Thr Val
        515                 520                 525
Val Glu His Val Glu Ala Glu Ala Gly Ala Ile Met Asn Ala Asn
        530                 535                 540
Glu Asn Asn Val Asp Ser Met Ser Gly Thr Glu Lys Gly Ser Lys Asp
545                 550                 555                 560
Thr Asp Ile Cys Ser Ser Ala Lys Gly Ile Val Glu Ser Ser Val Thr
                565                 570                 575
Ser Ala Val Ser Gly Lys Asp Glu Val Thr Pro Val Pro Gly Gly Cys
            580                 585                 590
Glu Gly Pro Met Thr Ser Ala Ala Ser Asp Gln Ser Asp Ser Gln Leu
```

|       |       |       |       |       |       |       |       |       |       |
|-------|-------|-------|-------|-------|-------|-------|-------|-------|-------|
|       |       |       | 595   |       |       | 600   |       |       | 605   |

Glu Lys Val Glu Asp Thr Thr Ile Ser Thr Gly Leu Val Gly Gly Ser
610                 615                 620

Tyr Asp Val Leu Val Ser Gly Glu Val Pro Glu Cys Glu Val Ala His
625                 630                 635                 640

Thr Ser Pro Ser Glu Lys Glu Asp Glu Asp Ile Ile Thr Ser Val Glu
            645                 650                 655

Asn Glu Glu Cys Asp Gly Phe Met Ala Thr Ala Ser Gly Asp Ile
                660                 665                 670

Thr Asn Gln Asn Ser Leu Ala Gly Gly Lys Asn Gln Gly Lys Val Leu
            675                 680                 685

Ile Ile Ser Thr Ser Thr Thr Asn Asp Tyr Thr Pro Gln Val Ser Ala
690                 695                 700

Ile Thr Asp Val Glu Gly Gly Leu Ser Asp Ala Leu Arg Thr Glu Glu
705                 710                 715                 720

Asn Met Glu Gly Thr Arg Val Thr Thr Glu Glu Phe Glu Ala Pro Met
                725                 730                 735

Pro Ser Ala Val Ser Gly Asp Asp Ser Gln Leu Thr Ala Ser Arg Ser
                740                 745                 750

Glu Glu Lys Asp Glu Cys Ala Met Ile Ser Thr Ser Ile Gly Glu Glu
            755                 760                 765

Phe Glu Leu Pro Ile Ser Ser Ala Thr Thr Ile Lys Cys Ala Glu Ser
770                 775                 780

Phe Ser Arg Leu Leu Gln Gln Trp Lys Lys Gly Leu Gln Val Gln Ser
785                 790                 795                 800

<210> SEQ ID NO 11
<211> LENGTH: 2426
<212> TYPE: DNA
<213> ORGANISM: Homo sapiens

<400> SEQUENCE: 11

| tctgttcccg agctggagct gcgttgggac ccgtcggatc gtaaatccca tgtaaggtat | 60   |
| ctgccgtcgg aagatttgaa ctttctaatt ggacacctaa cacccacagt cctccaggtg | 120  |
| ggtcctaaga tcttaggag caacgatggg gggtcctaag ccagggggg atgagggtct   | 180  |
| ggctctcagt ccccgcctcg cggggagtgc ctccccctc tgcgatgggg gtcctaagag | 240  |
| ccagtggggg aaccagggc tggctctcag tccctgcctc gcgggggtg cctccccccc   | 300  |
| tgtgatgggg gtactaacag ccaggggcgg aagagggat agctctcagt ccccaccttc  | 360  |
| gcggggggtg cctcccctc gtgcgatggg ggtcctaaga tccaggggg gaagagggac   | 420  |
| tggctctcag tccctgcctc gcgggggtg cctcccccc tgcgatgggg gtactcacag   | 480  |
| ccaggggtgg aagagggat agctctcagt ccccactctc gtgggggtg cctcccctc    | 540  |
| ctgcgatggg ggtcctcaga gccgggggg aagagggtct ggctctcagt aatcccacgt  | 600  |
| aaggtacctg ctgtcggaag atttgaactt tctacttgga caactaacac ccacagtcct | 660  |
| ccaggtgggt cctaaggatc ttaggatcaa tgatggggg tcctaagccg gtgggggaag  | 720  |
| agggtctggc tctcagtccc cgcctcgcg gggtgcctc cccctctgc gatgggggtc    | 780  |
| ctaagagcca gtggggaac cagggctgg ctctcaatcc ctgcctcgcg ggggttactc   | 840  |
| ccccctcctg cgatggggt accaacagcc agggcggaa gagggatag ctctcagtcc    | 900  |
| ccacctcgt ggggttgcct ccccctcctg cgatgggggt cctaagatcc tgggaggaa   | 960  |
| gagggactgg ctctcagtaa tcccacctaa ggtacctgcc gtcggaagat ttgaacttc   | 1020 |

```
tacttggaca actaacaccc acagtcctcc aggtgggtcc taaggatctt aggatcaatg    1080 atgggggtc ctaagccagg ggggaagagg gtctggcact cagtccctgc ctcgcgggg      1140 gtgcctccgc ccccagcgat gggggtccta agagcaaagg ggggaagagg ggctccctct    1200
cagtccccgc gtcgcgaggg gtgcctcccc ccctgcgatg gcggtgcaaa gagccagggg    1260
aggaaagagg gaggttcgca gtccccgcct cgcgggaatt gcctccccc ctgctatggt     1320 ggtcccaaga gccagggggg gaagaggggt tggctctgag tccccgcctc gcgggggtg     1380 cctccccccc tgcgatggga gtcccaagag ccagggggta agaggggatg gatctcagcc    1440
atcacaaaat ggggggcctt tatgttcagg ttttacccaa gaatcagctt atttgcttct    1500
tgtactagca gggcagttgc tgccaaggcc ctcaaatagg ggggccatcc tttagcaacc    1560
ctgtctagtt gtttagagac gtaggctacg ggcctcagcc agggccccac agtttgggtt    1620
aaaagtccag ctgccatctt ttctctctct gacgcataca atggaaaagg ctttgtcagg    1680
tcgggtgggc tgccagaaga ttttcttgta actcatgaaa aacttgctgt tgttgggatc    1740
cccatttcaa aagttccggg tccccgcccc atttgtgacc tcatacaaag gcttggctaa    1800
tactgcagtt tgggatccac agcctacaaa accccacagc tcctaagaat tctctcacct    1860
gccttctgcc cttaagctcc ggtagattgc aaataacctg ctttcttcct gttcccgagc    1920
tgtgttcgga cccgtcggat cgtaaatccc acgtaaggtc ggaagatttg aactttctac    1980
ttggacacct aacacccaca gtcctccagg tacctgccgt cggaagattt gaacgttcta    2040
cttggacaac taacacccac agtcctccag acagaaagac aacaggtaca aagccctaag    2100
gattataaag gtatgctgct taccatcatc ttagtgacca aggcagcgaa gctgtttctg    2160
taccttggaa cagtcttccc tgacaagcca gagaacagtg ataaagccac cagccttggg    2220
atcaggactg aaaaggcaag agtgatggag atttctcctg cgctaagcca agagaaggtt    2280
tcagcacttc agacagctcc caccgaagta gccgcgctcc cagctgcttg cagatgttga    2340
aaaggaaagc ctcggtttgt cttgaggttg tcagcaggtg caagacacgt aataaaatgc    2400
aatgtgttcc taaaaaaaaa aaaaaa                                          2426
```

<210> SEQ ID NO 12
<211> LENGTH: 75
<212> TYPE: PRT
<213> ORGANISM: Homo sapiens

<400> SEQUENCE: 12

```
Met Leu Leu Thr Ile Ile Leu Val Thr Lys Ala Ala Lys Leu Phe Leu
 1               5                  10                  15

Tyr Leu Gly Thr Val Phe Pro Asp Lys Pro Glu Asn Ser Asp Lys Ala
            20                  25                  30

Thr Ser Leu Gly Ile Arg Thr Glu Lys Ala Arg Val Met Glu Ile Ser
        35                  40                  45

Pro Ala Leu Ser Gln Glu Lys Val Ser Ala Leu Gln Thr Ala Pro Thr
    50                  55                  60

Glu Val Ala Ala Leu Pro Ala Ala Cys Arg Cys
65                  70                  75
```

<210> SEQ ID NO 13
<211> LENGTH: 429
<212> TYPE: DNA
<213> ORGANISM: Homo sapiens
<220> FEATURE:
<221> NAME/KEY: unsure

```
<222> LOCATION: (10)
<220> FEATURE:
<221> NAME/KEY: unsure
<222> LOCATION: (18)..(19)
<220> FEATURE:
<221> NAME/KEY: unsure
<222> LOCATION: (24)
<220> FEATURE:
<221> NAME/KEY: unsure
<222> LOCATION: (97)
<220> FEATURE:
<221> NAME/KEY: unsure
<222> LOCATION: (117)
<220> FEATURE:
<221> NAME/KEY: unsure
<222> LOCATION: (142)..(143)

<400> SEQUENCE: 13
cttggtccan ttggttttnnt tcgnttcccc cttttcttc ccttggttt tcttttttt       60 cgggcaacaa tattttccaa ggctaatacc aaggcanacc aattcaactc ccaaggntcg    120 ggaatttta acctttttaat tnnatggccc ctcccactcc ttttctacgg cgatttgtct    180
gtgtctggcc cccacccact gcccatcccc cattgttgtc tggatgtggt tctatttttt    240
atcggtctcc tttccctcc tccccgttct cgccccgcc ccaccccctg ctcccactac      300
cctttgtctc ttgctctttc ttgggcttct gtacaactca acttgtatac actgtgtaca    360
cacaaccagc caaacgaaaa cccaacggcr aamaaaaaaa aaaaaaaaaa aaaaaaaaa     420 aaaaaaaa                                                            429

<210> SEQ ID NO 14
<211> LENGTH: 130
<212> TYPE: PRT
<213> ORGANISM: Homo sapiens
<220> FEATURE:
<221> NAME/KEY: UNSURE
<222> LOCATION: (4)
<220> FEATURE:
<221> NAME/KEY: UNSURE
<222> LOCATION: (6)..(7)
<220> FEATURE:
<221> NAME/KEY: UNSURE
<222> LOCATION: (33)
<220> FEATURE:
<221> NAME/KEY: UNSURE
<222> LOCATION: (48)

<400> SEQUENCE: 14

Leu Gly Pro Xaa Gly Xaa Xaa Arg Phe Pro Leu Phe Leu Pro Leu Gly
  1               5                  10                  15

Phe Leu Phe Phe Arg Ala Thr Ile Phe Ser Lys Ala Asn Thr Lys Ala
             20                  25                  30

Xaa Gln Phe Asn Ser Gln Gly Ser Gly Ile Phe Asn Leu Leu Ile Xaa
         35                  40                  45

Trp Pro Leu Pro Leu Leu Phe Tyr Gly Asp Leu Ser Val Ser Gly Pro
     50                  55                  60

His Pro Leu Pro Ile Pro His Cys Cys Leu Asp Val Val Leu Phe Phe
 65                  70                  75                  80

Ile Gly Leu Leu Ser Pro Pro Arg Ser Arg Pro Arg Pro Thr Pro
                 85                  90                  95

Cys Ser His Tyr Pro Leu Ser Leu Ala Leu Ser Trp Ala Ser Val Gln
            100                 105                 110

Leu Asn Leu Tyr Thr Leu Cys Thr His Asn Gln Pro Asn Glu Asn Pro
            115                 120                 125
```

Thr Ala
    130

<210> SEQ ID NO 15
<211> LENGTH: 271
<212> TYPE: DNA
<213> ORGANISM: Homo sapiens

<400> SEQUENCE: 15

| gccccttcca | cctcttctcc | tatgacttkg | aggactcctc | cctgtccacc | aaggagaagg | 60 |
| aagcagagtc | ccagaaggaa | aacagataca | gcaattttgg | caataactct | tatcactcct | 120 |
| caagaccctc | atctggatcc | agtgtgccca | ccaccccac | atcatccgtc | tcaccccac | 180 |
| aggaggccag | gttggaaagg | tcatcaccga | gtggtcttct | cacatcatcc | ttcaggcagc | 240 |
| accaagagtc | actggcaaaa | aaaaaaaaa  | a          |            |            | 271 |

<210> SEQ ID NO 16
<211> LENGTH: 38
<212> TYPE: PRT
<213> ORGANISM: Homo sapiens

<400> SEQUENCE: 16

Val Pro Thr Thr Pro Thr Ser Ser Val Ser Pro Pro Gln Glu Ala Arg
 1               5                  10                  15

Leu Glu Arg Ser Ser Pro Ser Gly Leu Leu Thr Ser Ser Phe Arg Gln
            20                  25                  30

His Gln Glu Ser Leu Ala
        35

<210> SEQ ID NO 17
<211> LENGTH: 1630
<212> TYPE: DNA
<213> ORGANISM: Homo sapiens
<220> FEATURE:
<221> NAME/KEY: unsure
<222> LOCATION: (1622)

<400> SEQUENCE: 17

| cctgacctca | ggtgatctgc | ccgcctcggc | ctctgaaagt | gctgggatta | taggcatgag | 60 |
| ccaacatgcc | tgacctgtta | tttatttaa  | attatatcag | gaatacacac | acacacacac | 120 |
| acacacacac | acacacacac | acaacttata | aagataatgg | tctccttggc | actcccaccc | 180 |
| acccacccat | ccaaatttac | acaagtaaat | ctgtaatcaa | tttggttaga | agggatttat | 240 |
| tttaatattt | ttggggattg | cttatgatgc | agtataattt | ttagttatat | tagtagtaat | 300 |
| tggaaatgtg | tattttgtg  | actgaagtca | ccttctaaat | aatttctaga | ataaaatttt | 360 |
| tatattgaag | aagttggtct | taaccatttt | tttttcagga | gcatgcattt | tgaaatcatt | 420 |
| ctgtgggaag | atgaaaacaa | atttagttct | atgtctcccc | tttttagaga | tgttgacact | 480 |
| ttccttaaat | gtaccatgca | tgatttgtct | accacccttt | tagcttgtta | tacttaaatc | 540 |
| ccagatctct | gtcttcccat | ttcagtttct | ctagaatttc | tggctgcttc | caatgggtca | 600 |
| aatttatgag | tgaaccatta | agaatcactt | agtgtagaaa | taaccatgg  | gttaggagtt | 660 |
| tgaacactgc | ctaggttctg | tttctgattt | gattatgact | cagctgtgtg | gccttgggaa | 720 |
| accaccttac | tggtatccct | atccttgcag | aagcaagaga | gttaatgatg | gttgacttaa | 780 |
| tctcttgtgg | ttattatgaa | gatcagataa | gatacattaa | cacattttgc | caactgaatt | 840 |
| aggttattta | tttacatgtg | tgtccatgga | cctggggatc | aggtgctatg | tctcagccct | 900 |

-continued

```
atctttgttt ttaatcctgt gtctctaatt gtgtttgtca gtaaaggagt gagtcattta      960
atggttgcta gatgtttgag taaaacaaac aagcaaacaa atggtaaatt agtactattt     1020 cttttttaaaa aatttttttt tacatttttaa aaattataga taaatacaga gatgaggtct   1080
caccatgttg cccagtctgg tttcaaactc ctaaactcaa gtgatcctct ctcctcagcc     1140
tcccaaagtg ctaggattac aggcgtgagc caccatgcct ggccagtagt actatttctt     1200
tgggaaaata tttagtagta gtcaacaaag ttgagcatac tgtgacctgg cagttttgat    1260
gctaagtawa tacccaacag aaatgcaaac atatacttac caaaactcat gtccaagaat    1320
attcgtagaa gcacaattct tatgatagca aaaaggtaga aaacaacyta aatgttttyta   1380 agcagtagca taagagtaat accgtgtggt ttgtttatac agtgagatcc tgtacagcca    1440
tgtaaaagac caaaatattc cctgtaacaa tgagaatgaa tctcctgtgc ttgcttcggc    1500
agcacataca ctaaaattgg aacgatacag agattagcat ggcccctgtg caaggagaat   1560
gaatyttcgt aatgttcagc aaaagaagcc agatataaat gaatattcca ttttataaaa    1620 anaaaaaaaa                                                            1630
```

<210> SEQ ID NO 18
<211> LENGTH: 30
<212> TYPE: PRT
<213> ORGANISM: Homo sapiens

<400> SEQUENCE: 18

```
Met Lys Thr Asn Leu Val Leu Cys Leu Pro Phe Leu Glu Met Leu Thr
  1               5                  10                  15

Leu Ser Leu Asn Val Pro Cys Met Ile Cys Leu Pro Pro Phe
             20                  25                  30
```

<210> SEQ ID NO 19
<211> LENGTH: 456
<212> TYPE: DNA
<213> ORGANISM: Homo sapiens

<400> SEQUENCE: 19

```
aagaaggaga ctgtaagctt gtttgtacaa aaacatacca tacagagaaa gctgaagaca       60
aacaaaagtt agaattcttg aaaaaaagca tgttattgaa ttatcaacat cactggattg      120
tggataatat gcctgtaacg tggtgttacg atgttgaaga tggtcaggtt ctgtaatcct      180
ggatttccta ttggctgtta cattacagat aaaggccatg caaagatgc ctgtgttatt       240 agttcagatt ccatgaaag atacatttt acatcttca accatgttga catcaaaata        300
tactatcatg ttgttgaaac tgggtccatg ggagcaagat tagtggctgc taaacttgaa     360
ccgaaaagct tcaaacatac ccatatagat aaaccagact gctcagggcc ccccatggac     420
ataagtaaca aggcttctgg ggagataaaa attgca                                456
```

<210> SEQ ID NO 20
<211> LENGTH: 519
<212> TYPE: DNA
<213> ORGANISM: Homo sapiens
<220> FEATURE:
<221> NAME/KEY: unsure
<222> LOCATION: (4)
<220> FEATURE:
<221> NAME/KEY: unsure
<222> LOCATION: (12)
<220> FEATURE:
<221> NAME/KEY: unsure
<222> LOCATION: (28)
<220> FEATURE:

<221> NAME/KEY: unsure
<222> LOCATION: (35)..(36)
<220> FEATURE:
<221> NAME/KEY: unsure
<222> LOCATION: (51)
<220> FEATURE:
<221> NAME/KEY: unsure
<222> LOCATION: (63)..(65)
<220> FEATURE:
<221> NAME/KEY: unsure
<222> LOCATION: (90)
<220> FEATURE:
<221> NAME/KEY: unsure
<222> LOCATION: (111)..(112)
<220> FEATURE:
<221> NAME/KEY: unsure
<222> LOCATION: (123)
<220> FEATURE:
<221> NAME/KEY: unsure
<222> LOCATION: (136)
<220> FEATURE:
<221> NAME/KEY: unsure
<222> LOCATION: (148)
<220> FEATURE:
<221> NAME/KEY: unsure
<222> LOCATION: (157)
<220> FEATURE:
<221> NAME/KEY: unsure
<222> LOCATION: (161)
<220> FEATURE:
<221> NAME/KEY: unsure
<222> LOCATION: (204)
<220> FEATURE:
<221> NAME/KEY: unsure
<222> LOCATION: (239)
<220> FEATURE:
<221> NAME/KEY: unsure
<222> LOCATION: (305)

<400> SEQUENCE: 20

```
caantaataa ancttttgtt tccctcgnca ttgtnntcgt tcccctgtcc ngccttgttt      60
ccnnngtcct gcaccaatat ttccaaaccn aatacccaag catacaatcc nnactccaag    120
ctnggaattc gcccanagag accgtcgngg gaagaanttg nctggaaact tgttcatggt    180
gatatatacc gtcctccaag aaangggatg ctgctatcag tctttctagg agccgggana    240
cagatattaa ttatgacctt tgtgactcta tttttcgctt gcctgggagt tttgtcacct    300
cccanccgag gagcgctgat gacgtgtgct gtggtcctgt gggtgctgct gggcacccct    360
gcaggctatg tttctgccag attctataag tcctttggag gtgagaagtg gaaaacaaat    420
gttttattaa catcatttct ttgtcctggg attgtatttg ctgacttctt tataatgaat    480
ctgatcctct ggtcaacggc ctctttggcc ctcgagaca                           519
```

<210> SEQ ID NO 21
<211> LENGTH: 89
<212> TYPE: PRT
<213> ORGANISM: Homo sapiens
<220> FEATURE:
<221> NAME/KEY: UNSURE
<222> LOCATION: (18)

<400> SEQUENCE: 21

```
Met Thr Phe Val Thr Leu Phe Phe Ala Cys Leu Gly Val Leu Ser Pro
 1               5                  10                  15

Pro Xaa Arg Gly Ala Leu Met Thr Cys Ala Val Val Leu Trp Val Leu
                20                  25                  30

Leu Gly Thr Pro Ala Gly Tyr Val Ser Ala Arg Phe Tyr Lys Ser Phe
             35                  40                  45
```

```
Gly Gly Glu Lys Trp Lys Thr Asn Val Leu Leu Thr Ser Phe Leu Cys
 50                  55                  60

Pro Gly Ile Val Phe Ala Asp Phe Phe Ile Met Asn Leu Ile Leu Trp
 65                  70                  75                  80

Ser Thr Ala Ser Leu Ala Leu Glu Thr
                 85
```

<210> SEQ ID NO 22
<211> LENGTH: 507
<212> TYPE: DNA
<213> ORGANISM: Homo sapiens

<400> SEQUENCE: 22

```
ttcttcccat acacctttcc cccataagat gtgtcttcaa cactataaag catttgtatt      60
gtgatttgat taagtatata tttggttgtt ctcaatgaag agcaaattta aatattatgt     120
gcatttgtaa atacagtagc tataaaattt tccatacttc taatggcaga atagaggagg     180
ccatattaaa taatactgat gaaaggcagg acactgcatt gtaaatagga ttttctaggc     240
tcggtaggca gaaagaatta ttttttcttt g aaggaaataa cttttttatca tggtaatttt   300 gaaggatgat tcctatgatg tgttcaccag gggaatgtgg cttttaaaga aaatcttcta     360
ttggttgtaa ctgttcatat cttcttactt ttctgtgttg acttcattat tcccatggta     420
ttggcctttt aaactatgtg cctctgagtc tttcaattta taaatttgta tcttaataaa     480
tattataaaa atgaaaaaaa aaaaaaa                                         507
```

<210> SEQ ID NO 23
<211> LENGTH: 622
<212> TYPE: DNA
<213> ORGANISM: Homo sapiens
<220> FEATURE:
<221> NAME/KEY: unsure
<222> LOCATION: (32)
<220> FEATURE:
<221> NAME/KEY: unsure
<222> LOCATION: (57)
<220> FEATURE:
<221> NAME/KEY: unsure
<222> LOCATION: (66)
<220> FEATURE:
<221> NAME/KEY: unsure
<222> LOCATION: (72)
<220> FEATURE:
<221> NAME/KEY: unsure
<222> LOCATION: (105)

<400> SEQUENCE: 23

```
ggttcttcgg gacacccgtg gatggacacg gnaaggaaac accaggccaa ccacagntgg      60
ggatanaata gnacaaccac accctgccgt ccagagcctc ccagnctgtg ccccgtccta     120
gtaccaccag caaccatcaa tcccgtctcc tcctgcctcc tctcctgcaa tccacccgc      180 cacgactatc gccatggcag ccctgatcgc agagaacttc cgcttcctgt cacttttctt     240
caagagcaag gatgtgatga ttttcaacgg cctggtggca ctgggcacgg tgggcagcca     300
ggagctgttc tctgtggtgg ccttccactg cccctgctcg ccggcccgga actacctgta     360
cgggctggcg gccatcggcg tgcccgccct ggtgctcttc atcattggca tcatcctcaa     420
caaccacacc tggaacctcg tggccgagtg ccagcaccgg aggaccaaga actgctccgc     480
cgcccccacc ttcctccttc taagctccat cctgggacgt gcggctgtgg ccctgtcac     540 ctggtctgtc atctccctgc tgcgtggtga ggcttatgtc tgtgctctca gtgagttcgt     600
ggacccttcc tcactcacgg cc                                              622
```

<210> SEQ ID NO 24
<211> LENGTH: 143
<212> TYPE: PRT
<213> ORGANISM: Homo sapiens

<400> SEQUENCE: 24

```
Met Ala Ala Leu Ile Ala Glu Asn Phe Arg Phe Leu Ser Leu Phe Phe
 1               5                  10                  15

Lys Ser Lys Asp Val Met Ile Phe Asn Gly Leu Val Ala Leu Gly Thr
            20                  25                  30

Val Gly Ser Gln Glu Leu Phe Ser Val Val Ala Phe His Cys Pro Cys
        35                  40                  45

Ser Pro Ala Arg Asn Tyr Leu Tyr Gly Leu Ala Ala Ile Gly Val Pro
    50                  55                  60

Ala Leu Val Leu Phe Ile Ile Gly Ile Ile Leu Asn Asn His Thr Trp
65                  70                  75                  80

Asn Leu Val Ala Glu Cys Gln His Arg Arg Thr Lys Asn Cys Ser Ala
                85                  90                  95

Ala Pro Thr Phe Leu Leu Leu Ser Ser Ile Leu Gly Arg Ala Ala Val
            100                 105                 110

Ala Pro Val Thr Trp Ser Val Ile Ser Leu Leu Arg Gly Glu Ala Tyr
            115                 120                 125

Val Cys Ala Leu Ser Glu Phe Val Asp Pro Ser Ser Leu Thr Ala
            130                 135                 140
```

<210> SEQ ID NO 25
<211> LENGTH: 314
<212> TYPE: DNA
<213> ORGANISM: Homo sapiens
<220> FEATURE:
<221> NAME/KEY: unsure
<222> LOCATION: (38)
<220> FEATURE:
<221> NAME/KEY: unsure
<222> LOCATION: (50)
<220> FEATURE:
<221> NAME/KEY: unsure
<222> LOCATION: (58)
<220> FEATURE:
<221> NAME/KEY: unsure
<222> LOCATION: (63)
<220> FEATURE:
<221> NAME/KEY: unsure
<222> LOCATION: (65)
<220> FEATURE:
<221> NAME/KEY: unsure
<222> LOCATION: (70)
<220> FEATURE:
<221> NAME/KEY: unsure
<222> LOCATION: (77)
<220> FEATURE:
<221> NAME/KEY: unsure
<222> LOCATION: (82)
<220> FEATURE:
<221> NAME/KEY: unsure
<222> LOCATION: (84)
<220> FEATURE:
<221> NAME/KEY: unsure
<222> LOCATION: (94)
<220> FEATURE:
<221> NAME/KEY: unsure
<222> LOCATION: (113)
<220> FEATURE:
<221> NAME/KEY: unsure
<222> LOCATION: (132)
<220> FEATURE:
<221> NAME/KEY: unsure

```
<222> LOCATION: (144)
<220> FEATURE:
<221> NAME/KEY: unsure
<222> LOCATION: (155)
<220> FEATURE:
<221> NAME/KEY: unsure
<222> LOCATION: (165)
<220> FEATURE:
<221> NAME/KEY: unsure
<222> LOCATION: (171)
<220> FEATURE:
<221> NAME/KEY: unsure
<222> LOCATION: (183)
<220> FEATURE:
<221> NAME/KEY: unsure
<222> LOCATION: (198)
<220> FEATURE:
<221> NAME/KEY: unsure
<222> LOCATION: (216)
<220> FEATURE:
<221> NAME/KEY: unsure
<222> LOCATION: (234)
<220> FEATURE:
<221> NAME/KEY: unsure
<222> LOCATION: (249)
<220> FEATURE:
<221> NAME/KEY: unsure
<222> LOCATION: (254)
<220> FEATURE:
<221> NAME/KEY: unsure
<222> LOCATION: (256)

<400> SEQUENCE: 25
ttttaaaaaa cttttatctt cttggccagg ggaaaggncc cccaggcaan ctggggtntg      60
gananaccca naaaacnatg gnancccaa ccancagggc caggttacag tgnaactccc     120
cagtgggccc cnttatggga ctcnattcag ttaanattta tctancttca nagggacacc    180
cancccaaca gttccccnct ggggagtggc ccccanttca acctctggcc ttantttaaa    240
aaattaaant tttnanaaag tttttcttac taaaagggaa aaaaaaaaaa aaaaaaaaa     300 aaaaaaaaaa aaaa                                                      314

<210> SEQ ID NO 26
<211> LENGTH: 533
<212> TYPE: DNA
<213> ORGANISM: Mus musculus
<220> FEATURE:
<221> NAME/KEY: unsure
<222> LOCATION: (32)
<220> FEATURE:
<221> NAME/KEY: unsure
<222> LOCATION: (38)

<400> SEQUENCE: 26
gggatatccc atacaggtat gaaaaaccc cntatgtnat agtgttctat agcacacaat      60
accttatgaa ggaagggttt satgaataca tggcagaaga caatcatgaa agamttatyt    120
tgaggggyta gaartaatga gtttggaggt gtgcccctta ggtcctgart gtcctgggat    180
ccctmacccc taatttctct cccaragcat yatcccttct cagtattggt actacatgat    240
tgaactttcc ttctastggt ccctgytctt cagcattgcc tctgatgtcw agcgaaagga   300
ttttaaggaa cagatcatcc accatgtggc cactatcatt ctcctctgct tctcctggtt   360
tgccaattac gtccgggcag ggaccctcat catggctctg catgacgctt ctgactacct   420
gctggagtct gccaagatgt ttaactacgc gggatggaag aacacctgca caacctctt   480 cattgtgttc gccatcgttt tcatcatcac tcggctggtt atcatgcctt tct         533
```

<210> SEQ ID NO 27
<211> LENGTH: 44
<212> TYPE: PRT
<213> ORGANISM: Mus musculus

<400> SEQUENCE: 27

Met Thr Leu Leu Thr Thr Cys Trp Ser Leu Pro Arg Cys Leu Thr Thr
1               5                   10                  15

Arg Asp Gly Arg Thr Pro Ala Thr Thr Ser Ser Leu Cys Ser Pro Ser
            20                  25                  30

Phe Ser Ser Ser Leu Gly Trp Leu Ser Cys Leu Ser
        35                  40

<210> SEQ ID NO 28
<211> LENGTH: 313
<212> TYPE: DNA
<213> ORGANISM: Mus musculus
<220> FEATURE:
<221> NAME/KEY: unsure
<222> LOCATION: (4)
<220> FEATURE:
<221> NAME/KEY: unsure
<222> LOCATION: (33)
<220> FEATURE:
<221> NAME/KEY: unsure
<222> LOCATION: (35)
<220> FEATURE:
<221> NAME/KEY: unsure
<222> LOCATION: (94)
<220> FEATURE:
<221> NAME/KEY: unsure
<222> LOCATION: (226)

<400> SEQUENCE: 28
aaanacaagt caatgaagtg aaggagggta tgnanacatg cccctcacca taccccaggg      60
accatggttc ctaggatctc actgcctccc tttntggcct tcctgtcccc tcccttcagc    120
tatgacagct ggtgtggagt agaagggcaa ctagttctgt tatttattga acatttgggg    180
tttcagttgt aaagccacaa ctacaggtag gacctgatat ttcggngagg gaccatttca    240
gaccaaaatg tactgttaat ttttttttaat taaagtatat taaaggttaa ataaaaaaaa    300
aaaaaaaaaa aaa                                                       313

<210> SEQ ID NO 29
<211> LENGTH: 525
<212> TYPE: DNA
<213> ORGANISM: Mus musculus
<220> FEATURE:
<221> NAME/KEY: unsure
<222> LOCATION: (22)
<220> FEATURE:
<221> NAME/KEY: unsure
<222> LOCATION: (52)
<220> FEATURE:
<221> NAME/KEY: unsure
<222> LOCATION: (55)
<220> FEATURE:
<221> NAME/KEY: unsure
<222> LOCATION: (59)

<400> SEQUENCE: 29
aaagacatcc actttgcctt tntctccaca ggtgtccact cccaggtcca antgnaggng      60
agcctgaatt cggccaaaga ggcctaatta caatcatttc aaattttgaa ttttttaagtt    120 gatgggctct taagtggtcc gttctgaata raaaccaatt tgctagtttc ggttttgttt    180
tgttttgttt tgttttgttt tgttttgttt ttttaaggaa tcagatagcc agaaaaaaaa    240

```
atgctattgc ttgttttcat gaacttcagt tgtctctttt tagtaaaccc agtactttcc    300
acaaagtctt ctctgacctt ccccatcact ggacggttca cccatcttct tctccaagtg    360
tttatccccc agcccaagcc tttcctgctg caagccaagc ctgctacatt tgttacagac    420
caagcttata cacagctcga caactgcact cccactgtag gctccggtgt gtactcttgt    480
cttgtgttgg gaaggggaag tgaagtgata agccagaatt ttttt                    525
```

<210> SEQ ID NO 30
<211> LENGTH: 95
<212> TYPE: PRT
<213> ORGANISM: Mus musculus

<400> SEQUENCE: 30

```
Met Leu Leu Leu Val Phe Met Asn Phe Ser Cys Leu Phe Leu Val Asn
  1               5                  10                  15

Pro Val Leu Ser Thr Lys Ser Ser Leu Thr Phe Pro Ile Thr Gly Arg
                 20                  25                  30

Phe Thr His Leu Leu Leu Gln Val Phe Ile Pro Gln Pro Lys Pro Phe
             35                  40                  45

Leu Leu Gln Ala Lys Pro Ala Thr Phe Val Thr Asp Gln Ala Tyr Thr
         50                  55                  60

Gln Leu Asp Asn Cys Thr Pro Thr Val Gly Ser Gly Val Tyr Ser Cys
 65                  70                  75                  80

Leu Val Leu Gly Arg Gly Ser Glu Val Ile Ser Gln Asn Phe Phe
                 85                  90                  95
```

<210> SEQ ID NO 31
<211> LENGTH: 270
<212> TYPE: DNA
<213> ORGANISM: Mus musculus
<220> FEATURE:
<221> NAME/KEY: unsure
<222> LOCATION: (47)
<220> FEATURE:
<221> NAME/KEY: unsure
<222> LOCATION: (71)
<220> FEATURE:
<221> NAME/KEY: unsure
<222> LOCATION: (91)
<220> FEATURE:
<221> NAME/KEY: unsure
<222> LOCATION: (94)
<220> FEATURE:
<221> NAME/KEY: unsure
<222> LOCATION: (105)
<220> FEATURE:
<221> NAME/KEY: unsure
<222> LOCATION: (170)
<220> FEATURE:
<221> NAME/KEY: unsure
<222> LOCATION: (189)
<220> FEATURE:
<221> NAME/KEY: unsure
<222> LOCATION: (192)
<220> FEATURE:
<221> NAME/KEY: unsure
<222> LOCATION: (210)
<220> FEATURE:
<221> NAME/KEY: unsure
<222> LOCATION: (246)..(247)

<400> SEQUENCE: 31

```
aggtttcttg ggaacagctc agcagatttt tgagaccaat caaatgncct cattaagaac     60
tttatctgtt nggaaacatg cttccttcc nggntctgct aaacngaaag ctcatttgtt    120
gttgctgttg ttgttgtttg tttgtccatt tctctttaat tctaatgttn acatcatgtc    180
```
gtgctgtang antctagaaa gccttaattn acttccacca agaaataaag caatatgttg    240
gtaatnngaa aaaaaaaaaa aaaaaaaaaa    270

<210> SEQ ID NO 32
<211> LENGTH: 574
<212> TYPE: DNA
<213> ORGANISM: Mus musculus
<220> FEATURE:
<221> NAME/KEY: unsure
<222> LOCATION: (9)
<220> FEATURE:
<221> NAME/KEY: unsure
<222> LOCATION: (29)
<220> FEATURE:
<221> NAME/KEY: unsure
<222> LOCATION: (37)
<220> FEATURE:
<221> NAME/KEY: unsure
<222> LOCATION: (53)
<220> FEATURE:
<221> NAME/KEY: unsure
<222> LOCATION: (56)
<220> FEATURE:
<221> NAME/KEY: unsure
<222> LOCATION: (68)
<220> FEATURE:
<221> NAME/KEY: unsure
<222> LOCATION: (72)
<220> FEATURE:
<221> NAME/KEY: unsure
<222> LOCATION: (85)
<220> FEATURE:
<221> NAME/KEY: unsure
<222> LOCATION: (118)
<220> FEATURE:
<221> NAME/KEY: unsure
<222> LOCATION: (131)
<220> FEATURE:
<221> NAME/KEY: unsure
<222> LOCATION: (169)..(170)
<220> FEATURE:
<221> NAME/KEY: unsure
<222> LOCATION: (172)
<220> FEATURE:
<221> NAME/KEY: unsure
<222> LOCATION: (180)
<220> FEATURE:
<221> NAME/KEY: unsure
<222> LOCATION: (253)
<220> FEATURE:
<221> NAME/KEY: unsure
<222> LOCATION: (448)
<220> FEATURE:
<221> NAME/KEY: unsure
<222> LOCATION: (452)
<220> FEATURE:
<221> NAME/KEY: unsure
<222> LOCATION: (455)
<220> FEATURE:
<221> NAME/KEY: unsure
<222> LOCATION: (457)
<220> FEATURE:
<221> NAME/KEY: unsure
<222> LOCATION: (459)
<220> FEATURE:
<221> NAME/KEY: unsure
<222> LOCATION: (475)
<220> FEATURE:
<221> NAME/KEY: unsure
<222> LOCATION: (550)
<220> FEATURE:
<221> NAME/KEY: unsure
<222> LOCATION: (572)

<400> SEQUENCE: 32

-continued

```
tttggtcana aaagacaatt tttttgttnt caagctngag gtgtggcagg ctnganattt      60
ggccaaanaa tngagggaca aaganatcca ctttgccttt ttttccacag gtgtccantc     120
ccaggtccaa ntgcaggcgg gtccacaggc cgcagccatg ggtagccgnn tntcccgagn     180
ggarttcgaa tgggtytaca cggaccarcc ccacgccgcc cggcgcaagg agatcttagc     240
aaagtatcca ganatcaagt ccttgatgaa acctgaccac aatctgatct ggattgtagc     300
catgatgctt ctcgtccagc tggcttcatt ttacttagtc aaagatttgg actggaaatg     360
ggtcatattt tggtcctatg tctttggcag ctgccttaac cactccatga ctctggctat     420
ccatgagatt tcccacaatt tcccttngg cnccncnang gcctgtggaa ccgcnggttt      480
ggaatgtttg ctaacctctc tctccgaatg gcctactcca tttcctttaa aaaaaacaca     540
tggatcaccn ccggtactcc gaacggataa antr                                 574
```

<210> SEQ ID NO 33
<211> LENGTH: 138
<212> TYPE: PRT
<213> ORGANISM: Mus musculus
<220> FEATURE:
<221> NAME/KEY: UNSURE
<222> LOCATION: (5)
<220> FEATURE:
<221> NAME/KEY: UNSURE
<222> LOCATION: (8)
<220> FEATURE:
<221> NAME/KEY: UNSURE
<222> LOCATION: (32)
<220> FEATURE:
<221> NAME/KEY: UNSURE
<222> LOCATION: (97)
<220> FEATURE:
<221> NAME/KEY: UNSURE
<222> LOCATION: (99)..(101)

<400> SEQUENCE: 33

```
Met Gly Ser Arg Xaa Ser Arg Xaa Glu Phe Glu Trp Val Tyr Thr Asp
 1               5                  10                  15

Gln Pro His Ala Ala Arg Arg Lys Glu Ile Leu Ala Lys Tyr Pro Xaa
             20                  25                  30

Ile Lys Ser Leu Met Lys Pro Asp His Asn Leu Ile Trp Ile Val Ala
         35                  40                  45

Met Met Leu Leu Val Gln Leu Ala Ser Phe Tyr Leu Val Lys Asp Leu
     50                  55                  60

Asp Trp Lys Trp Val Ile Phe Trp Ser Tyr Val Phe Gly Ser Cys Leu
 65                  70                  75                  80

Asn His Ser Met Thr Leu Ala Ile His Glu Ile Ser His Asn Phe Pro
                 85                  90                  95

Xaa Gly Xaa Xaa Xaa Ala Cys Gly Thr Ala Gly Leu Glu Cys Leu Leu
            100                 105                 110

Thr Ser Leu Ser Glu Trp Pro Thr Pro Phe Pro Leu Lys Lys Thr His
        115                 120                 125

Gly Ser Pro Pro Val Leu Arg Thr Asp Lys
    130                 135
```

<210> SEQ ID NO 34
<211> LENGTH: 216
<212> TYPE: DNA
<213> ORGANISM: Mus musculus
<220> FEATURE:
<221> NAME/KEY: unsure
<222> LOCATION: (69)
<220> FEATURE:

```
<221> NAME/KEY: unsure
<222> LOCATION: (86)
<220> FEATURE:
<221> NAME/KEY: unsure
<222> LOCATION: (114)
<220> FEATURE:
<221> NAME/KEY: unsure
<222> LOCATION: (116)
<220> FEATURE:
<221> NAME/KEY: unsure
<222> LOCATION: (119)
<220> FEATURE:
<221> NAME/KEY: unsure
<222> LOCATION: (142)

<400> SEQUENCE: 34
atgaagtgct ttttggagga gcttttgttt agtccaacag gagtccaagg atgcagatta      60
gagttttgng agtttgctgc ccttgntggg ctaggcattt cattgttgta actncntcng    120
agtaactgat gatcctataa gnaacccaa taaatttttt ggtttactaa aaaaaaaaaa    180
aaaaaaaaaa aaaaaaaaaa aaaaaaaaaa aaaaaa                             216

<210> SEQ ID NO 35
<211> LENGTH: 526
<212> TYPE: DNA
<213> ORGANISM: Mus musculus
<220> FEATURE:
<221> NAME/KEY: unsure
<222> LOCATION: (6)
<220> FEATURE:
<221> NAME/KEY: unsure
<222> LOCATION: (25)
<220> FEATURE:
<221> NAME/KEY: unsure
<222> LOCATION: (53)

<400> SEQUENCE: 35
acaggngtcc aatcccaggt ccaantgcag gggagcctga attcggccaa agnggcctag      60
cctcccaagt gstgggatta aaggsgtgtg ccaccatgcc ccacttcata tgttatattt    120
ttaatgaata aagagtggaa aaattatgta tcacatgtgt taatttgggg agaagcgctt    180
tataacagag ggcttactyt caattaaaga gaacaaaggr aaatgtgtty tacaggcagt    240
gtataccttt gacctctgaa aaacctata tagtttctcc tacagacacc ttgccagtaa    300
ccttacaggt cttataggag agcagatcca agttgccagg ctgatctgca agcacaaaca    360
tttgtcaagg gaaagcacag gtcgttactt tcagtacaaa atggttcttt gctatggatg    420
gattctcttc ttcttgcccc atgtcctgtt cccaaggacc gacttcctgc agcactgtgg    480
tggactcttc tatgaggaga caacatctgg gccttattca atagcc                   526

<210> SEQ ID NO 36
<211> LENGTH: 42
<212> TYPE: PRT
<213> ORGANISM: Mus musculus

<400> SEQUENCE: 36

Met Val Leu Cys Tyr Gly Trp Ile Leu Phe Phe Leu Pro His Val Leu
  1               5                  10                  15

Phe Pro Arg Thr Asp Phe Leu Gln His Cys Gly Gly Leu Phe Tyr Glu
                 20                  25                  30

Glu Thr Thr Ser Gly Pro Tyr Ser Ile Ala
             35                  40

<210> SEQ ID NO 37
```

```
<211> LENGTH: 208
<212> TYPE: DNA
<213> ORGANISM: Mus musculus
<220> FEATURE:
<221> NAME/KEY: unsure
<222> LOCATION: (8)
<220> FEATURE:
<221> NAME/KEY: unsure
<222> LOCATION: (29)
<220> FEATURE:
<221> NAME/KEY: unsure
<222> LOCATION: (31)
<220> FEATURE:
<221> NAME/KEY: unsure
<222> LOCATION: (42)
<220> FEATURE:
<221> NAME/KEY: unsure
<222> LOCATION: (55)
<220> FEATURE:
<221> NAME/KEY: unsure
<222> LOCATION: (65)
<220> FEATURE:
<221> NAME/KEY: unsure
<222> LOCATION: (75)
<220> FEATURE:
<221> NAME/KEY: unsure
<222> LOCATION: (86)
<220> FEATURE:
<221> NAME/KEY: unsure
<222> LOCATION: (91)
<220> FEATURE:
<221> NAME/KEY: unsure
<222> LOCATION: (98)
<220> FEATURE:
<221> NAME/KEY: unsure
<222> LOCATION: (100)..(101)
<220> FEATURE:
<221> NAME/KEY: unsure
<222> LOCATION: (113)
<220> FEATURE:
<221> NAME/KEY: unsure
<222> LOCATION: (119)
<220> FEATURE:
<221> NAME/KEY: unsure
<222> LOCATION: (121)
<220> FEATURE:
<221> NAME/KEY: unsure
<222> LOCATION: (128)
<220> FEATURE:
<221> NAME/KEY: unsure
<222> LOCATION: (130)..(131)
<220> FEATURE:
<221> NAME/KEY: unsure
<222> LOCATION: (133)
<220> FEATURE:
<221> NAME/KEY: unsure
<222> LOCATION: (137)
<220> FEATURE:
<221> NAME/KEY: unsure
<222> LOCATION: (161)

<400> SEQUENCE: 37
tttgaaangg caacagaaat atttttttgna ntagaaaaag gnatggaacg tggtnccaat      60
tgttnatttt ccttnattta ttcccngtaa ntttgtcngn ngataaattg aanataacng     120
ngattaangn ntnatgntaa aaaaaaaaaa aaaaaaaaaa naaaaaaaaa aaaaaaaaaa     180
aaaaaaaaaa aaaaaaaaaa aaaaaaaa                                       208

<210> SEQ ID NO 38
<211> LENGTH: 535
<212> TYPE: DNA
<213> ORGANISM: Mus musculus
<220> FEATURE:
<221> NAME/KEY: unsure
<222> LOCATION: (6)
```

<220> FEATURE:
<221> NAME/KEY: unsure
<222> LOCATION: (30)
<220> FEATURE:
<221> NAME/KEY: unsure
<222> LOCATION: (60)
<220> FEATURE:
<221> NAME/KEY: unsure
<222> LOCATION: (67)
<220> FEATURE:
<221> NAME/KEY: unsure
<222> LOCATION: (83)
<220> FEATURE:
<221> NAME/KEY: unsure
<222> LOCATION: (99)
<220> FEATURE:
<221> NAME/KEY: unsure
<222> LOCATION: (115)
<220> FEATURE:
<221> NAME/KEY: unsure
<222> LOCATION: (145)
<220> FEATURE:
<221> NAME/KEY: unsure
<222> LOCATION: (160)
<220> FEATURE:
<221> NAME/KEY: unsure
<222> LOCATION: (165)

<400> SEQUENCE: 38

```
atttgntcag aaaagacaat tttttttgttn tcaagcttga ggtgtggcag gcttgagatn      60
tgcccanaca cttgagggac aangacatcc aataacccnt tctctccaca ggtgnccact     120
cccaggtcca actgcaggcg agccngaatt cggccaaagn ggccnaagat cagttagctc     180
cctgggtcgg aacaaggtga aaagcagctt tcttgctttt gaaatcatyt ttgtgacaag     240
gacacatggg gtcagggtag ggtgtccart taaaatagtg tcactgctta gaaaggggwa     300
cttggattcc tttagttagc ttagctctgt ctcttgtttc ataaaacaca ctgggttaga     360
ataraggctc ctgcattaca tggtttgtgt cactgttttt tgttgggttt tcttttttggt     420
ttttcgagac agggtttctc tgtatagccc tggctgtcct araactcact ctgtagacca     480
ggctggcctc gaactcagaa atctgcccgc ttctgcctcc caagtgctgg gatta         535
```

<210> SEQ ID NO 39
<211> LENGTH: 52
<212> TYPE: PRT
<213> ORGANISM: Mus musculus
<220> FEATURE:
<221> NAME/KEY: UNSURE
<222> LOCATION: (28)

<400> SEQUENCE: 39

```
Met Val Cys Val Thr Val Phe Cys Trp Val Phe Phe Leu Val Phe Arg
  1               5                  10                  15

Asp Arg Val Ser Leu Tyr Ser Pro Gly Cys Pro Xaa Thr His Ser Val
             20                  25                  30

Asp Gln Ala Gly Leu Glu Leu Arg Asn Leu Pro Ala Ser Ala Ser Gln
         35                  40                  45

Val Leu Gly Leu
     50
```

<210> SEQ ID NO 40
<211> LENGTH: 308
<212> TYPE: DNA
<213> ORGANISM: Mus musculus
<220> FEATURE:
<221> NAME/KEY: unsure
<222> LOCATION: (43)

```
<220> FEATURE:
<221> NAME/KEY: unsure
<222> LOCATION: (115)
<220> FEATURE:
<221> NAME/KEY: unsure
<222> LOCATION: (134)

<400> SEQUENCE: 40
ggattaaagg catgtgtcac gttttaaatt gatagttata acntcgatgc cacgaatcct      60
gcagtttctc ctgtgctcct ttctttgtgt cagatgggtt aagggttatc agttngggga    120
agaattgtcc ttgnacccccc tggaattatt tttctcaaaa atccaagact ccaaagaaca    180
tgggaaaaat tgttctgtcc acttttgacg ttgaagattt tggttatcct tttcgtactt    240
tctatgtatt ttctatgtaa aattttacac aattaaaaat gttttttttgt ctagtaaaaa    300
aaaaaaaa                                                              308

<210> SEQ ID NO 41
<211> LENGTH: 1351
<212> TYPE: DNA
<213> ORGANISM: Mus musculus
<220> FEATURE:
<221> NAME/KEY: unsure
<222> LOCATION: (134)

<400> SEQUENCE: 41
cagcgcgcgg agccggcgtc ccgttggcgc gctctggcct ggcttcgggt cgtcgcttcg      60
gccccgagga gccgctcgct gtctccggag cggcggagag gatggtgcgg ggcagcccgg    120
ggcccgccgc gcgccgccgc gagtgaacag ggccaggccg cgggcgtccg cgggctcgar    180
ccgccagtct gcggggcggt tgccgctggt gggaagcatg ttcagtatca acccctgga    240
gaacctgaag ctgtacatca gcagccggcc gcccttggtg gtttttatga tcagtgtcag    300
cgccatggcc atcgccttcc tcaccctggg ctacttcttc aagatcaagg agattaagtc    360
cccagaaatg gctgaggatt ggaatacttt tctgctccgg tttaatgatt tggacttgtg    420
tgtatcagaa aacgagacac tgaagcatct ctccaacgat accaccacac cagagagcac    480
catgaccgtc gggcaggcca gatcgtctac ccagccgccc cagtccctgg aggagtcagg    540
ccccatcaat atttcagtgg ccattacctt gaccttggac cctctcaagc cctttggagg    600
gtactctcga aatgttacac acctgtactc caccatcctc gggcatcaga ttggattgtc    660
aggcagggaa gccacgagg agatcaacat caccttcacc ctgcctgctg cctggaacgc    720
cgatgactgt gccctccatg ccactgtga gcaggcggtg ttcacagcat gcatgaccct    780
cacagctgcc cccggagtct tccccgtcac tgttcagcca cctcactgta tccccgacac    840
atacagcaac gccacgctct ggtacaagat cttcacaact gccagagatg ccaacacgaa    900
atatgctcaa gactacaatc ctttctggtg ttataagggt gccattggga agtctacca    960
tgctttaaat cccaaactca ctgttgttgt tccagatgac gaccgctcat taataaaacct    1020
gcatctcatg cacaccagtt acttccttttt cgtgatggtg ataacgatgt tctgctatgc   1080
agtcatcaaa ggcagaccca gcaaactgcg gcagagcaat cctgaatttt gccmtgagaa   1140
ggtggytctg gctgacgcct aatcctacag ctcccattt tytgagagac caagaaccat   1200
gatcattgcc tgctgaatcg gccagggcct ggccactctg tgaatacatg atcttgcaat   1260
gttgggttat tccagccaaa gacatttcaa gtgcctgtaa ctgatttgtc catatttata   1320
aacactgatc tggnaaaaaa aaaaaaaaa a                                    1351
```

```
<210> SEQ ID NO 42
<211> LENGTH: 314
<212> TYPE: PRT
<213> ORGANISM: Mus musculus
<220> FEATURE:
<221> NAME/KEY: UNSURE
<222> LOCATION: (306)
<220> FEATURE:
<221> NAME/KEY: UNSURE
<222> LOCATION: (310)

<400> SEQUENCE: 42

Met Phe Ser Ile Asn Pro Leu Glu Asn Leu Lys Leu Tyr Ile Ser Ser
 1               5                  10                  15

Arg Pro Pro Leu Val Phe Met Ile Ser Val Ser Ala Met Ala Ile
                20                  25                  30

Ala Phe Leu Thr Leu Gly Tyr Phe Lys Ile Lys Glu Ile Lys Ser
            35                  40                  45

Pro Glu Met Ala Glu Asp Trp Asn Thr Phe Leu Leu Arg Phe Asn Asp
 50                  55                  60

Leu Asp Leu Cys Val Ser Glu Asn Glu Thr Leu Lys His Leu Ser Asn
 65                  70                  75                  80

Asp Thr Thr Thr Pro Glu Ser Thr Met Thr Val Gly Gln Ala Arg Ser
                85                  90                  95

Ser Thr Gln Pro Pro Gln Ser Leu Glu Glu Ser Gly Pro Ile Asn Ile
                100                 105                 110

Ser Val Ala Ile Thr Leu Thr Leu Asp Pro Leu Lys Pro Phe Gly Gly
            115                 120                 125

Tyr Ser Arg Asn Val Thr His Leu Tyr Ser Thr Ile Leu Gly His Gln
130                 135                 140

Ile Gly Leu Ser Gly Arg Glu Ala His Glu Glu Ile Asn Ile Thr Phe
145                 150                 155                 160

Thr Leu Pro Ala Ala Trp Asn Ala Asp Asp Cys Ala Leu His Gly His
                165                 170                 175

Cys Glu Gln Ala Val Phe Thr Ala Cys Met Thr Leu Thr Ala Ala Pro
            180                 185                 190

Gly Val Phe Pro Val Thr Val Gln Pro Pro His Cys Ile Pro Asp Thr
        195                 200                 205

Tyr Ser Asn Ala Thr Leu Trp Tyr Lys Ile Phe Thr Thr Ala Arg Asp
210                 215                 220

Ala Asn Thr Lys Tyr Ala Gln Asp Tyr Asn Pro Phe Trp Cys Tyr Lys
225                 230                 235                 240

Gly Ala Ile Gly Lys Val Tyr His Ala Leu Asn Pro Lys Leu Thr Val
                245                 250                 255

Val Val Pro Asp Asp Asp Arg Ser Leu Ile Asn Leu His Leu Met His
            260                 265                 270

Thr Ser Tyr Phe Leu Phe Val Met Val Ile Thr Met Phe Cys Tyr Ala
        275                 280                 285

Val Ile Lys Gly Arg Pro Ser Lys Leu Arg Gln Ser Asn Pro Glu Phe
    290                 295                 300

Cys Xaa Glu Lys Val Xaa Leu Ala Asp Ala
305                 310

<210> SEQ ID NO 43
<211> LENGTH: 848
<212> TYPE: DNA
<213> ORGANISM: Mus musculus
<220> FEATURE:
```

<221> NAME/KEY: unsure
<222> LOCATION: (11)
<220> FEATURE:
<221> NAME/KEY: unsure
<222> LOCATION: (30)
<220> FEATURE:
<221> NAME/KEY: unsure
<222> LOCATION: (137)
<220> FEATURE:
<221> NAME/KEY: unsure
<222> LOCATION: (183)
<220> FEATURE:
<221> NAME/KEY: unsure
<222> LOCATION: (370)
<220> FEATURE:
<221> NAME/KEY: unsure
<222> LOCATION: (649)
<220> FEATURE:
<221> NAME/KEY: unsure
<222> LOCATION: (712)
<220> FEATURE:
<221> NAME/KEY: unsure
<222> LOCATION: (725)
<220> FEATURE:
<221> NAME/KEY: unsure
<222> LOCATION: (727)
<220> FEATURE:
<221> NAME/KEY: unsure
<222> LOCATION: (729)
<220> FEATURE:
<221> NAME/KEY: unsure
<222> LOCATION: (746)
<220> FEATURE:
<221> NAME/KEY: unsure
<222> LOCATION: (760)
<220> FEATURE:
<221> NAME/KEY: unsure
<222> LOCATION: (840)

<400> SEQUENCE: 43

```
agctgttggg ntcgcggttg aggacaaatn ttcgcggtct ttccagtatt cttggatcgg    60
aaacccgtcg gcttccgaac ggtactccgc caccgaggga cctgagcgag tccgcatcga   120
ccggatcgga aaacctntcg actgttgggg tgagtactcc ctctcaaaag cgggcatgac   180
ttntgcgcta agattgtcag tttccaaaaa cgaggaggat ttgatattca cctggcccgc   240
ggtgatgcct ttgagggtgg ccgcgtccat ctggtcagaa aagacaatct ttttgttgtc   300
aagcttgagg tgtggcaggc ttgagatctg gccatacact tgagtgacaa tgacatccac   360
tttgcctttn tctccacagg tgtccactcc caggtccaac tgcagacttc gaattcggcc   420
aaagaggcct actttcatat ccacgatgcg ttttctggcc gccacgatcc tgctgctggc   480
gctggtcgct gccagccagg cggagcccct gcacttcaag gactgcggct ctaaggtggg   540
agttataaag gaggtgaatg tgagcccatg tcccaccgat ccctgtcagc tgcacaaagg   600
ccagtcctac agtgtcaaca tcacctttac cagcggcact cagtcccana acagcacggc   660
cttggtccac ggcatcctgg aagggatccg ggtccccttc cctattcctg ancctgacgg   720
ttgtnanant ggaatcaact gccccntcca gaaagacaan gtctacagct acctgaataa   780
gcttccggtg aaaaatgaat acccctctat aaaactggtg gtggaatgga aactttgaan   840
atgacaaa                                                             848
```

<210> SEQ ID NO 44
<211> LENGTH: 130
<212> TYPE: PRT
<213> ORGANISM: Mus musculus
<220> FEATURE:
<221> NAME/KEY: UNSURE
<222> LOCATION: (68)

```
<220> FEATURE:
<221> NAME/KEY: UNSURE
<222> LOCATION: (89)
<220> FEATURE:
<221> NAME/KEY: UNSURE
<222> LOCATION: (94)..(95)
<220> FEATURE:
<221> NAME/KEY: UNSURE
<222> LOCATION: (101)
<220> FEATURE:
<221> NAME/KEY: UNSURE
<222> LOCATION: (105)

<400> SEQUENCE: 44
```

| Met | Arg | Phe | Leu | Ala | Ala | Thr | Ile | Leu | Leu | Leu | Ala | Leu | Val | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Gln | Ala | Glu | Pro | Leu | His | Phe | Lys | Asp | Cys | Gly | Ser | Lys | Val | Gly |
|     |     |     | 20  |     |     |     |     | 25  |     |     |     |     | 30  |     |     |

| Val | Ile | Lys | Glu | Val | Asn | Val | Ser | Pro | Cys | Pro | Thr | Asp | Pro | Cys | Gln |
|     |     |     | 35  |     |     |     |     | 40  |     |     |     |     | 45  |     |     |

| Leu | His | Lys | Gly | Gln | Ser | Tyr | Ser | Val | Asn | Ile | Thr | Phe | Thr | Ser | Gly |
|     |     | 50  |     |     |     |     | 55  |     |     |     |     | 60  |     |     |     |

| Thr | Gln | Ser | Xaa | Asn | Ser | Thr | Ala | Leu | Val | His | Gly | Ile | Leu | Glu | Gly |
| 65  |     |     |     |     | 70  |     |     |     |     | 75  |     |     |     |     | 80  |

| Ile | Arg | Val | Pro | Phe | Pro | Ile | Pro | Xaa | Pro | Asp | Gly | Cys | Xaa | Xaa | Gly |
|     |     |     |     | 85  |     |     |     |     | 90  |     |     |     |     | 95  |     |

| Ile | Asn | Cys | Pro | Xaa | Gln | Lys | Asp | Xaa | Val | Tyr | Ser | Tyr | Leu | Asn | Lys |
|     |     |     | 100 |     |     |     |     | 105 |     |     |     |     | 110 |     |     |

| Leu | Pro | Val | Lys | Asn | Glu | Tyr | Pro | Ser | Ile | Lys | Leu | Val | Val | Glu | Trp |
|     |     |     | 115 |     |     |     |     | 120 |     |     |     |     | 125 |     |     |

| Lys | Leu |
|     | 130 |

```
<210> SEQ ID NO 45
<211> LENGTH: 265
<212> TYPE: DNA
<213> ORGANISM: Mus musculus
<220> FEATURE:
<221> NAME/KEY: unsure
<222> LOCATION: (2)
<220> FEATURE:
<221> NAME/KEY: unsure
<222> LOCATION: (67)
<220> FEATURE:
<221> NAME/KEY: unsure
<222> LOCATION: (75)
<220> FEATURE:
<221> NAME/KEY: unsure
<222> LOCATION: (79)
<220> FEATURE:
<221> NAME/KEY: unsure
<222> LOCATION: (101)
<220> FEATURE:
<221> NAME/KEY: unsure
<222> LOCATION: (104)
<220> FEATURE:
<221> NAME/KEY: unsure
<222> LOCATION: (111)
<220> FEATURE:
<221> NAME/KEY: unsure
<222> LOCATION: (121)
<220> FEATURE:
<221> NAME/KEY: unsure
<222> LOCATION: (133)
<220> FEATURE:
<221> NAME/KEY: unsure
<222> LOCATION: (136)
<220> FEATURE:
<221> NAME/KEY: unsure
```

```
<222> LOCATION: (157)
<220> FEATURE:
<221> NAME/KEY: unsure
<222> LOCATION: (162)
<220> FEATURE:
<221> NAME/KEY: unsure
<222> LOCATION: (164)
<220> FEATURE:
<221> NAME/KEY: unsure
<222> LOCATION: (172)
<220> FEATURE:
<221> NAME/KEY: unsure
<222> LOCATION: (175)
<220> FEATURE:
<221> NAME/KEY: unsure
<222> LOCATION: (183)
<220> FEATURE:
<221> NAME/KEY: unsure
<222> LOCATION: (187)
<220> FEATURE:
<221> NAME/KEY: unsure
<222> LOCATION: (192)
<220> FEATURE:
<221> NAME/KEY: unsure
<222> LOCATION: (199)..(200)
<220> FEATURE:
<221> NAME/KEY: unsure
<222> LOCATION: (208)
<220> FEATURE:
<221> NAME/KEY: unsure
<222> LOCATION: (211)
<220> FEATURE:
<221> NAME/KEY: unsure
<222> LOCATION: (223)
<220> FEATURE:
<221> NAME/KEY: unsure
<222> LOCATION: (225)
<220> FEATURE:
<221> NAME/KEY: unsure
<222> LOCATION: (227)
<220> FEATURE:
<221> NAME/KEY: unsure
<222> LOCATION: (243)..(244)
<220> FEATURE:
<221> NAME/KEY: unsure
<222> LOCATION: (246)

<400> SEQUENCE: 45
gngttacctc ccctgtttct aagtgcctcc tgagtcccca gcccctggct tatcagtcag      60
atgagtntcc ttggnagcnt ctgccccatc gcttcagcag nagngactag ntttcctcgg     120
natccagact ggntgnggg cagtctgccg cagaaanttg tntntgagtg gntgngtctt     180
tgnggtnagc tntcgttcnn tggtagtntt nattaaagcc aanantnggt tgcaaaaaaa     240
aanngnaaaa aaaaaaaaaa aaaaa                                          265

<210> SEQ ID NO 46
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 46
tnagatccaa cagtcacgtt cacgaaacc                                       29

<210> SEQ ID NO 47
<211> LENGTH: 29
<212> TYPE: DNA
```

```
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 47
cntcctggtt gttgtttgaa gagcaggcg                                              29

<210> SEQ ID NO 48
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 48
tngcccaaga aactgggttt cacatttaa                                              29

<210> SEQ ID NO 49
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 49
gntgaagcat gcccaatttc atttcctct                                              29

<210> SEQ ID NO 50
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 50
antgttctct ggcttgtcag ggaagactg                                              29

<210> SEQ ID NO 51
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 51
tncaagttga gttgtacaga agcccaaga                                              29

<210> SEQ ID NO 52
<211> LENGTH: 29
```

```
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 52
gntgtgagaa gaccactcgg tgatgacct                              29

<210> SEQ ID NO 53
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 53
tngagtctgg gtggtagaca aatcatgca                              29

<210> SEQ ID NO 54
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 54
anggacggta tatatcacca tgaacaagt                              29

<210> SEQ ID NO 55
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 55
anaggcagga ggagacggga ttgatggtt                              29

<210> SEQ ID NO 56
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 56
anaagcgtca tgcagagcca tgatgaggg                              29

<210> SEQ ID NO 57
```

```
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 57
anaaatgtag caggcttggc ttgcagcag                                              29

<210> SEQ ID NO 58
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 58
angacccatt tccagtccaa atctttgac                                              29

<210> SEQ ID NO 59
<211> LENGTH: 28
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 59
gncaaggtgt ctgtaggaga aactatat                                               28

<210> SEQ ID NO 60
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 60
anccagggct atacagagaa accctgtct                                              29

<210> SEQ ID NO 61
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 61
gntcttgaag aagtagccca gggtgagga                                              29
```

-continued

```
<210> SEQ ID NO 62
<211> LENGTH: 29
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (2)
<223> OTHER INFORMATION: biotinylated phosphoaramidite residue

<400> SEQUENCE: 62
cnggtaaagg tgatgttgac actgtagga                                29
```

US 6,312,921 B1

SECRETED PROTEINS AND POLYNUCLEOTIDES ENCODING THEM

This application is a continuation-in-part of application Ser. No. 09/080,478, filed May 18, 1998 (abandoned), which is a continuation-in-part of application Ser. No. 08/976,110, filed Nov. 21, 1997 (abandoned), which is a continuation-in-part of application Ser. No. 08/686,878, filed Jul. 26, 1996, now U.S. Pat. No. 5,708,157. This application is also a continuation-in-part of application Ser. No. 08/702,081, filed Aug. 23, 1996 (abandoned), application Ser. No. 08/721,489, filed Sep. 27, 1996, now U.S. Pat. No. 5,786,465, and application Ser. No. 08/721,924, filed Sep. 27, 1996, now U.S. Pat. No. 5,969,125, each of which are continuation-in-part applications of parent application Ser. No. 08/686,878, now U.S. Pat. No. 5,708,157. All of such applications are incorporated by reference herein.

SUMMARY OF THE INVENTION

In one embodiment, the present invention provides a composition comprising an isolated polynucleotide selected from the group consisting of:
   (a) a polynucleotide comprising the nucleotide sequence of SEQ ID NO:1;
   (b) a polynucleotide comprising the nucleotide sequence of SEQ ID NO:1 from nucleotide 44 to nucleotide 1204;
   (c) a polynucleotide comprising the nucleotide sequence of SEQ ID NO:1 from nucleotide 1 to nucleotide 403;
   (d) a polynucleotide comprising the nucleotide sequence of the full-length protein coding sequence of clone AJ26_3 deposited under accession number ATCC 98115;
   (e) a polynucleotide encoding the full-length protein encoded by the cDNA insert of clone AJ26_3 deposited under accession number ATCC 98115;
   (f) a polynucleotide comprising the nucleotide sequence of the mature protein coding sequence of clone AJ26_3 deposited under accession number ATCC 98115;
   (g) a polynucleotide encoding the mature protein encoded by the cDNA insert of clone AJ26_3 deposited under accession number ATCC 98115;
   (h) a polynucleotide encoding a protein comprising the amino acid sequence of SEQ ID NO:2;
   (i) a polynucleotide encoding a protein comprising a fragment of the amino acid sequence of SEQ ID NO:2 having biological activity;
   (j) a polynucleotide which is an allelic variant of a polynucleotide of (a)–(g) above;
   (k) a polynucleotide which encodes a species homologue of the protein of (h) or (i) above; and
   (l) a polynucleotide capable of hybridizing under stringent conditions to any one of the polynucleotides specified in (a)–(i).

Preferably, such polynucleotide comprises the nucleotide sequence of SEQ ID NO:1 from nucleotide 44 to nucleotide 1204; the nucleotide sequence of SEQ ID NO:1 from nucleotide 1 to nucleotide 403; the nucleotide sequence of the full-length protein coding sequence of clone AJ26_3 deposited under accession number ATCC 98115; or the nucleotide sequence of the mature protein coding sequence of clone AJ26_3 deposited under accession number ATCC 98115. In other preferred embodiments, the polynucleotide encodes the full-length or mature protein encoded by the cDNA insert of clone AJ26_3 deposited under accession number ATCC 98115. In yet other preferred embodiments, the present invention provides a polynucleotide encoding a protein comprising the amino acid sequence of SEQ ID NO:2 from amino acid 1 to amino acid 120.

Other embodiments provide the gene corresponding to the cDNA sequence of SEQ ID NO:1.

In other embodiments, the present invention provides a composition comprising a protein, wherein said protein comprises an amino acid sequence selected from the group consisting of:
   (a) the amino acid sequence of SEQ ID NO:2;
   (b) the amino acid sequence of SEQ ID NO:2 from amino acid 1 to amino acid 120;
   (c) fragments of the amino acid sequence of SEQ ID NO:2; and
   (d) the amino acid sequence encoded by the cDNA insert of clone AJ26_3 deposited under accession number ATCC 98115;
the protein being substantially free from other mammalian proteins. Preferably such protein comprises the amino acid sequence of SEQ ID NO:2 or the amino acid sequence of SEQ ID NO:2 from amino acid 1 to amino acid 120.

In one embodiment, the present invention provides a composition comprising an isolated polynucleotide selected from the group consisting of:
   (a) a polynucleotide comprising the nucleotide sequence of SEQ ID NO:3;
   (b) a polynucleotide comprising the nucleotide sequence of SEQ ID NO:3 from nucleotide 928 to nucleotide 2541;
   (c) a polynucleotide comprising the nucleotide sequence of SEQ ID NO:3 from nucleotide 988 to nucleotide 2541;
   (d) a polynucleotide comprising the nucleotide sequence of SEQ ID NO:3 from nucleotide 684 to nucleotide 1128;
   (e) a polynucleotide comprising the nucleotide sequence of the full-length protein coding sequence of clone AJ172_2 deposited under accession number ATCC 98115;
   (f) a polynucleotide encoding the full-length protein encoded by the cDNA insert of clone AJ172_2 deposited under accession number ATCC 98115;
   (g) a polynucleotide comprising the nucleotide sequence of the mature protein coding sequence of clone AJ172_2 deposited under accession number ATCC 98115;
   (h) a polynucleotide encoding the mature protein encoded by the cDNA insert of clone AJ172_2 deposited under accession number ATCC 98115;
   (i) a polynucleotide encoding a protein comprising the amino acid sequence of SEQ ID NO:4;
   (j) a polynucleotide encoding a protein comprising a fragment of the amino acid sequence of SEQ ID NO:4 having biological activity;
   (k) a polynucleotide which is an allelic variant of a polynucleotide of (a)–(h) above;
   (l) a polynucleotide which encodes a species homologue of the protein of (i) or (j) above; and
   (m) a polynucleotide capable of hybridizing under stringent conditions to any one of the polynucleotides specified in (a)–(j).

Preferably, such polynucleotide comprises the nucleotide sequence of SEQ ID NO:3 from nucleotide 928 to nucleotide 2541; the nucleotide sequence of SEQ ID NO:3 from nucleotide 988 to nucleotide 2541; the nucleotide sequence of SEQ ID NO:3 from nucleotide 684 to nucleotide 1128; the nucleotide sequence of the full-length protein coding sequence of clone AJ172_2 deposited under accession number ATCC 98115; or the nucleotide sequence of the mature protein coding sequence of clone AJ172_2 deposited under accession number ATCC 98115. In other preferred embodiments, the polynucleotide encodes the full-length or mature protein encoded by the cDNA insert of clone AJ172_2 deposited under accession number ATCC 98115. In yet other preferred embodiments, the present invention provides a polynucleotide encoding a protein comprising the amino acid sequence of SEQ ID NO:4 from amino acid 1 to amino acid 67.

Other embodiments provide the gene corresponding to the cDNA sequence of SEQ ID NO:3.

In other embodiments, the present invention provides a composition comprising a protein, wherein said protein comprises an amino acid sequence selected from the group consisting of:
(a) the amino acid sequence of SEQ ID NO:4;
(b) the amino acid sequence of SEQ ID NO:4 from amino acid 1 to amino acid 67;
(c) fragments of the amino acid sequence of SEQ ID NO:4; and
(d) the amino acid sequence encoded by the cDNA insert of clone AJ172_2 deposited under accession number ATCC 98115;
the protein being substantially free from other mammalian proteins. Preferably such protein comprises the amino acid sequence of SEQ ID NO:4 or the amino acid sequence of SEQ ID NO:4 from amino acid 1 to amino acid 67.

In one embodiment, the present invention provides a composition comprising an isolated polynucleotide selected from the group consisting of:
(a) a polynucleotide comprising the nucleotide sequence of SEQ ID NO:6;
(b) a polynucleotide comprising the nucleotide sequence of SEQ ID NO:6 from nucleotide 185 to nucleotide 385;
(c) a polynucleotide comprising the nucleotide sequence of the full-length protein coding sequence of clone AP224_2 deposited under accession number ATCC 98115;
(d) a polynucleotide encoding the full-length protein encoded by the cDNA insert of clone AP224_2 deposited under accession number ATCC 98115;
(e) a polynucleotide comprising the nucleotide sequence of the mature protein coding sequence of clone AP224_2 deposited under accession number ATCC 98115;
(f) a polynucleotide encoding the mature protein encoded by the cDNA insert of clone AP224_2 deposited under accession number ATCC 98115;
(g) a polynucleotide encoding a protein comprising the amino acid sequence of SEQ ID NO:7;
(h) a polynucleotide encoding a protein comprising a fragment of the amino acid sequence of SEQ ID NO:7 having biological activity;
(i) a polynucleotide which is an allelic variant of a polynucleotide of (a)–(f) above;
(j) a polynucleotide which encodes a species homologue of the protein of (g) or (h) above; and
(k) a polynucleotide capable of hybridizing under stringent conditions to any one of the polynucleotides specified in (a)–(h).

Preferably, such polynucleotide comprises the nucleotide sequence of SEQ ID NO:6 from nucleotide 185 to nucleotide 385; the nucleotide sequence of the full-length protein coding sequence of clone AP224_2 deposited under accession number ATCC 98115; or the nucleotide sequence of the mature protein coding sequence of clone AP224_2 deposited under accession number ATCC 98115. In other preferred embodiments, the polynucleotide encodes the full-length or mature protein encoded by the cDNA insert of clone AP224_2 deposited under accession number ATCC 98115. In yet other preferred embodiments, the present invention provides a polynucleotide encoding a protein comprising the amino acid sequence of SEQ ID NO:7 from amino acid 1 to amino acid 28.

Other embodiments provide the gene corresponding to the cDNA sequence of SEQ ID NO:6, SEQ ID NO:5 or SEQ ID NO:8.

In other embodiments, the present invention provides a composition comprising a protein, wherein said protein comprises an amino acid sequence selected from the group consisting of:
(a) the amino acid sequence of SEQ ID NO:7;
(b) the amino acid sequence of SEQ ID NO:7 from amino acid 1 to amino acid 28;
(c) fragments of the amino acid sequence of SEQ ID NO:7; and
(d) the amino acid sequence encoded by the cDNA insert of clone AP224_2 deposited under accession number ATCC 98115;
the protein being substantially free from other mammalian proteins. Preferably such protein comprises the amino acid sequence of SEQ ID NO:7 or the amino acid sequence of SEQ ID NO:7 from amino acid 1 to amino acid 28.

In one embodiment, the present invention provides a composition comprising an isolated polynucleotide selected from the group consisting of:
(a) a polynucleotide comprising the nucleotide sequence of SEQ ID NO:9;
(b) a polynucleotide comprising the nucleotide sequence of SEQ ID NO:9 from nucleotide 6 to nucleotide 2408;
(c) a polynucleotide comprising the nucleotide sequence of SEQ ID NO:9 from nucleotide 1295 to nucleotide 1705;
(d) a polynucleotide comprising the nucleotide sequence of the full-length protein coding sequence of clone BL89_13 deposited under accession number ATCC 98153;
(e) a polynucleotide encoding the full-length protein encoded by the cDNA insert of clone BL89_13 deposited under accession number ATCC 98153;
(f) a polynucleotide comprising the nucleotide sequence of the mature protein coding sequence of clone BL89_13 deposited under accession number ATCC 98153;
(g) a polynucleotide encoding the mature protein encoded by the cDNA insert of clone BL89_13 deposited under accession number ATCC 98153;
(h) a polynucleotide encoding a protein comprising the amino acid sequence of SEQ ID NO:10;
(i) a polynucleotide encoding a protein comprising a fragment of the amino acid sequence of SEQ ID NO:10 having biological activity;
(j) a polynucleotide which is an allelic variant of a polynucleotide of (a)–(g) above;
(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:9 from nucleotide 6 to nucleotide 2408; the nucleotide sequence of SEQ ID NO:9 from nucleotide 1295 to nucleotide 1705; the nucleotide sequence of the full-length protein coding sequence of clone BL89__13 deposited under accession number ATCC 98153; or the nucleotide sequence of the mature protein coding sequence of clone BL89__13 deposited under accession number ATCC 98153. In other preferred embodiments, the polynucleotide encodes the full-length or mature protein encoded by the cDNA insert of clone BL89__13 deposited under accession number ATCC 98153. In yet other preferred embodiments, the present invention provides a polynucleotide encoding a protein comprising the amino acid sequence of SEQ ID NO:10 from amino acid 431 to amino acid 567.

Other embodiments provide the gene corresponding to the cDNA sequence of SEQ ID NO:9.

In other embodiments, the present invention provides a composition comprising a protein, wherein said protein comprises an amino acid sequence selected from the group consisting of:

(a) the amino acid sequence of SEQ ID NO:10;
(b) the amino acid sequence of SEQ ID NO:10 from amino acid 431 to amino acid 567;
(c) fragments of the amino acid sequence of SEQ ID NO:10; and
(d) the amino acid sequence encoded by the cDNA insert of clone BL89__13 deposited under accession number ATCC 98153;

the protein being substantially free from other mammalian proteins. Preferably such protein comprises the amino acid sequence of SEQ ID NO:10 or the amino acid sequence of SEQ ID NO:10 from amino acid 431 to amino acid 567.

In one embodiment, the present invention provides a composition comprising an isolated polynucleotide selected from the group consisting of:

(a) a polynucleotide comprising the nucleotide sequence of SEQ ID NO:11;
(b) a polynucleotide comprising the nucleotide sequence of SEQ ID NO:11; from nucleotide 2113 to nucleotide 2337;
(c) a polynucleotide comprising the nucleotide sequence of SEQ ID NO:11 from nucleotide 2036 to nucleotide 2316;
(d) a polynucleotide comprising the nucleotide sequence of the full-length protein coding sequence of clone BL341__4 deposited under accession number ATCC 98115;
(e) a polynucleotide encoding the full-length protein encoded by the cDNA insert of clone BL341__4 deposited under accession number ATCC 98115;
(f) a polynucleotide comprising the nucleotide sequence of the mature protein coding sequence of clone BL341__4 deposited under accession number ATCC 98115;
(g) a polynucleotide encoding the mature protein encoded by the cDNA insert of clone BL341__4 deposited under accession number ATCC 98115;
(h) a polynucleotide encoding a protein comprising the amino acid sequence of SEQ ID NO:12;
(i) a polynucleotide encoding a protein comprising a fragment of the amino acid sequence of SEQ ID NO:12 having biological activity;
(j) a polynucleotide which is an allelic variant of a polynucleotide of (a)–(g) above;
(k) a polynucleotide which encodes a species homologue of the protein of (h) or (i) above; and
(l) a polynucleotide capable of hybridizing under stringent conditions to any one of the polynucleotides specified in (a)–(i).

Preferably, such polynucleotide comprises the nucleotide sequence of SEQ ID NO:11 from nucleotide 2113 to nucleotide 2337; the nucleotide sequence of SEQ ID NO:11 from nucleotide 2036 to nucleotide 2316; the nucleotide sequence of the full-length protein coding sequence of clone BL341__4 deposited under accession number ATCC 98115; or the nucleotide sequence of the mature protein coding sequence of clone BL341__4 deposited under accession number ATCC 98115. In other preferred embodiments, the polynucleotide encodes the full-length or mature protein encoded by the cDNA insert of clone BL341__4 deposited under accession number ATCC 98115. In yet other preferred embodiments, the present invention provides a polynucleotide encoding a protein comprising the amino acid sequence of SEQ ID NO:12 from amino acid 1 to amino acid 68.

Other embodiments provide the gene corresponding to the cDNA sequence of SEQ ID NO:11.

In other embodiments, the present invention provides a composition comprising a protein, wherein said protein comprises an amino acid sequence selected from the group consisting of:

(a) the amino acid sequence of SEQ ID NO:12;
(b) the amino acid sequence of SEQ ID NO:12 from amino acid 1 to amino acid 68;
(c) fragments of the amino acid sequence of SEQ ID NO:12; and
(d) the amino acid sequence encoded by the cDNA insert of clone BL341__4 deposited under accession number ATCC 98115;

the protein being substantially free from other mammalian proteins. Preferably such protein comprises the amino acid sequence of SEQ ID NO:12 or the amino acid sequence of SEQ ID NO:12 from amino acid 1 to amino acid 68.

In one embodiment, the present invention provides a composition comprising an isolated polynucleotide selected from the group consisting of:

(a) a polynucleotide comprising the nucleotide sequence of SEQ ID NO:13;
(b) a polynucleotide comprising the nucleotide sequence of SEQ ID NO:13 from nucleotide 1 to nucleotide 390;
(c) a polynucleotide comprising the nucleotide sequence of the full-length protein coding sequence of clone BV239__3 deposited under accession number ATCC 98153;
(d) a polynucleotide encoding the full-length protein encoded by the cDNA insert of clone BV239_3 deposited under accession number ATCC 98153;
(e) a polynucleotide comprising the nucleotide sequence of the mature protein coding sequence of clone BV239__3 deposited under accession number ATCC 98153;
(f) a polynucleotide encoding the mature protein encoded by the cDNA insert of clone BV239__3 deposited under accession number ATCC 98153;
(g) a polynucleotide encoding a protein comprising the amino acid sequence of SEQ ID NO:14;
(h) a polynucleotide encoding a protein comprising a fragment of the amino acid sequence of SEQ ID NO:14 having biological activity;

(i) a polynucleotide which is an allelic variant of a polynucleotide of (a)–(f) above;

(j) a polynucleotide which encodes a species homologue of the protein of (g) or (h) above; and (k) a polynucleotide capable of hybridizing under stringent conditions to any one of the polynucleotides specified in (a)–(h).

Preferably, such polynucleotide comprises the nucleotide sequence of SEQ ID NO:13 from nucleotide 1 to nucleotide 390; the nucleotide sequence of the full-length protein coding sequence of clone BV239_3 deposited under accession number ATCC 98153; or the nucleotide sequence of the mature protein coding sequence of clone BV239_3 deposited under accession number ATCC 98153. In other preferred embodiments, the polynucleotide encodes the full-length or mature protein encoded by the cDNA insert of clone BV239_3 deposited under accession number ATCC 98153. In yet other preferred embodiments, the present invention provides a polynucleotide encoding a protein comprising the amino acid sequence of SEQ ID NO:14 from amino acid 50 to amino acid 130.

Other embodiments provide the gene corresponding to the cDNA sequence of SEQ ID NO:13.

In other embodiments, the present invention provides a composition comprising a protein, wherein said protein comprises an amino acid sequence selected from the group consisting of:

(a) the amino acid sequence of SEQ ID NO:14;

(b) the amino acid sequence of SEQ ID NO:14 from amino acid 50 to amino acid 130;

(c) fragments of the amino acid sequence of SEQ ID NO:14; and (d) the amino acid sequence encoded by the cDNA insert of clone BV239_3 deposited under accession number ATCC 98153;

the protein being substantially free from other mammalian proteins. Preferably such protein comprises the amino acid sequence of SEQ ID NO:14 or the amino acid sequence of SEQ ID NO:14 from amino acid 50 to amino acid 130.

In one embodiment, the present invention provides a composition comprising an isolated polynucleotide selected from the group consisting of:

(a) a polynucleotide comprising the nucleotide sequence of SEQ ID NO:15;

(b) a polynucleotide comprising the nucleotide sequence of SEQ ID NO:15 from nucleotide 144 to nucleotide 257;

(c) a polynucleotide comprising the nucleotide sequence of SEQ ID NO:15 from nucleotide 30 to nucleotide 271;

(d) a polynucleotide comprising the nucleotide sequence of the full-length protein coding sequence of clone CC25_17 deposited under accession number ATCC 98153;

(e) a polynucleotide encoding the full-length protein encoded by the cDNA insert of clone CC25_17 deposited under accession number ATCC 98153;

(f) a polynucleotide comprising the nucleotide sequence of the mature protein coding sequence of clone CC25_17 deposited under accession number ATCC 98153;

(g) a polynucleotide encoding the mature protein encoded by the cDNA insert of clone CC25_17 deposited under accession number ATCC 98153;

(h) a polynucleotide encoding a protein comprising the amino acid sequence of SEQ ID NO:16;

(i) a polynucleotide encoding a protein comprising a fragment of the amino acid sequence of SEQ ID NO:16 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:15 from nucleotide 144 to nucleotide 257; the nucleotide sequence of SEQ ID NO:15 from nucleotide 30 to nucleotide 271; the nucleotide sequence of the full-length protein coding sequence of clone CC25_17 deposited under accession number ATCC 98153; or the nucleotide sequence of the mature protein coding sequence of clone CC25_17 deposited under accession number ATCC 98153. In other preferred embodiments, the polynucleotide encodes the full-length or mature protein encoded by the cDNA insert of clone CC25_17 deposited under accession number ATCC 98153.

Other embodiments provide the gene corresponding to the cDNA sequence of SEQ ID NO:15.

In other embodiments, the present invention provides a composition comprising a protein, wherein said protein comprises an amino acid sequence selected from the group consisting of:

(a) the amino acid sequence of SEQ ID NO:16;

(b) fragments of the amino acid sequence of SEQ ID NO:16; and (c) the amino acid sequence encoded by the cDNA insert of clone CC25_17 deposited under accession number ATCC 98153;

the protein being substantially free from other mammalian proteins. Preferably such protein comprises the amino acid sequence of SEQ ID NO:16.

In one embodiment, the present invention provides a composition comprising an isolated polynucleotide selected from the group consisting of:

(a) a polynucleotide comprising the nucleotide sequence of SEQ ID NO:17;

(b) a polynucleotide comprising the nucleotide sequence of SEQ ID NO:17 from nucleotide 431 to nucleotide 520;

(c) a polynucleotide comprising the nucleotide sequence of SEQ ID NO:17 from nucleotide 266 to nucleotide 511;

(d) a polynucleotide comprising the nucleotide sequence of the full-length protein coding sequence of clone CC397_19 deposited under accession number ATCC 98153;

(e) a polynucleotide encoding the full-length protein encoded by the cDNA insert of clone CC397_19 deposited under accession number ATCC 98153;

(f) a polynucleotide comprising the nucleotide sequence of the mature protein coding sequence of clone CC397_19 deposited under accession number ATCC 98153;

(g) a polynucleotide encoding the mature protein encoded by the cDNA insert of clone CC397_19 deposited under accession number ATCC 98153;

(h) a polynucleotide encoding a protein comprising the amino acid sequence of SEQ ID NO:18;

(i) a polynucleotide encoding a protein comprising a fragment of the amino acid sequence of SEQ ID NO:18 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:17 from nucleotide 431 to nucleotide 520; the nucleotide sequence of SEQ ID NO:17 from nucleotide 266 to nucleotide 511; the nucleotide sequence of the full-length protein coding sequence of clone CC397_19 deposited under accession number ATCC 98153; or the nucleotide sequence of the mature protein coding sequence of clone CC397_19 deposited under accession number ATCC 98153. In other preferred embodiments, the polynucleotide encodes the full-length or mature protein encoded by the cDNA insert of clone CC397_19 deposited under accession number ATCC 98153. In yet other preferred embodiments, the present invention provides a polynucleotide encoding a protein comprising the amino acid sequence of SEQ ID NO:18 from amino acid 1 to amino acid 27.

Other embodiments provide the gene corresponding to the cDNA sequence of SEQ ID NO:17.

In other embodiments, the present invention provides a composition comprising a protein, wherein said protein comprises an amino acid sequence selected from the group consisting of:

(a) the amino acid sequence of SEQ ID NO:18;

(b) the amino acid sequence of SEQ ID NO:18 from amino acid 1 to amino acid 27;

(c) fragments of the amino acid sequence of SEQ ID NO:18; and (d) the amino acid sequence encoded by the cDNA insert of clone CC397_19 deposited under accession number ATCC 98153;

the protein being substantially free from other mammalian proteins. Preferably such protein comprises the amino acid sequence of SEQ ID NO:18 or the amino acid sequence of SEQ ID NO:18 from amino acid 1 to amino acid 27.

In one embodiment, the present invention provides a composition comprising an isolate polynucleotide selected from the group consisting of:

(a) a polynucleotide comprising the nucleotide sequence of SEQ ID NO:20;

(b) a polynucleotide comprising the nucleotide sequence of SEQ ID NO:20 from nucleotide 253 to nucleotide 519;

(c) a polynucleotide comprising the nucleotide sequence of SEQ ID NO:20 from nucleotide 298 to nucleotide 519;

(d) a polynucleotide comprising the nucleotide sequence of the full-length protein coding sequence of clone D305_2 deposited under accession number ATCC 98115;

(e) a polynucleotide encoding the full-length protein encoded by the cDNA insert of clone D305_2 deposited under accession number ATCC 98115;

(f) a polynucleotide comprising the nucleotide sequence of the mature protein coding sequence of clone D305_2 deposited under accession number ATCC 98115;

(g) a polynucleotide encoding the mature protein encoded by the cDNA insert of clone D305_2 deposited under accession number ATCC 98115;

(h) a polynucleotide encoding a protein comprising the amino acid sequence of SEQ ID NO:21;

(i) a polynucleotide encoding a protein comprising a fragment of the amino acid sequence of SEQ ID NO:21 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:20 from nucleotide 253 to nucleotide 519; the nucleotide sequence of SEQ ID NO:20 from nucleotide 298 to nucleotide 519; the nucleotide sequence of the full-length protein coding sequence of clone D305_2 deposited under accession number ATCC 98115; or the nucleotide sequence of the mature protein coding sequence of clone D305_2 deposited under accession number ATCC 98115. In other preferred embodiments, the polynucleotide encodes the full-length or mature protein encoded by the cDNA insert of clone D305_2 deposited under accession number ATCC 98115.

Other embodiments provide the gene corresponding to the cDNA sequence of SEQ ID NO:20, SEQ ID NO:19 or SEQ ID NO:22.

In other embodiments, the present invention provides a composition comprising a protein, wherein said protein comprises an amino acid sequence selected from the group consisting of:

(a) the amino acid sequence of SEQ ID NO:21;

(b) fragments of the amino acid sequence of SEQ ID NO:21; and (c) the amino acid sequence encoded by the cDNA insert of clone D305_2 deposited under accession number ATCC 98115;

the protein being substantially free from other mammalian proteins. Preferably such protein comprises the amino acid sequence of SEQ ID NO:21.

In one embodiment, the present invention provides a composition comprising an isolated polynucleotide selected from the group consisting of:

(a) a polynucleotide comprising the nucleotide sequence of SEQ ID NO:23;

(b) a polynucleotide comprising the nucleotide sequence of SEQ ID NO:23 from nucleotide 194 to nucleotide 622;

(c) a polynucleotide comprising the nucleotide sequence of SEQ ID NO:23 from nucleotide 524 to nucleotide 622;

(d) a polynucleotide comprising the nucleotide sequence of the full-length protein coding sequence of clone G55_1 deposited under accession number ATCC 98115;

(e) a polynucleotide encoding the full-length protein encoded by the cDNA insert of clone G55_1 deposited under accession number ATCC 98115;

(f) a polynucleotide comprising the nucleotide sequence of the mature protein coding sequence of clone G55_1 deposited under accession number ATCC 98115;

(g) a polynucleotide encoding the mature protein encoded by the cDNA insert of clone G55_1 deposited under accession number ATCC 98115;

(h) a polynucleotide encoding a protein comprising the amino acid sequence of SEQ ID NO:24;

(i) a polynucleotide encoding a protein comprising a fragment of the amino acid sequence of SEQ ID NO:24 having biological activity;
(j) a polynucleotide which is an allelic variant of a polynucleotide of (a)–(g) above;
(k) a polynucleotide which encodes a species homologue of the protein of (h) or (i) above; and
(l) a polynucleotide capable of hybridizing under stringent conditions to any one of the polynucleotides specified in (a)–(i).

Preferably, such polynucleotide comprises the nucleotide sequence of SEQ ID NO:23 from nucleotide 194 to nucleotide 622; the nucleotide sequence of SEQ ID NO:23 from nucleotide 524 to nucleotide 622; the nucleotide sequence of the full-length protein coding sequence of clone G55_1 deposited under accession number ATCC 98115; or the nucleotide sequence of the mature protein coding sequence of clone G55_1 deposited under accession number ATCC 98115. In other preferred embodiments, the polynucleotide encodes the full-length or mature protein encoded by the cDNA insert of clone G55_1 deposited under accession number ATCC 98115. In yet other preferred embodiments, the present invention provides a polynucleotide encoding a protein comprising the amino acid sequence of SEQ ID NO:24 from amino acid 1 to amino acid 32.

Other embodiments provide the gene corresponding to the cDNA sequence of SEQ ID NO:23 or SEQ ID NO:25.

In other embodiments, the present invention provides a composition comprising a protein, wherein said protein comprises an amino acid sequence selected from the group consisting of:

(a) the amino acid sequence of SEQ ID NO:24;
(b) the amino acid sequence of SEQ ID NO:24 from amino acid 1 to amino acid 32;
(c) fragments of the amino acid sequence of SEQ ID NO:24; and
(d) the amino acid sequence encoded by the cDNA insert of clone G55_1 deposited under accession number ATCC 98115;

the protein being substantially free from other mammalian proteins. Preferably such protein comprises the amino acid sequence of SEQ ID NO:24 or the amino acid sequence of SEQ ID NO:24 from amino acid 1 to amino acid 32.

In one embodiment, the present invention provides a composition comprising an isolated polynucleotide selected from the group consisting of:

(a) a polynucleotide comprising the nucleotide sequence of SEQ ID NO:26;
(b) a polynucleotide comprising the nucleotide sequence of SEQ ID NO:26 from nucleotide 402 to nucleotide 533;
(c) a polynucleotide comprising the nucleotide sequence of SEQ ID NO:26 from nucleotide 447 to nucleotide 533;
(d) a polynucleotide comprising the nucleotide sequence of the full-length protein coding sequence of clone K39_7 deposited under accession number ATCC 98115;
(e) a polynucleotide encoding the full-length protein encoded by the cDNA insert of clone K39_7 deposited under accession number ATCC 98115;
(f) a polynucleotide comprising the nucleotide sequence of the mature protein coding sequence of clone K39_7 deposited under accession number ATCC 98115;
(g) a polynucleotide encoding the mature protein encoded by the cDNA insert of clone K39_7 deposited under accession number ATCC 98115;
(h) a polynucleotide encoding a protein comprising the amino acid sequence of SEQ ID NO:27;
(i) a polynucleotide encoding a protein comprising a fragment of the amino acid sequence of SEQ ID NO:27 having biological activity;
(j) a polynucleotide which is an allelic variant of a polynucleotide of (a)–(g) above;
(k) a polynucleotide which encodes a species homologue of the protein of (h) or (i) above; and
(l) a polynucleotide capable of hybridizing under stringent conditions to any one of the polynucleotides specified in (a)–(i).

Preferably, such polynucleotide comprises the nucleotide sequence of SEQ ID NO:26 from nucleotide 402 to nucleotide 533; the nucleotide sequence of SEQ ID NO:26 from nucleotide 447 to nucleotide 533; the nucleotide sequence of the full-length protein coding sequence of clone K39_7 deposited under accession number ATCC 98115; or the nucleotide sequence of the mature protein coding sequence of clone K39_7 deposited under accession number ATCC 98115. In other preferred embodiments, the polynucleotide encodes the full-length or mature protein encoded by the cDNA insert of clone K39_7 deposited under accession number ATCC 98115.

Other embodiments provide the gene corresponding to the cDNA sequence of SEQ ID NO:26 or SEQ ID NO:28.

In other embodiments, the present invention provides a composition comprising a protein, wherein said protein comprises an amino acid sequence selected from the group consisting of:

(a) the amino acid sequence of SEQ ID NO:27;
(b) fragments of the amino acid sequence of SEQ ID NO:27; and
(c) the amino acid sequence encoded by the cDNA insert of clone K39_7 deposited under accession number ATCC 98115;

the protein being substantially free from other mammalian proteins. Preferably such protein comprises the amino acid sequence of SEQ ID NO:27.

In one embodiment, the present invention provides a composition comprising an isolated polynucleotide selected from the group consisting of:

(a) a polynucleotide comprising the nucleotide sequence of SEQ ID NO:29;
(b) a polynucleotide comprising the nucleotide sequence of SEQ ID NO:29 from nucleotide 241 to nucleotide 525;
(c) a polynucleotide comprising the nucleotide sequence of the full-length protein coding sequence of clone K330_3 deposited under accession number ATCC 98115;
(d) a polynucleotide encoding the full-length protein encoded by the cDNA insert of clone K330_3 deposited under accession number ATCC 98115;
(e) a polynucleotide comprising the nucleotide sequence of the mature protein coding sequence of clone K330_3 deposited under accession number ATCC 98115;
(f) a polynucleotide encoding the mature protein encoded by the cDNA insert of clone K330_3 deposited under accession number ATCC 98115;
(g) a polynucleotide encoding a protein comprising the amino acid sequence of SEQ ID NO:30;
(h) a polynucleotide encoding a protein comprising a fragment of the amino acid sequence of SEQ ID NO:30 having biological activity;

(i) a polynucleotide which is an allelic variant of a polynucleotide of (a)–(f) above;
(j) a polynucleotide which encodes a species homologue of the protein of (g) or (h) above; and
(k) a polynucleotide capable of hybridizing under stringent conditions to any one of the polynucleotides specified in (a)–(h).

Preferably, such polynucleotide comprises the nucleotide sequence of SEQ ID NO:29 from nucleotide 241 to nucleotide 525; the nucleotide sequence of the full-length protein coding sequence of clone K330_3 deposited under accession number ATCC 98115; or the nucleotide sequence of the mature protein coding sequence of clone K330_3 deposited under accession number ATCC 98115. In other preferred embodiments, the polynucleotide encodes the full-length or mature protein encoded by the cDNA insert of clone K330_3 deposited under accession number ATCC 98115. In yet other preferred embodiments, the present invention provides a polynucleotide encoding a protein comprising the amino acid sequence of SEQ ID NO:30 from amino acid 1 to amino acid 35.

Other embodiments provide the gene corresponding to the cDNA sequence of SEQ ID NO:29 or SEQ ID NO:31.

In other embodiments, the present invention provides a composition comprising a protein, wherein said protein comprises an amino acid sequence selected from the group consisting of:
(a) the amino acid sequence of SEQ ID NO:30;
(b) the amino acid sequence of SEQ ID NO:30 from amino acid 1 to amino acid 35;
(c) fragments of the amino acid sequence of SEQ ID NO:30; and
(d) the amino acid sequence encoded by the cDNA insert of clone K330_3 deposited under accession number ATCC 98115;
the protein being substantially free from other mammalian proteins. Preferably such protein comprises the amino acid sequence of SEQ ID NO:30 or the amino acid sequence of SEQ ID NO:30 from amino acid 1 to amino acid 35.

In one embodiment, the present invention provides a composition comprising an isolated polynucleotide selected from the group consisting of:
(a) a polynucleotide comprising the nucleotide sequence of SEQ ID NO:32;
(b) a polynucleotide comprising the nucleotide sequence of SEQ ID NO:32 from nucleotide 158 to nucleotide 571;
(c) a polynucleotide comprising the nucleotide sequence of the full-length protein coding sequence of clone K363_3 deposited under accession number ATCC 98115;
(d) a polynucleotide encoding the full-length protein encoded by the cDNA insert of clone K363_3 deposited under accession number ATCC 98115;
(e) a polynucleotide comprising the nucleotide sequence of the mature protein coding sequence of clone K363_3 deposited under accession number ATCC 98115;
(f) a polynucleotide encoding the mature protein encoded by the cDNA insert of clone K363_3 deposited under accession number ATCC 98115;
(g) a polynucleotide encoding a protein comprising the amino acid sequence of SEQ ID NO:33;
(h) a polynucleotide encoding a protein comprising a fragment of the amino acid sequence of SEQ ID NO:33 having biological activity;

(i) a polynucleotide which is an allelic variant of a polynucleotide of (a)–(f) above;
(j) a polynucleotide which encodes a species homologue of the protein of (g) or (h) above; and
(k) a polynucleotide capable of hybridizing under stringent conditions to any one of the polynucleotides specified in (a)–(h).

Preferably, such polynucleotide comprises the nucleotide sequence of SEQ ID NO:32 from nucleotide 158 to nucleotide 571; the nucleotide sequence of the full-length protein coding sequence of clone K363_3 deposited under accession number ATCC 98115; or the nucleotide sequence of the mature protein coding sequence of clone K363_3 deposited under accession number ATCC 98115. In other preferred embodiments, the polynucleotide encodes the full-length or mature protein encoded by the cDNA insert of clone K363_3 deposited under accession number ATCC 98115. In yet other preferred embodiments, the present invention provides a polynucleotide encoding a protein comprising the amino acid sequence of SEQ ID NO:33 from amino acid 24 to amino acid 96.

Other embodiments provide the gene corresponding to the cDNA sequence of SEQ ID NO:32 or SEQ ID NO:34.

In other embodiments, the present invention provides a composition comprising a protein, wherein said protein comprises an amino acid sequence selected from the group consisting of:
(a) the amino acid sequence of SEQ ID NO:33;
(b) the amino acid sequence of SEQ ID NO:33 from amino acid 24 to amino acid 96;
(c) fragments of the amino acid sequence of SEQ ID NO:33; and
(d) the amino acid sequence encoded by the cDNA insert of clone K363_3 deposited under accession number ATCC 98115;
the protein being substantially free from other mammalian proteins. Preferably such protein comprises the amino acid sequence of SEQ ID NO:33 or the amino acid sequence of SEQ ID NO:33 from amino acid 24 to amino acid 96.

In one embodiment, the present invention provides a composition comprising an isolated polynucleotide selected from the group consisting of:
(a) a polynucleotide comprising the nucleotide sequence of SEQ ID NO:35;
(b) a polynucleotide comprising the nucleotide sequence of SEQ ID NO:35 from nucleotide 401 to nucleotide 526;
(c) a polynucleotide comprising the nucleotide sequence of the full-length protein coding sequence of clone K446_3 deposited under accession number ATCC 98115;
(d) a polynucleotide encoding the full-length protein encoded by the cDNA insert of clone K446_3 deposited under accession number ATCC 98115;
(e) a polynucleotide comprising the nucleotide sequence of the mature protein coding sequence of clone K446_3 deposited under accession number ATCC 98115;
(f) a polynucleotide encoding the mature protein encoded by the cDNA insert of clone K446_3 deposited under accession number ATCC 98115;
(g) a polynucleotide encoding a protein comprising the amino acid sequence of SEQ ID NO:36;
(h) a polynucleotide encoding a protein comprising a fragment of the amino acid sequence of SEQ ID NO:36 having biological activity;

(i) a polynucleotide which is an allelic variant of a polynucleotide of (a)–(f) above;
(j) a polynucleotide which encodes a species homologue of the protein of (g) or (h) above; and
(k) a polynucleotide capable of hybridizing under stringent conditions to any one of the polynucleotides specified in (a)–(h).

Preferably, such polynucleotide comprises the nucleotide sequence of SEQ ID NO:35 from nucleotide 401 to nucleotide 526; the nucleotide sequence of the full-length protein coding sequence of clone K446_3 deposited under accession number ATCC 98115; or the nucleotide sequence of the mature protein coding sequence of clone K446_3 deposited under accession number ATCC 98115. In other preferred embodiments, the polynucleotide encodes the full-length or mature protein encoded by the cDNA insert of clone K446_3 deposited under accession number ATCC 98115.

Other embodiments provide the gene corresponding to the cDNA sequence of SEQ ID NO:35 or SEQ ID NO:37.

In other embodiments, the present invention provides a composition comprising a protein, wherein said protein comprises an amino acid sequence selected from the group consisting of:
  (a) the amino acid sequence of SEQ ID NO:36;
  (b) fragments of the amino acid sequence of SEQ ID NO:36; and
  (c) the amino acid sequence encoded by the cDNA insert of clone K446_3 deposited under accession number ATCC 98115;
the protein being substantially free from other mammalian proteins. Preferably such protein comprises the amino acid sequence of SEQ ID NO:36.

In one embodiment, the present invention provides a composition comprising an isolated polynucleotide selected from the group consisting of:
  (a) a polynucleotide comprising the nucleotide sequence of SEQ ID NO:38;
  (b) a polynucleotide comprising the nucleotide sequence of SEQ ID NO:38 from nucleotide 380 to nucleotide 535;
  (c) a polynucleotide comprising the nucleotide sequence of the full-length protein coding sequence of clone K464_4 deposited under accession number ATCC 98115;
  (d) a polynucleotide encoding the full-length protein encoded by the cDNA insert of clone K464_4 deposited under accession number ATCC 98115;
  (e) a polynucleotide comprising the nucleotide sequence of the mature protein coding sequence of clone K464_4 deposited under accession number ATCC 98115;
  (f) a polynucleotide encoding the mature protein encoded by the cDNA insert of clone K464_4 deposited under accession number ATCC 98115;
  (g) a polynucleotide encoding a protein comprising the amino acid sequence of SEQ ID NO:39;
  (h) a polynucleotide encoding a protein comprising a fragment of the amino acid sequence of SEQ ID NO:39 having biological activity;
  (i) a polynucleotide which is an allelic variant of a polynucleotide of (a)–(f) above;
  (j) a polynucleotide which encodes a species homologue of the protein of (g) or (h) above; and
  (k) a polynucleotide capable of hybridizing under stringent conditions to any one of the polynucleotides specified in (a)–(h).

Preferably, such polynucleotide comprises the nucleotide sequence of SEQ ID NO:38 from nucleotide 380 to nucleotide 535; the nucleotide sequence of the full-length protein coding sequence of clone K464_4 deposited under accession number ATCC 98115; or the nucleotide sequence of the mature protein coding sequence of clone K464_4 deposited under accession number ATCC 98115. In other preferred embodiments, the polynucleotide encodes the full-length or mature protein encoded by the cDNA insert of clone K464_4 deposited under accession number ATCC 98115.

Other embodiments provide the gene corresponding to the cDNA sequence of SEQ ID NO:38 or SEQ ID NO:40.

In other embodiments, the present invention provides a composition comprising a protein, wherein said protein comprises an amino acid sequence selected from the group consisting of:
  (a) the amino acid sequence of SEQ ID NO:39;
  (b) fragments of the amino acid sequence of SEQ ID NO:39; and
  (c) the amino acid sequence encoded by the cDNA insert of clone K464_4 deposited under accession number ATCC 98115;
the protein being substantially free from other mammalian proteins. Preferably such protein comprises the amino acid sequence of SEQ ID NO:39.

In one embodiment, the present invention provides a composition comprising an isolated polynucleotide selected from the group consisting of:
  (a) a polynucleotide comprising the nucleotide sequence of SEQ ID NO:41;
  (b) a polynucleotide comprising the nucleotide sequence of SEQ ID NO:41 from nucleotide 218 to nucleotide 1159;
  (c) a polynucleotide comprising the nucleotide sequence of SEQ ID NO:41 from nucleotide 806 to nucleotide 1159;
  (d) a polynucleotide comprising the nucleotide sequence of SEQ ID NO:41 from nucleotide 217 to nucleotide 517;
  (e) a polynucleotide comprising the nucleotide sequence of the full-length protein coding sequence of clone K483_1 deposited under accession number ATCC 98115;
  (f) a polynucleotide encoding the full-length protein encoded by the cDNA insert of clone K483_1 deposited under accession number ATCC 98115;
  (g) a polynucleotide comprising the nucleotide sequence of the mature protein coding sequence of clone K483_1 deposited under accession number ATCC 98115;
  (h) a polynucleotide encoding the mature protein encoded by the cDNA insert of clone K483_1 deposited under accession number ATCC 98115;
  (i) a polynucleotide encoding a protein comprising the amino acid sequence of SEQ ID NO:42;
  (j) a polynucleotide encoding a protein comprising a fragment of the amino acid sequence of SEQ ID NO:42 having biological activity;
  (k) a polynucleotide which is an allelic variant of a polynucleotide of (a)–(h) above;
  (l) a polynucleotide which encodes a species homologue of the protein of (i) or (j) above; and
  (m) a polynucleotide capable of hybridizing under stringent conditions to any one of the polynucleotides specified in (a)–(j).

Preferably, such polynucleotide comprises the nucleotide sequence of SEQ ID NO:41 from nucleotide 218 to nucleotide 1159; the nucleotide sequence of SEQ ID NO:41 from nucleotide 806 to nucleotide 1159; the nucleotide sequence of SEQ ID NO:41 from nucleotide 217 to nucleotide 517; the nucleotide sequence of the full-length protein coding sequence of clone K483_1 deposited under accession number ATCC 98115; or the nucleotide sequence of the mature protein coding sequence of clone K483_1 deposited under accession number ATCC 98115. In other preferred embodiments, the polynucleotide encodes the full-length or mature protein encoded by the cDNA insert of clone K483_1 deposited under accession number ATCC 98115. In yet other preferred embodiments, the present invention provides a polynucleotide encoding a protein comprising the amino acid sequence of SEQ ID NO:42 from amino acid 1 to amino acid 100.

Other embodiments provide the gene corresponding to the cDNA sequence of SEQ ID NO:41.

In other embodiments, the present invention provides a composition comprising a protein, wherein said protein comprises an amino acid sequence selected from the group consisting of:

(a) the amino acid sequence of SEQ ID NO:42;

(b) the amino acid sequence of SEQ ID NO:42 from amino acid 1 to amino acid 100;

(c) fragments of the amino acid sequence of SEQ ID NO:42; and (d) the amino acid sequence encoded by the cDNA insert of clone K483_1 deposited under accession number ATCC 98115;

the protein being substantially free from other mammalian proteins. Preferably such protein comprises the amino acid sequence of SEQ ID NO:42 or the amino acid sequence of SEQ ID NO:42 from amino acid 1 to amino acid 100.

In one embodiment, the present invention provides a composition comprising an isolated polynucleotide selected from the group consisting of:

(a) a polynucleotide comprising the nucleotide sequence of SEQ ID NO:43;

(b) a polynucleotide comprising the nucleotide sequence of SEQ ID NO:43 from nucleotide 446 to nucleotide 835;

(c) a polynucleotide comprising the nucleotide sequence of SEQ ID NO:43 from nucleotide 503 to nucleotide 835;

(d) a polynucleotide comprising the nucleotide sequence of the full-length protein coding sequence of clone L69_3 deposited under accession number ATCC 98115;

(e) a polynucleotide encoding the full-length protein encoded by the cDNA insert of clone L69_3 deposited under accession number ATCC 98115;

(f) a polynucleotide comprising the nucleotide sequence of the mature protein coding sequence of clone L69_3 deposited under accession number ATCC 98115;

(g) a polynucleotide encoding the mature protein encoded by the cDNA insert of clone L69_3 deposited under accession number ATCC 98115;

(h) a polynucleotide encoding a protein comprising the amino acid sequence of SEQ ID NO:44;

(i) a polynucleotide encoding a protein comprising a fragment of the amino acid sequence of SEQ ID NO:44 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:43 from nucleotide 446 to nucleotide 835; the nucleotide sequence of SEQ ID NO:43 from nucleotide 503 to nucleotide 835; the nucleotide sequence of the full-length protein coding sequence of clone L69_3 deposited under accession number ATCC 98115; or the nucleotide sequence of the mature protein coding sequence of clone L69_3 deposited under accession number ATCC 98115. In other preferred embodiments, the polynucleotide encodes the full-length or mature protein encoded by the cDNA insert of clone L69_3 deposited under accession number ATCC 98115. In yet other preferred embodiments, the present invention provides a polynucleotide encoding a protein comprising the amino acid sequence of SEQ ID NO:44 from amino acid 1 to amino acid 93.

Other embodiments provide the gene corresponding to the cDNA sequence of SEQ ID NO:43 or SEQ ID NO:45.

In other embodiments, the present invention provides a composition comprising a protein, wherein said protein comprises an amino acid sequence selected from the group consisting of:

(a) the amino acid sequence of SEQ ID NO:44;

(b) the amino acid sequence of SEQ ID NO:44 from amino acid 1 to amino acid 93;

(c) fragments of the amino acid sequence of SEQ ID NO:44; and (d) the amino acid sequence encoded by the cDNA insert of clone L69_3 deposited under accession number ATCC 98115;

the protein being substantially free from other mammalian proteins. Preferably such protein comprises the amino acid sequence of SEQ ID NO:44 or the amino acid sequence of SEQ ID NO:44 from amino acid 1 to amino acid 93.

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention. Preferred embodiments include those in which the protein produced by such process is a mature form of the protein.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

Also disclosed are methods of promoting cell-cell fusion. Such a method comprises contacting a first cell and a second cell, wherein said first cell expresses an AJ172_2 protein. AJ172_2 expression in the first cell can occur naturally or be the result of transfection with a polynucleotide encoding an AJ172_2 protein. Preferably, the first cell is transfected with a polynucleotide or gene described above. The first cell and second cell can be of the same type or of different types. In other embodiments, at least one of said first cell and said second cell are transfected to express an additional protein other than the AJ172_2 protein.

In yet other embodiments, a method of inhibiting cell-cell fusion between a first cell which expresses an AJ172_2 protein and a second cell is disclosed, wherein the method comprises contacting said first cell with an AJ172_2 protein antagonist. Preferably, the antagonist is selected from the group consisting of an antibody or antibody fragment directed to an AJ172_2 protein, an antisense polynucleotide directed to a polynucleotide expressing an AJ172_2 protein, a nucleotide aptamer directed to an AJ172_2 protein, a peptide aptamer directed to an AJ172_2 protein and a small molecule which blocks the fusion-inducing activity of an AJ172_2 protein. In other preferred embodiments, the first cell is a placental cell (such as a cytotrophoblast) and the second cell is a cell from the maternal uterine lining.

Other embodiments provide for a method of inhibiting blastocyst implantation, wherein the method comprises contacting a cell within said blastocyst which expresses an AJ172_2 protein with an AJ172_2 protein antagonist.

Yet other embodiments provide for a method of inhibiting trophoblast invasion, wherein the method comprises contacting a first cell which expresses an AJ172_2 protein with an AJ172_2 protein antagonist.

Further embodiments provide for a method of diagnosing or predicting the existence of a condition associated with disregulation of AH172_2 protein in a mammalian subject, such method comprising (a) determining a first level of expression of AJ172_2 protein in the subject, and (b) comparing such first level of expression to a second level of expression of AJ172_2 protein in one or more other mammalian subjects which do not have said condition. Preferably, the condition is selected from the group consisting of pre-eclampsia, placental pathology and cancer (including choriocarcinoma). In preferred embodiments, such first level of expression is determined in the serum of the subject, using an antibody or antibody fragment directed to AJ172_2 protein.

Other embodiments provide for a method of treating a neoplastic disease (including choriocarcinoma) in a mammalian subject, such method comprising administering to said subject a therapeutically effective amount of an agent which promotes the expression or function of AJ172_2.

Yet other embodiments provide for a method of inhibiting metastasis in a mammalian subject, such method comprising administering to the subject a therapeutically effective amount of an agent which inhibits the expression or function of AJ172_2.

BRIEF DESCRIPTION OF THE DRAWINGS

FIG. 1 schematically depicts vectors into which various clones of the invention are inserted.

FIG. 6 demonstrates that AJ172_2 can mediate fusion between cells of differing types and between a cell expressing AJ172_2 and a cell not expressing AJ172_2. HELA cells were transfected with a cDNA encoding a P-selectin glycoprotein ligand-1/Fc fusion protein (PSGL-Fc). COS cells were transfected with AJ172_2. Another batch of COS cells was transfected with AJ172_2 in reverse orientation. The transfected HELA cells were mixed with each type of COS cells. As shown in FIG. 6, mixture with the AJ172_2 transfected COS cells caused fusion with the HELA cells, resulting in multinucleate fusions. Mixture with the COS cells transfected with AJ172_2 in reverse orientation resulted in no fusion (mononucleate cells remained).

As shown in FIG. 7, the COS cells fused with the liposomes, took up the expression plasmid, and began expressing GFP.

FIGS. 11 and 12 present data which demonstrate that AJ172_2 is disregulated in pre-eclampsia (see Example 3).

FIGS. 13 and 14 present data which demonstrate activity of AJ172_2 in remodeling of extracellular matrices (see Example 4).

DETAILED DESCRIPTION

Isolated Proteins and Polynucleotides

Figure 1A:
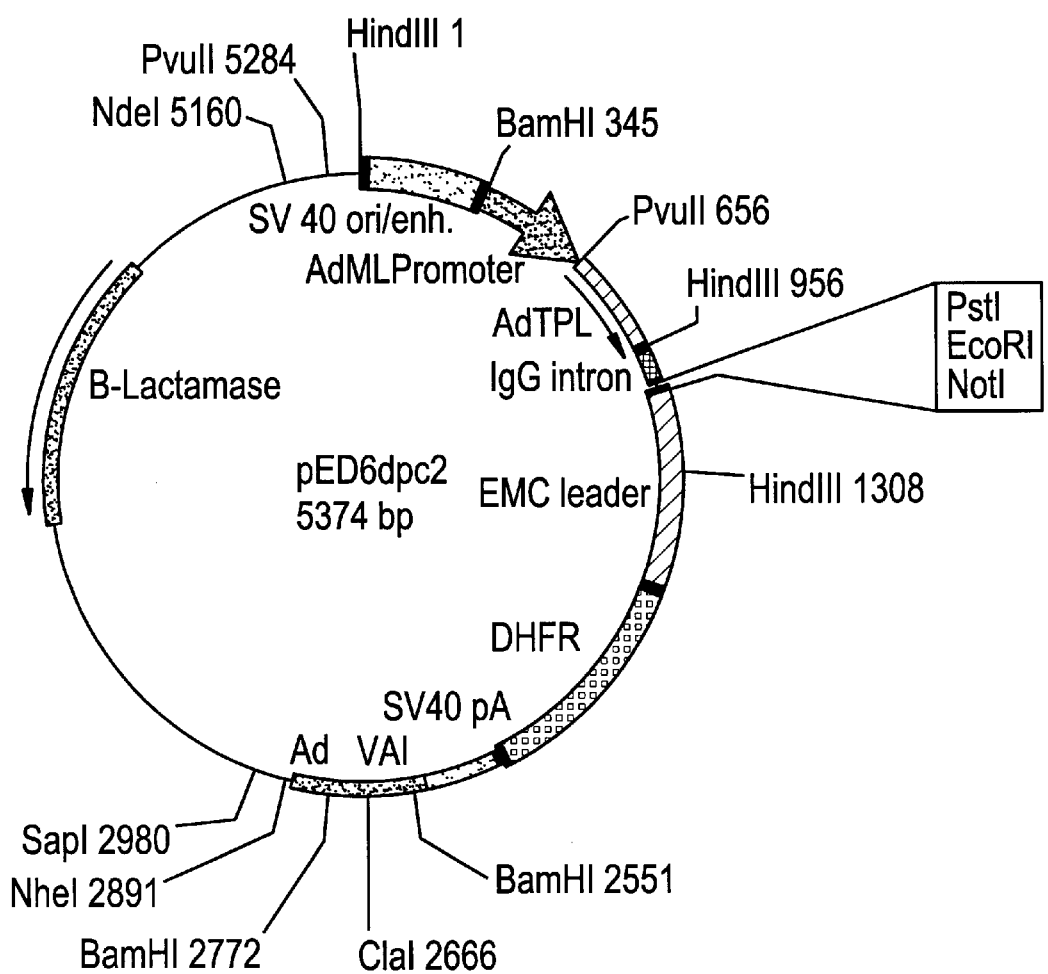
FIG. 1A depicts the vector pED6dpc2 and FIG. 1B depicts vector pNOTs.

Nucleotide and amino acid sequences, as presently determined, are reported below for each clone and protein disclosed in the present application. The nucleotide sequence of each clone can readily be determined by sequencing of the deposited clone in accordance with known methods. The predicted amino acid sequence (both full-length and mature) can then be determined from such nucleotide sequence. The amino acid sequence of the protein encoded by a particular clone can also be determined by expression of the clone in a suitable host cell, collecting the protein and determining its sequence. For each disclosed protein applicants have identified what they have determined to be the reading frame best identifiable with sequence information available at the time of filing.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "AJ26_3"

A polynucleotide of the present invention has been identified as clone "AJ26_3". AJ26_3 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. AJ26_3 is a full-length clone, including the entire coding sequence of a secreted protein (also referred to herein as "AJ26_3 protein").

The nucleotide sequence of AJ26_3 as presently determined is reported in SEQ ID NO:1. What applicants presently believe to be the proper reading frame and the predicted amino acid sequence of the AJ26_3 protein corresponding to the foregoing nucleotide sequence is reported in SEQ ID NO:2.

The EcoRI/NotI restriction fragment obtainable from the deposit containing clone AJ26_3 should be approximately 2100 bp.

The nucleotide sequence disclosed herein for AJ26_3 was searched against the GenBank and GeneSeq nucleotide sequence databases using BLASTN/BLASTX and FASTA search protocols. AJ26_3 demonstrated at least some similarity with sequences identified as U46493 (Cloning vector pFlp recombinase gene, complete cds). The predicted amino acid sequence disclosed herein for AJ26_3 was searched against the GenPept and GeneSeq amino acid sequence databases using the BLASTX search protocol. The predicted AJ26_3 protein demonstrated at least some similarity to sequences identified as J01917 (DNA polymerase [Human adenovirus type 2]), J01969 (DNA polymerase [Human adenovirus type 5]), L24893 (HUMAAC02_1 myelin protein zero [*Homo sapiens*]), U43330 (CTX [*Xenopus laevis*]), and U43394 (CTX [*Xenopus laevis*]). Based upon sequence similarity, AJ26_3 proteins and each similar protein or peptide may share at least some activity. The TopPredII computer program predicts four potential transmembrane domains within the AJ26_3 protein sequence, centered around amino acids 11, 41, 163, and 246 of SEQ ID NO:2. The AJ26_3 protein also has a possible signal sequence that could be cleaved to produce a mature protein starting at amino acid 17 of SEQ ID NO:2.

Clone "AJ172_2"

A polynucleotide of the present invention has been identified as clone "AJ172_2". AJ172_2 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. AJ172_2 is a full-length clone, including the entire coding sequence of a secreted protein (also referred to herein as "AJ172_2 protein").

The nucleotide sequence of AJ172_2 as presently determined is reported in SEQ ID NO:3. What applicants presently believe to be the proper reading frame and the predicted amino acid sequence of the AJ172_2 protein corresponding to the foregoing nucleotide sequence is reported in SEQ ID NO:4. Amino acids 8 to 20 are a predicted leader/signal sequence, with the predicted mature amino acid sequence beginning at amino acid 21, or are a transmembrane domain.

The EcoRI/NotI restriction fragment obtainable from the deposit containing clone AJ172_2 should be approximately 3000 bp.

The nucleotide sequence disclosed herein for AJ172_2 was searched against the GenBank and GeneSeq nucleotide sequence databases using BLASTN/BLASTX and FASTA search protocols. AJ172_2 demonstrated at least some similarity with sequences identified as AA077794 (7H01C09 Chromosome 7 HeLa cDNA Library *Homo sapiens* cDNA clone 7H01C09), AC000064 (Human BAC clone RG083M05 from 7q21–7q22, complete sequence), D78692 (Human placenta cDNA 5'-end GEN-503H08), H12439 (yj11h10.r1 *Homo sapiens* cDNA clone 148483 5'), R27389 (yh46a09.s1 *Homo sapiens* cDNA clone 132760 3'), and T09280 (Novel AMP/MCF virus clone 24 genome). The predicted amino acid sequence disclosed herein for AJ172_2 was searched against the GenPept and GeneSeq amino acid sequence databases using the BLASTX search protocol. The predicted AJ172_2 protein demonstrated at least some similarity to sequences identified as M26927 (pol polyprotein [Gibbon leukemia virus]), M93134 (pol protein [Friend murine leukemia virus]), and R75189 (Osteoinductive retrovirus RFB-14 pol gene product). AJ172_2 protein is similar to a number of viral env proteins, including those of baboon endogenous virus and many leukemia viruses, which associate with the membrane portion of the viral envelope. Based upon sequence similarity, AJ172_2 proteins and each similar protein or peptide may share at least some activity. The TopPredII computer program predicts five potential transmembrane domains within the AJ172_2 protein sequence, centered around amino acids 104, 267, 292, 328, and 457 of SEQ ID NO:4.

Clone "AP224_2"

A polynucleotide of the present invention has been identified as clone "AP224_2". AP224_2 was isolated from a human adult placenta cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. AP224_2 is a full-length clone, including the entire coding sequence of a secreted protein (also referred to herein as "AP224_2 protein").

The nucleotide sequence of the 5' portion of AP224_2 as presently determined is reported in SEQ ID NO:5. An additional internal nucleotide sequence from AP224_2 as presently determined is reported in SEQ ID NO:6. What applicants believe is the proper reading frame and the predicted amino acid sequence encoded by such internal sequence is reported in SEQ ID NO:7. Additional nucleotide sequence from the 3' portion of AP224_2, including the polyA tail, is reported in SEQ ID NO:8.

The EcoRI/NotI restriction fragment obtainable from the deposit containing clone AP224_2 should be approximately 2100 bp.

The nucleotide sequence disclosed herein for AP224_2 was searched against the GenBank and GeneSeq nucleotide sequence databases using BLASTN/BLASTX and FASTA search protocols. AP224_2 demonstrated at least some similarity with sequences identified as R37675 (yf61f08.s1 Homo sapiens cDNA clone 26687 3'). Based upon sequence similarity, AP224_2 proteins and each similar protein or peptide may share at least some activity.

Clone "BL89_13"

A polynucleotide of the present invention has been identified as clone "BL89_13". BL89_13 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. BL89_13 is a full-length clone, including the entire coding sequence of a secreted protein (also referred to herein as "BL89_13 protein").

The nucleotide sequence of BL89_13 as presently determined is reported in SEQ ID NO:9. What applicants presently believe to be the proper reading frame and the predicted amino acid sequence of the BL89_13 protein corresponding to the foregoing nucleotide sequence is reported in SEQ ID NO:10.

The EcoRI/NotI restriction fragment obtainable from the deposit containing clone BL89_13 should be approximately 3200 bp.

The nucleotide sequence disclosed herein for BL89_13 was searched against the GenBank and GeneSeq nucleotide sequence databases using BLASTN/BLASTX and FASTA search protocols. No hits were found in the database. The TopPredII computer program predicts a potential transmembrane domain within the BL89_13 protein sequence centered around amino acid 625 of SEQ ID NO:10.

Clone "BL341_4"

A polynucleotide of the present invention has been identified as clone "BL341_4". BL341_4 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. BL341_4 is a full-length clone, including the entire coding sequence of a secreted protein (also referred to herein as "BL341_4 protein").

The nucleotide sequence of BL341_4 as presently determined is reported in SEQ ID NO:11. What applicants presently believe to be the proper reading frame and the predicted amino acid sequence of the BL341_4 protein corresponding to the foregoing nucleotide sequence is reported in SEQ ID NO:12.

The EcoRI/NotI restriction fragment obtainable from the deposit containing clone BL341_4 should be approximately 2600 bp.

The nucleotide sequence disclosed herein for BL341_4 was searched against the GenBank and GeneSeq nucleotide sequence databases using BLASTN/BLASTX and FASTA search protocols. BL341_4 demonstrated at least some similarity with sequences identified as AA460103 (zx50a12.r1 Soares testis NHT *Homo sapiens* cDNA clone) and Z63359 (*H.sapiens* CpG island DNA genomic MseI fragment, clone 81e7, reverse read cpg81e7.rt1a). Based upon sequence similarity, BL341_4 proteins and each similar protein or peptide may share at least some activity.

Clone "BV239_3"

A polynucleotide of the present invention has been identified as clone "BV239_3". BV239_3 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. BV239_3 is a full-length clone, including the entire coding sequence of a secreted protein (also referred to herein as "BV239_3 protein").

The nucleotide sequence of BV239_3 as presently determined is reported in SEQ ID NO:13. What applicants presently believe to be the proper reading frame and the predicted amino acid sequence of the BV239_3 protein corresponding to the foregoing nucleotide sequence is reported in SEQ ID NO:14.

The EcoRI/NotI restriction fragment obtainable from the deposit containing clone BV239_3 should be approximately 310 bp.

The nucleotide sequence disclosed herein for BV239_3 was searched against the GenBank and GeneSeq nucleotide sequence databases using BLASTN/BLASTX and FASTA search protocols. BV239_3 demonstrated at least some similarity with sequences identified as U46493 (Cloning vector pFlp recombinase gene, complete cds). Based upon sequence similarity, BV239_3 proteins and each similar protein or peptide may share at least some activity.

Clone "CC25_17"

A polynucleotide of the present invention has been identified as clone "CC25_17". CC25_17 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CC25_17 is a full-length clone, including the entire coding sequence of a secreted protein (also referred to herein as "CC25_17 protein").

The nucleotide sequence of CC25_17 as presently determined is reported in SEQ ID NO:15. What applicants presently believe to be the proper reading frame and the predicted amino acid sequence of the CC25_17 protein corresponding to the foregoing nucleotide sequence is reported in SEQ ID NO:16.

The EcoRI/NotI restriction fragment obtainable from the deposit containing clone CC25_17 should be approximately 300 bp.

The nucleotide sequence disclosed herein for CC25_17 was searched against the GenBank and GeneSeq nucleotide sequence databases using BLASTN/BLASTX and FASTA search protocols. CC25_17 demonstrated at least some similarity with sequences identified as U46493 (Cloning vector pFlp recombinase gene, complete cds). Based upon sequence similarity, CC25_17 proteins and each similar protein or peptide may share at least some activity.

Clone "CC397_19"

A polynucleotide of the present invention has been identified as clone "CC397_19". CC397_19 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CC397_19 is a full-length clone, including the entire coding sequence of a secreted protein (also referred to herein as "CC397_19 protein").

The nucleotide sequence of CC397_19 as presently determined is reported in SEQ ID NO:17. What applicants presently believe to be the proper reading frame and the predicted amino acid sequence of the CC397_19 protein corresponding to the foregoing nucleotide sequence is reported in SEQ ID NO:18.

The EcoRI/NotI restriction fragment obtainable from the deposit containing clone CC397_19 should be approximately 1700 bp.

The nucleotide sequence disclosed herein for CC397_19 was searched against the GenBank and GeneSeq nucleotide sequence databases using BLASTN/IBLASTX and FASTA search protocols. CC397_19 demonstrated at least some similarity with sequences identified as AC002129 (Human DNA from chromsome 19 cosmid R33743, genomic sequence, complete sequence), D82019 (Mouse gene for basigin precursor, basigin signal precursor), G08688 (human STS CHLC.GATA29D08.P14592 clone GATA29D08), M68516 (Human protein C inhibitor gene, complete cds), and Z68756 (Human DNA sequence from cosmid L191F1, Huntington's Disease Region, chromosome 4p16.3 contains Huntington Disease (HD) gene, CpG island ESTs and U7 small nuclear RNA). The predicted amino acid sequence disclosed herein for CC397_19 was searched against the GenPept and GeneSeq amino acid sequence databases using the BLASTX search protocol. The predicted CC397_19 protein demonstrated at least some similarity to sequences identified as X52164 (Q300 protein (AA 1-77) [Mus musculus]). Based upon sequence similarity, CC397_19 proteins and each similar protein or peptide may share at least some activity. The nucleotide sequence of CC397_19 indicates that it may contain an Alu repetitive element.

Clone "D305_2"

A polynucleotide of the present invention has been identified as clone "D305_2". D305_2 was isolated from a human adult blood (peripheral blood mononuclear cells treated with concanavalin A and phorbol myristate acetate) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. D305_2 is a full-length clone, including the entire coding sequence of a secreted protein (also referred to herein as "D305_2 protein").

The nucleotide sequence of the 5' portion of D305_2 as presently determined is reported in SEQ ID NO:19. An additional internal nucleotide sequence from D305_2 as presently determined is reported in SEQ ID NO:20. What applicants believe is the proper reading frame and the predicted amino acid sequence encoded by such internal sequence is reported in SEQ ID NO:21. Amino acids 3 to 15 of SEQ ID NO:21 are a predicted leader/signal sequence, with the predicted mature amino acid sequence beginning at amino acid 16, or are a transmembrane domain. Additional nucleotide sequence from the 3' portion of D305_2, including the polyA tail, is reported in SEQ ID NO:22.

The EcoRI/NotI restriction fragment obtainable from the deposit containing clone D305_2 should be approximately 2400 bp.

The nucleotide sequence disclosed herein for D305_2 was searched against the GenBank and GeneSeq nucleotide sequence databases using BLASTN/BLASTX and FASTA search protocols. D305_2 demonstrated at least some similarity with sequences identified as AA055703 (z175d04.r1 Stratagene colon (#937204) *Homo sapiens* cDNA clone 510439 5'), N49593 (yy58d05.s1 *Homo sapiens* cDNA clone 277737 3'), R66646 (yi35b08.r1 *Homo sapiens* cDNA clone 141207 5' similar to SP P24A_YEAST P32802 P24A PROTEIN), U81006 (Human p76 mRNA, complete cds), and Z48758 (*S.cerevisiae* chromosome IV cosmid 9727). The predicted amino acid sequence disclosed herein for D305_2 was searched against the GenPept and GeneSeq amino acid sequence databases using the BLASTX search protocol. The predicted D305_2 protein demonstrated at least some similarity to sequences identified as U53880 (P24A protein (unknown function) (Swiss Prot. accession number P32802) [*Saccharomyces cerevisiae*]), U81006 (p76 [*Homo sapiens*]), X67316 (SCEMP70_1 p24a 70 kDa precursor [*Saccharomyces cerevisiae*]), and Z48758 (unknown [*Saccharomyces cerevisiae*]). Based upon sequence similarity, D305_2 proteins and each similar protein or peptide may share at least some activity.

Clone "G55_1"

A polynucleotide of the present invention has been identified as clone "G55_1". G55_1 was isolated from a human adult blood (peripheral blood mononuclear cells treated with concanavalin A and phorbol myristate acetate) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. G55_1 is a full-length clone, including the entire coding sequence of a secreted protein (also referred to herein as "G55_1 protein").

The nucleotide sequence of the 5' portion of G55_1 as presently determined is reported in SEQ ID NO:23. What applicants presently believe is the proper reading frame for the coding region is indicated in SEQ ID NO:24. The predicted amino acid sequence of the G55_1 protein corresponding to the foregoing nucleotide sequence is reported in SEQ ID NO:24. Amino acids 98 to 110 are a predicted leader/signal sequence, with the predicted mature amino acid sequence beginning at amino acid 111, or are a transmembrane domain. Additional nucleotide sequence from the 3' portion of G55_1, including the polyA tail, is reported in SEQ ID NO:25.

The EcoRI/NotI restriction fragment obtainable from the deposit containing clone G55_1 should be approximately 2000 bp.

The nucleotide sequence disclosed herein for G55_1 was searched against the GenBank and GeneSeq nucleotide sequence databases using BLASTN/BLASTX and FASTA search protocols. G55_1 demonstrated at least some similarity with sequences identified as R83586 (yp16a07.r1 *Homo sapiens* cDNA clone 187572 5'). Based upon sequence similarity, G55_1 proteins and each similar protein or peptide may share at least some activity.

Clone "K39_7"

A polynucleotide of the present invention has been identified as clone "K39_7". K39_7 was referred to as K39_2 in previous applications. K39_7 was isolated from a murine adult bone marrow (stromal cell line FCM-4) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. K39_7 is a full-length clone, including the entire coding sequence of a secreted protein (also referred to herein as "K39_7 protein").

The nucleotide sequence of the 5' portion of K39_7 as presently determined is reported in SEQ ID NO:26. What applicants presently believe is the proper reading frame for the coding region is indicated in SEQ ID NO:27. The predicted amino acid sequence of the K39_7 protein corresponding to the foregoing nucleotide sequence is reported in SEQ ID NO:27. Amino acids 3 to 15 are a predicted leader/signal sequence, with the predicted mature amino acid sequence beginning at amino acid 16, or are a transmembrane domain. Additional nucleotide sequence from the 3' portion of K39_7, including the polyA tail, is reported in SEQ ID NO:28.

The EcoRI/NotI restriction fragment obtainable from the deposit containing clone K39_7 should be approximately 1675 bp.

The nucleotide sequence disclosed herein for K39_7 was searched against the GenBank and GeneSeq nucleotide sequence databases using BLASTN/BLASTX and FASTA search protocols. K39_7 demonstrated at least some similarity with sequences identified as AA254326 (va15d06.r1 Soares mouse lymph node NbMLN Mus musculus cDNA clone 722987 5' similar to WP:C09G4.1 CE03978), D18935 (Mouse 3'-directed cDNA, MUSGSO1125, clone mc0564), H14129 (ym65b04.r1 *Homo sapiens* cDNA clone 163759 5'), and R20230 (hUOG-1, DNA segment encoding a mammalian GDF-1 protein). The predicted amino acid sequence disclosed herein for K39_7 was searched against the Gen- Pept and GeneSeq amino acid sequence databases using the BLASTX search protocol. The predicted K39_7 protein demonstrated at least some similarity to sequences identified as R86811 (*Saccharomyces cerevisiae* mutant LAG1 protein) and U42438 (similar to *S. cerevisiae* longevity-assurance protein 1 (SP P38703) [*Caenorhabditis elegans*]). Based upon sequence similarity, K39_7 proteins and each similar protein or peptide may share at least some activity.

Clone "K330_3"

A polynucleotide of the present invention has been identified as clone "K330_3". K330_3 was referred to as K330_2 in previous applications. K330_3 was isolated from a murine adult bone marrow (stromal cell line FCM-4) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. K330_3 is a full-length clone, including the entire coding sequence of a secreted protein (also referred to herein as "K330_3 protein").

The nucleotide sequence of the 5' portion of K330_3 as presently determined is reported in SEQ ID NO:29. What applicants presently believe is the proper reading frame for the coding region is indicated in SEQ ID NO:30. The predicted amino acid sequence of the K330_3 protein corresponding to the foregoing nucleotide sequence is reported in SEQ ID NO:30. Additional nucleotide sequence from the 3' portion of K330_3, including the polyA tail, is reported in SEQ ID NO:31.

The EcoRI/NotI restriction fragment obtainable from the deposit containing clone K330_3 should be approximately 1300 bp.

The nucleotide sequence disclosed herein for K330_3 was searched against the GenBank and GeneSeq nucleotide sequence databases using BLASTN/BLASTX and FASTA search protocols. K330_3 demonstrated at least some similarity with sequences identified as A03900 (*H.sapiens* HuV (NP) gene), AA038010 (mi80a11.r1 Soares mouse p3NMF19.5 Mus musculus cDNA clone 472892 5'), M30775 (Mouse thymidylate synthase pseudogene, 3' flank), R40824 (yf82c07.s1 *Homo sapiens* cDNA clone 28939 3'), T23245 (Human gene signature HUMGS05046), and U23512 (*Caenorhabditis elegans* cosmid M01G4). Based upon sequence similarity, K330_3 proteins and each similar protein or peptide may share at least some activity.

Clone "K363_3"

A polynucleotide of the present invention has been identified as clone "K363_3". K363_3 was referred to as K363_2 in previous applications. K363_3 was isolated from a murine adult bone marrow (stromal cell line FCM-4) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. K363_3 is a full-length clone, including the entire coding sequence of a secreted protein (also referred to herein as "K363_3 protein").

The nucleotide sequence of the 5' portion of K363_3 as presently determined is reported in SEQ ID NO:32. What applicants presently believe is the proper reading frame for the coding region is indicated in SEQ ID NO:33. The predicted amino acid sequence of the K363_3 protein corresponding to the foregoing nucleotide sequence is reported in SEQ ID NO:33. Additional nucleotide sequence from the 3' portion of K363_3, including the poly A tail, is reported in SEQ ID NO:34.

The EcoRI/NotI restriction fragment obtainable from the deposit containing clone K363_3 should be approximately 2690 bp.

The nucleotide sequence disclosed herein for K363_3 was searched against the GenBank and GeneSeq nucleotide sequence databases using BLASTN/BLASTX and FASTA search protocols. K363_3 demonstrated at least some similarity with sequences identified as AA437876 (vd20h06.s1 Knowles Solter mouse 2 cell Mus musculus cDNA clone 793115 5'), D21554 (Mouse embryonal carcinoma F9 cell cDNA, 67F09), and Y08460 (Mus musculus mRNA for Mdes transmembrane protein). The predicted amino acid sequence disclosed herein for K363_3 was searched against the GenPept and GeneSeq amino acid sequence databases using the BLASTX search protocol. The predicted K363_3 protein demonstrated at least some similarity to sequences identified as Y08460 (Mdes protein [Mus musculus]). Based upon sequence similarity, K363_3 proteins and each similar protein or peptide may share at least some activity.

Clone "K446_3"

A polynucleotide of the present invention has been identified as clone "K446_3". K446_3 was referred to as K446_2 in previous applications. K446_3 was isolated from a murine adult bone marrow (stromal cell line FCM-4) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. K446_3 is a full-length clone, including the entire coding sequence of a secreted protein (also referred to herein as "K446_3 protein").

The nucleotide sequence of the 5' portion of K446_3 as presently determined is reported in SEQ ID NO:35. What applicants presently believe is the proper reading frame for the coding region is indicated in SEQ ID NO:36. The predicted amino acid sequence of the K446_3 protein corresponding to the foregoing nucleotide sequence is reported in SEQ ID NO:36. Additional nucleotide sequence from the 3' portion of K446_3, including the polyA tail, is reported in SEQ ID NO:37.

The EcoRI/NotI restriction fragment obtainable from the deposit containing clone K446_3 should be approximately 2150 bp.

The nucleotide sequence disclosed herein for K446_3 was searched against the GenBank and GeneSeq nucleotide sequence databases using BLASTN/BLASTX and FASTA search protocols. No hits were found in the database.

Clone "K464_4"

A polynucleotide of the present invention has been identified as clone "K464_4". K464_4 was referred to as K464_3 in previous applications. K464_4 was isolated from a murine adult bone marrow (stromal cell line FCM-4) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. K464_4 is a full-length clone, including the entire coding sequence of a secreted protein (also referred to herein as "K464_4 protein").

The nucleotide sequence of the 5' portion of K464_4 as presently determined is reported in SEQ ID NO:38. What applicants presently believe is the proper reading frame for the coding region is indicated in SEQ ID NO:39. The predicted amino acid sequence of the K464_4 protein corresponding to the foregoing nucleotide sequence is reported in SEQ ID NO:39. Additional nucleotide sequence from the 3' portion of K464_4, including the poly A tail, is reported in SEQ ID NO:40.

The EcoRI/NotI restriction fragment obtainable from the deposit containing clone K464_4 should be approximately 1250 bp.

The nucleotide sequence disclosed herein for K464_4 was searched against the GenBank and GeneSeq nucleotide sequence databases using BLASTN/BLASTX and FASTA search protocols. K464_4 demonstrated at least some similarity with sequences identified as AA260484 (va95a09.r1 Soares mouse NML Mus musculus cDNA clone 747160 5'), AA419864 (vf49b08.r1 Soares mouse NbM), L25338 (Mus musculus folate-binding protein gene, 5' end), M22527 (Mouse cytotoxic T lymphocyte-specific serine protease), T01176 (P815A antigen precursor gene P1A), T21224 (Human gene signature HUMGS02538), T41900 (Vector pAPEX-3p), U46493 (Cloning vector pF1p recombinase gene, complete cds), U89673 (Cloning vector pIRES1neo, complete plasmid sequence), W32699 (zc06b11.s1 Soares parathyroid tumor NbHPA *Homo sapiens* cDNA clone 321501 3'), and W36926 (mb82b10.r1 Soares mouse p3NMF19.5 Mus musculus cDNA clone 335899 5'). The predicted amino acid sequence disclosed herein for K464_4 was searched against the GenPept and GeneSeq amino acid sequence databases using the BLASTX search protocol. The predicted K464_4 protein demonstrated at least some similarity to sequences identified as L33768 (JAK3 [Mus musculus]) and X16213 (MHC T7 class I antigen (64 AA) (119 is 2nd base in codon) [Mus musculus]). Based upon sequence similarity, K464_4 proteins and each similar protein or peptide may share at least some activity.

Clone "K483_1"

A polynucleotide of the present invention has been identified as clone "K483_1". K483_1 was isolated from a murine adult bone marrow (stromal cell line FCM-4) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. K483_1 is a full-length clone, including the entire coding sequence of a secreted protein (also referred to herein as "K483_1 protein").

The nucleotide sequence of K483_1 as presently determined is reported in SEQ ID NO:41. What applicants presently believe to be the proper reading frame and the predicted amino acid sequence of the K483_1 protein corresponding to the foregoing nucleotide sequence is reported in SEQ ID NO:42. Amino acids 184 to 196 are a predicted leader/signal sequence, with the predicted mature amino acid sequence beginning at amino acid 197, or are a transmembrane domain.

The EcoRI/NotI restriction fragment obtainable from the deposit containing clone K483_1 should be approximately 1500 bp.

The nucleotide sequence disclosed herein for K483_1 was searched against the GenBank and GeneSeq nucleotide sequence databases using BLASTN/BLASTX and FASTA search protocols. K483_1 demonstrated at least some similarity with sequences identified as AA 110914 (mm02c03.r1 Stratagene mouse kidney (#937315) Mus musculus cDNA clone 520324 5'), AA318160 (EST20431 Retina II *Homo sapiens* cDNA 5' end), AA500150 (vi97c09.r1 Barstead mouse pooled organs MPLRB4 Mus musculus cDNA clone 920176 5'), and N41895 (yw86b03.r1 *Homo sapiens* cDNA clone 259085 5'). Based upon sequence similarity, K483_1 proteins and each similar protein or peptide may share at least some activity. The TopPredII computer program predicts three potential transmembrane domains within the K483_1 protein sequence, centered around amino acids 18, 179, and 270 of SEQ ID NO:42. The K483_1 protein also has a possible signal sequence that could be cleaved to produce a mature protein starting at amino acid 34 of SEQ ID NO:42.

Clone "L69_3"

A polynucleotide of the present invention has been identified as clone "L69_3". L69_3 was referred to as L69_2 in previous applications. L69_3 was isolated from a murine adult thymus cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. L69_3 is a full-length clone, including the entire coding sequence of a secreted protein (also referred to herein as "L69_3 protein").

The nucleotide sequence of the 5' portion of L69_3 as presently determined is reported in SEQ ID NO:43. What applicants presently believe is the proper reading frame for the coding region is indicated in SEQ ID NO:44. The predicted amino acid sequence of the L69_3 protein corresponding to the foregoing nucleotide sequence is reported in SEQ ID NO:44. Amino acids 7 to 19 are a predicted leader/signal sequence, with the predicted mature amino acid sequence beginning at amino acid 20, or are a transmembrane domain. Additional nucleotide sequence from the 3' portion of L69_3, including the polyA tail, is reported in SEQ ID NO:45.

The EcoRI/NotI restriction fragment obtainable from the deposit containing clone L69_3 should be approximately 1200 bp.

The nucleotide sequence disclosed herein for L69_3 was searched against the GenBank and GeneSeq nucleotide sequence databases using BLASTN/BLASTX and FASTA search protocols. L69_3 demonstrated at least some similarity with sequences identified as H35162 (EST108034 Rattus sp. cDNA similar to *H.sapiens* hypothetical protein (PIR:S25641)), U02442 (Cloning vector pADbeta, complete sequence), W74864 (md91b10.r1 Soares mouse embryo NbME13.5 14.5 Mus musculus cDNA), and X67698 (*H.sapiens* tissue specific mRNA). The predicted amino acid sequence disclosed herein for L69_3 was searched against the GenPept and GeneSeq amino acid sequence databases using the BLASTX search protocol. The predicted L69_3 protein demonstrated at least some similarity to sequences identified as A18921 (tissue-specific secretory protein [unidentified]). Based upon sequence similarity, L69_3 proteins and each similar protein or peptide may share at least some activity.

Deposit of Clones

Clones $AJ26_{13}3$, $AJ172_{13}$ 2, AP224_2, BL89_10, BL341_4, BV239_2, CC25_16, $CC397_{13}11$, D305_2, G55_1, K39_7, K330_3, K363_ 3, K446_3, K464_4, K483_1, and L69_3 were deposited on Jul. 25, 1996 with the American Type Culture Collection as an original deposit under Budapest Treaty and were given the accession number ATCC 98115, from which each clone comprising a particular polynucleotide is obtainable. Clones K39_7, K330_3, K363_3, K446_3, K464_4, and L69_3 were referred to as K39_2, K330_2, K363_2, K446_2, K464_3, and L69_2, respectively, when the Jul. 25, 1996 deposit was made. An additional isolate of each of clones BL89_10, BV239_2, CC25_16, and CC397_11 (namely isolates BL89_13, BV239_3, CC25_ 17, and CC397_19, respectively) were deposited with the American Type Culture Collection at 10801 University Boulevard, Manassass, Va., 20110-2209, USA, on Aug. 23, 1996 under accession number 98153, from which each clone comprising a particular polynucleotide is obtainable. All restrictions on the availability to the public of the deposited material will be irrevocably removed upon the granting of the patent, except for the requirements specified in 37 C.F.R. §1.808(b).

Figure 1B:
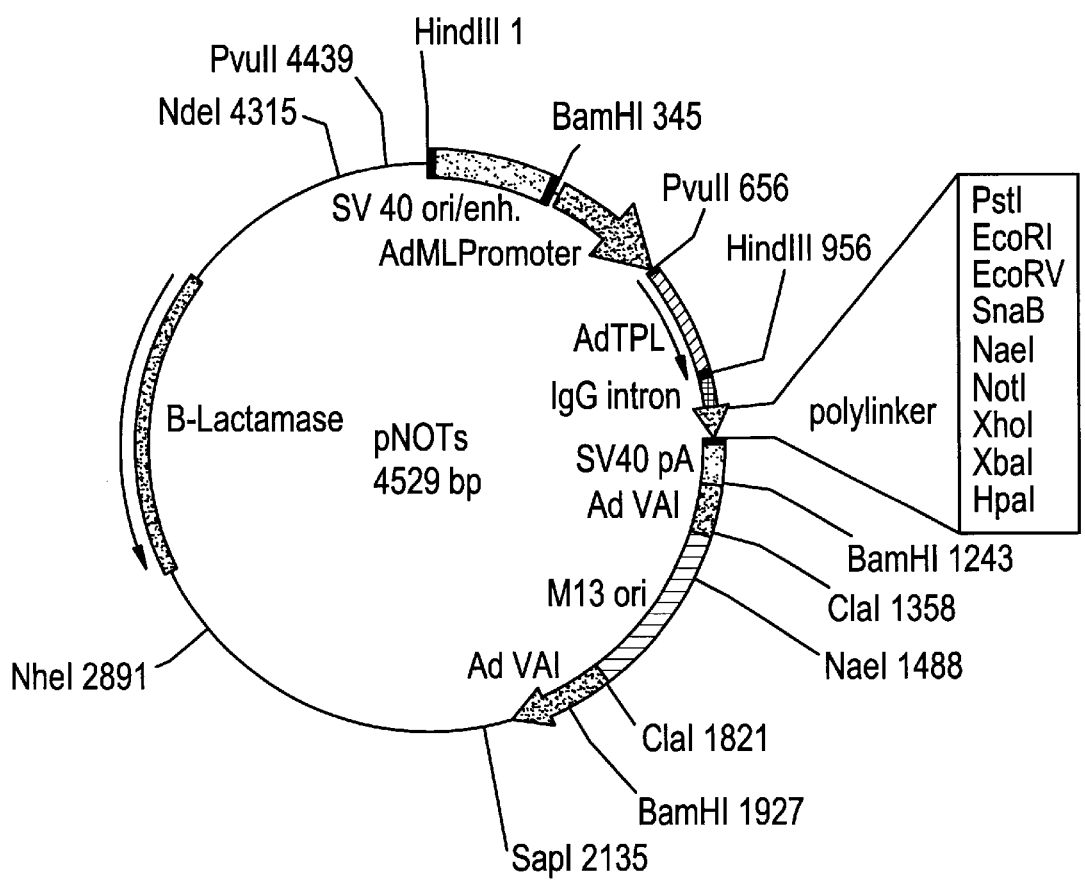

Each clone has been transfected into separate bacterial cells (*E. coli*) in this composite deposit. Each clone can be removed from the vector in which it was deposited by performing an EcoRI/NotI digestion (5' site, EcoRI; 3' site, NotI) to produce the appropriate fragment for such clone. Each clone was deposited in either the pED6 or pNOTs vector depicted in FIG. 1. The pED6dpc2 vector ("pED6") was derived from pED6dpc1 by insertion of a new polylinker to facilitate cDNA cloning (Kaufman et al., 1991, *Nucleic Acids Res.* 19: 4485–4490); the pNOTs vector was derived from pMT2 (Kaufman et al., 1989, *Mol. Cell. Biol.* 9: 946–958) by deletion of the DHFR sequences, insertion of a new polylinker, and insertion of the M13 origin of replication in the ClaI site. In some instances, the deposited clone can become "flipped" (i.e., in the reverse orientation) in the deposited isolate. In such instances, the cDNA insert can still be isolated by digestion with EcoRI and NotI. However, NotI will then produce the 5' site and EcoRI will produce the 3' site for placement of the cDNA in proper orientation for expression in a suitable vector. The cDNA may also be expressed from the vectors in which they were deposited.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of the oligonucleotide probe that was used to isolate each full-length clone is identified below, and should be most reliable in isolating the clone of interest.

| Clone | Probe Sequence |
|---|---|
| AJ26_3 | SEQ ID NO:46 |
| AJ172_2 | SEQ ID NO:47 |
| AP224_2 | SEQ ID NO:48 |
| BL89_13 | SEQ ID NO:49 |
| BL341_4 | SEQ ID NO:50 |
| BV239_3 | SEQ ID NO:51 |
| CC25_17 | SEQ ID NO:52 |
| CC397_19 | SEQ ID NO:53 |
| D305_2 | SEQ ID NO:54 |
| G55_1 | SEQ ID NO:55 |
| K39_7 | SEQ ID NO:56 |
| K330_3 | SEQ ID NO:57 |
| K363_3 | SEQ ID NO:58 |
| K446_3 | SEQ ID NO:59 |
| K464_4 | SEQ ID NO:60 |
| K483_1 | SEQ ID NO:61 |
| L69_3 | SEQ ID NO:62 |

In the sequences listed above which include an N at position 2, that position is occupied in preferred probes/primers by a biotinylated phosphoaramidite residue rather than a nucleotide (such as, for example, that produced by use of biotin phosphoramidite (1-dimethoxytrityloxy-2-(N-biotinyl-4-aminobutyl)-propyl-3-O-(2-cyanoethyl)-(N,N-diisopropyl)-phosphoramadite) (Glen Research, cat. no. 10-1953)).

The design of the oligonucleotide probe should preferably follow these parameters:

(a) It should be designed to an area of the sequence which has the fewest ambiguous bases ("N's"), if any;
(b) It should be designed to have a $T_m$ of approx. 80° C. (assuming 2° for each A or T and 4 degrees for each G or C).

The oligonucleotide should preferably be labeled with g-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 µl of the stock used to inoculate a sterile culture flask containing 25 ml of sterile L-broth containing ampicillin at 100 µg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 µg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20×stock is 175.3 g NaCl/liter, 88.2 g Na citrate/liter, adjusted to pH 7.0 with NaOH) containing 0.5% SDS, 100 µg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they may be cyclized using known methods, for example, as described in H.U. Saragovi, et al., *Bio/Technology* 10, 773–778 (1992) and in R. S. McDowell, et al., *J. Amer. Chem. Soc.* 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form of such protein may be obtained by expression of the disclosed full-length polynucleotide (preferably those deposited with ATCC) in a suitable mammalian cell or other host cell. The sequence of the mature form of the protein may also be determinable from the amino acid sequence of the full-length form.

The present invention also provides genes corresponding to the cDNA sequences disclosed herein. "Corresponding genes" are the regions of the genome that are transcribed to produce the mRNAs from which the cDNA sequences are derived and any contiguous regions of the genome necessary for the regulated expression of such genes, including but not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Proteins and protein fragments of the present invention include proteins with amino acid sequence lengths that are at least 25%(more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologs of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide, as determined by those of skill in the art. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous, or related to that encoded by the polynucleotides.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡‡ | Hybridization Temperature and Buffer† | Wash Temperature and Buffer† |
|---|---|---|---|---|
| A | DNA:DNA | ≥50 | 65° C.; 1 × SSC -or- 42° C.; 1 × SSC, 50% formamide | 65° C.; 0.3 × SSC |
| B | DNA:DNA | <50 | $T_B$*; 1 × SSC | $T_B$*; 1 × SSC |
| C | DNA:RNA | ≥50 | 67° C.; 1 × SSC -or- 45° C.; 1 × SSC, 50% formamide | 67° C.; 0.3 × SSC |
| D | DNA:RNA | <50 | $T_D$*; 1 × SSC | $T_D$*; 1 × SSC |
| E | RNA:RNA | ≥50 | 70° C.; 1 × SSC -or- 50° C.; 1 × SSC, 50% formamide | 70° C.; 0.3 × SSC |
| F | RNA:RNA | <50 | $T_F$*; 1 × SSC | $T_F$*; 1 × SSC |
| G | DNA:DNA | ≥50 | 65° C.; 4 × SSC -or- 42° C.; 4 × SSC, 50% formamide | 65° C.; 1 × SSC |
| H | DNA:DNA | <50 | $T_H$*; 4 × SSC | $T_H$*; 4 × SSC |
| I | DNA:RNA | ≥50 | 67° C.; 4 × SSC -or- 45° C.; 4 × SSC, 50% formamide | 67° C.; 1 × SSC |
| J | DNA:RNA | <50 | $T_J$*; 4 × SSC | $T_J$*; 4 × SSC |
| K | RNA:RNA | ≥50 | 70° C.; 4 × SSC -or- 50° C.; 4 × SSC, 50% formamide | 67° C.; 1 × SSC |
| L | RNA:RNA | <50 | $T_L$*; 2 × SSC | $T_L$*; 2 × SSC |
| M | DNA:DNA | ≥50 | 50° C.; 4 × SSC -or- 40° C.; 6 × SSC, 50% formamide | 50° C.; 2 × SSC |
| N | DNA:DNA | <50 | $T_N$*; 6 × SSC | $T_N$*; 6 × SSC |
| O | DNA:RNA | ≥50 | 55° C.; 4 × SSC -or- 42° C.; 6 × SSC, 50% formamide | 55° C.; 2 × SSC |
| P | DNA:RNA | <50 | Tp*; 6 × SSC | $T_P$*; 6 × SSC |
| Q | RNA:RNA | ≥50 | 60° C.; 4 × SSC -or- 45° C.; 6 × SSC, 50% formamide | 60° C.; 2 × SSC |
| R | RNA:RNA | <50 | TR*; 4 × SSC | $T_R$*; 4 × SSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†SSPE (1 × SSPE is 0.15M NaCl, 10mM $NaH_2PO_4$, and 1.25mM EDTA, pH 7.4) can be substituted for SSC (1 × SSC is 0.15M NaCl and 15mM sodium citrate) in the hybridization and wash buffers; washes are performed for 15 minutes after hybridization is complete.

-continued

| Stringency Condition | Polynucleotide Hybrid | Hybrid Length (bp)‡‡ | Hybridization Temperature and Buffer† | Wash Temperature and Buffer† |
|---|---|---|---|---|

*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C) = 2(# of A + T bases) + 4(# of G + C bases). For hybrids between 18 and 49 base pairs in length, $T_m$(° C) = 81.5 + 16.6($\log_{10}$[Na$^+$]) + 0.41(% G + C.) − (600/N), where N is the number of bases in the hybrid, and [Na$^+$] is the concentration of sodium ions in the hybridization buffer ([Na$^+$] for 1 × SSC = 0.165M).

Additional examples of stringency conditions for polynucleotide hybridization are provided in Sambrook, J., E. F. Fritsch, and T. Maniatis, 1989, *Molecular Cloning: A Laboratory Manual,* Cold Spring Harbor Laboratory Press, Cold Spring Harbor, N.Y., chapters 9 and 11, and *Current Protocols in Molecular Biology,* 1995, F. M. Ausubel et al., eds., John Wiley & Sons, Inc., sections 2.10 and 6.3–6.4, incorporated herein by reference.

Preferably, each such hybridizing polynucleotide has a length that is at least 25%(more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif. U.S.A. (the MaxBac® kit), and such methods are well known in the art, as described in Summers and Smith, *Texas Agricultural Experiment Station Bulletin* No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2 TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology.* J. E. e.a. Coligan eds. Vol 1 pp. 3.12.1–3.12.14, John Wiley and Sons, Toronto. 1994; and Measurement of mouse and human Interferon γ, Schreiber, R. D. In *Current Protocols in Immunology.* J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology.* J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. *In Current Protocols in Immunology.* J. E. e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11—Bennett, F., Giannotti, J., Clark, S. C. and Turner, K. J. In *Current Protocols in Immunology.* J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In *Current Protocols in Immunology.* J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $β_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In *Current Protocols in Immunology.* J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M.G. In *Culture of Hematopoietic Cells*. R. I. Freshney, et al. eds. Vol pp. 265–268, Wiley-Liss, Inc., New York, N.Y. 1994; Hirayama et al., Proc. Nati. Acad. Sci. USA 89:5907–5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of bums, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing*, pps. 71–112 (Maibach, H I and Rovee, D T, eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in:Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Cadherin/Tumor Invasion Suppressor Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (autoimmune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherins.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell lines with polynucleotides expressing E-cadherin has reversed cancer-associated changes by returning altered cell shapes to normal, restoring cells' adhesiveness to each other and to their substrate, decreasing the cell growth rate, and drastically reducing anchorage-independent cell growth. Thus, reintroducing E-cadherin expression reverts carcinomas to a less advanced stage. It is likely that other cadherins have the same invasion suppressor role in carcinomas derived from other tissue types. Therefore, proteins of the present invention with cadherin activity, and polynucleotides of the present invention encoding such proteins, can be used to treat cancer. Introducing such proteins or polynucleotides into cancer cells can reduce or eliminate the cancerous changes observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and polynucleotides of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and polynucleotides of the present invention encoding such proteins, can used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and polynucleotides of the present invention encoding such protein fragments, can also be used to block cadherin function by binding to cadherins and preventing them from binding in ways that produce undesirable effects. Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63: 1033–1038, 1990.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 ng to about 10 mg, more preferably about 0.1 $\mu$g to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al, FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

EXAMPLE 1

Characterization of AJ172_2 DNA and Protein

AJ172_2, a novel human cDNA isolated using a yeast signal sequence trap, encodes a protein that exhibits significant homology to a baboon endogenous retrovirus envelope protein. Genomic DNA sequences flanking the AJ172_2 gene reveal that it is part of a previously uncharacterized defective provirus, indicating that the sequence may be an example of a retroviral gene that has been "captured" by the human host. Southern blot analyses show that AJ172_2-hybridizing sequences are restricted to humans and monkeys; being absent from cows, dogs, rats, mice, rabbits, chickens and yeast. Northern blot analyses demonstrate that although the AJ172_2 gene is very highly transcribed in the human placenta and weakly transcribed in the testes, it is not expressed at all in 21 additional human tissues. In situ antisense RNA hybridizations performed on full-term human placental sections revealed that AJ172_2 transcripts are specifically localized to villous syncytiotrophoblasts, a fused, multinucleated cell type derived from fetal trophoblast tissue. We find that AJ172_2 expression in COS cells reproducibly causes the formation of giant multinucleated COS-cell syncytia which closely resemble these fused placental syncytiotrophoblasts, suggesting that AJ172_2 plays a role in mediating cell fusion events in human placenta and fusion of other types of cells expressing AJ172_2. A number of independent binary reporter gene approaches indicate that AJ172_2-induced COS syncytia are truly derived from cell-cell fusions and do not result from incomplete cell divisions. AJ172_2 can mediate fusion of many different cell types, including human, monkey, rodent and insect lines. Moreover even simple liposomes can fuse readily to AJ172_2-transfected COS cells, suggesting that AJ172_2 requires neither homophilic nor heterophilic protein-protein interactions to promote membrane fusion events.

We have also found that co-transfection of AJ172_2 with IL-11 or IL-12 into COS cells reproducibly leads to 2–5 fold increases in secreted cytokine yields. This phenomenon can be used in applications for AJ172_2 in enhancing mammalian cell recombinant gene expression.

The full-length AJ172_2 cDNA encodes a typical signal sequence, an extracellular domain, a transmembrane domain and a short cytoplasmic tail. The recent appearance in public databases of many very closely related EST sequences derived from many independent cDNA libraries provides additional supporting evidence for the expression of AJ172_2 in vivo. We also find that the DNA sequence of a segment of human chromosome 7 (genbank accession #AC000064) carries the entire AJ172_2 sequence. A closer examination of this chromosomal segment reveals the presence of a complete, previously uncharacterized, defective retrovirus. This provirus exhibits a typical morphology; 5' and 3'-long terminal repeat sequences, putative gag and pol genes, and a third open reading frame encoding a putative viral envelope protein. The gag and pol genes are punctuated by multiple chain termination codons and are defective, whereas the third, envelope ORF is intact. This third ORF is identical to AJ172_2, which we conclude to be the envelope gene of an ancient retrovirus.

We have demonstrated that AJ172_2 is expressed highly and very specifically in human placental syncytiotrophoblasts. By means of in vitro transfection experiments we go on to show that AJ172_2, like many previously described viral envelope proteins, can mediate cell to cell fusion events leading to the formation of giant syncytia. In a series of further experiments we demonstrate that neither homophilic nor heterophilic protein-protein interactions are required for AJ172_2 function, indeed the molecule can mediate efficient cell fusion to simple liposomes. We suspect that AJ172_2 may play a critical role in the normal placental biology of humans and primates, mediating cell fusion events which may be important in processes such as blastocyst implantation, the control of uterine wall infiltration by fetal trophoblasts, and in optimizing the efficiency of placental transporter and secretory function. AJ172_2 may thus be the first described example of a captured viral gene performing an important biological role in a mammalian host organism.

Figure 2:
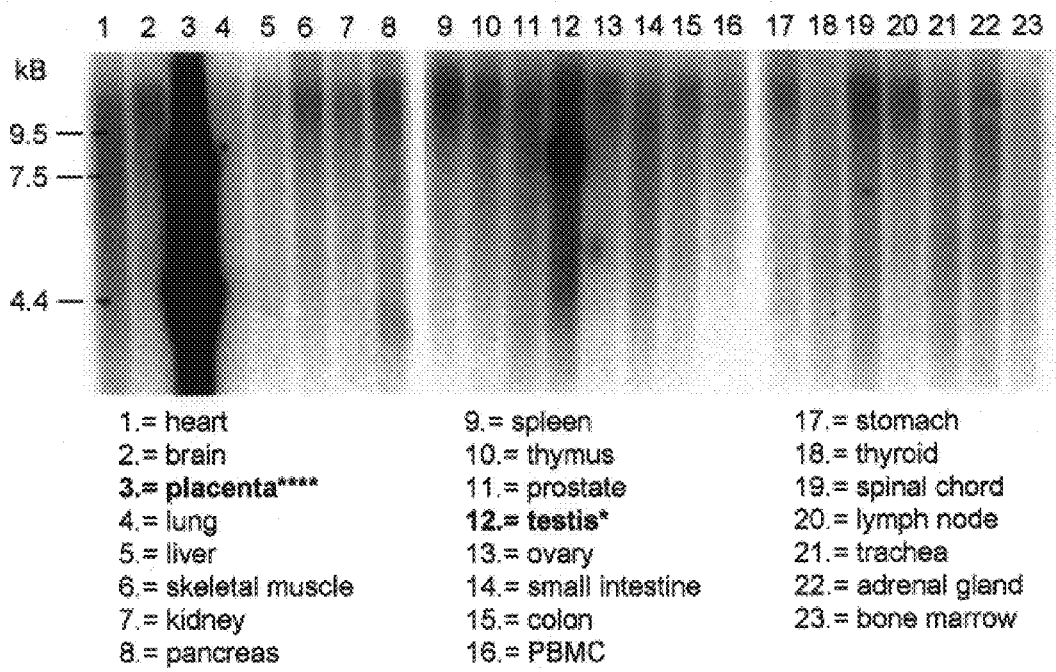
FIG. 2 presents the results of Northern analyses of multiple human tissues which indicate that AJ172_2 is expressed highly in the placenta and weakly in the testes.

FIG. 2 presents the results of Northern analyses of multiple human tissues which indicate that AJ172_2 is expressed highly in the placenta and weakly in the testes.

Figure 3:
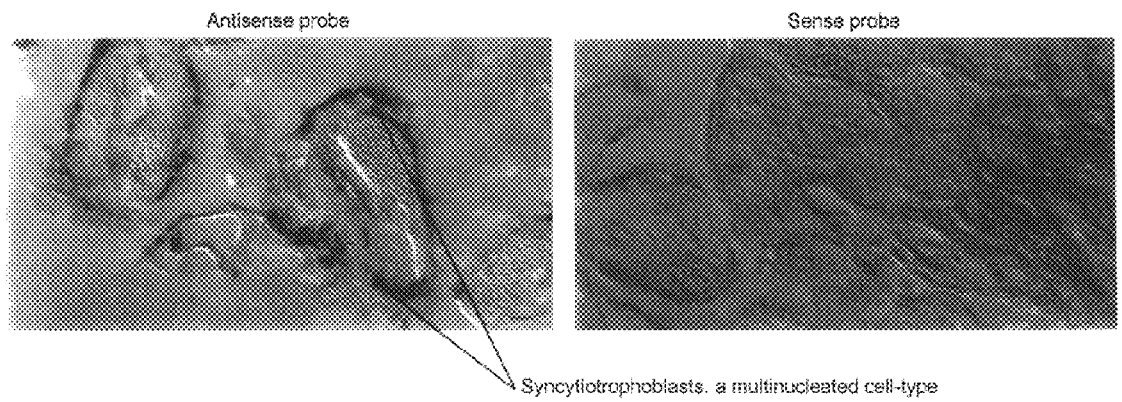
FIG. 3 presents the results of in situ antisense-RNA hybridizations which localize AJ172_2 expression to placental syncytiotrophoblasts.

As shown in FIG. 3, in situ antisense-RNA hybridizations were used to specifically localize AJ172_2 expression to placental syncytiotrophoblasts.

Figure 4:
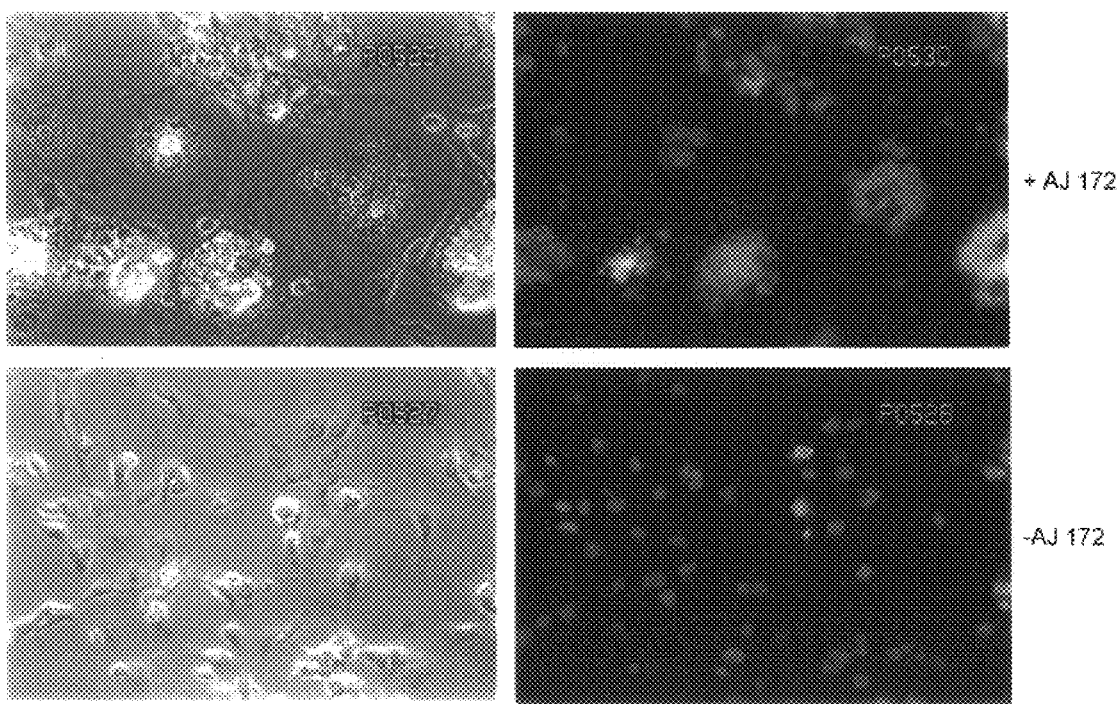
FIG. 4 demonstrates that AJ172_2 expression in transfected COS cells can cause the formation of giant multinucleated syncytia by a fusigenic mechanism. The cells expressing AJ172_2 can be seen to have formed multinucleate syncytia, while the non-transfected cells remained mononucleate.

FIG. 4 demonstrates that AJ172_2 expression in transfected COS cells can cause the formation of giant multinucleated syncytia by a fusigenic mechanism. The cells expressing AJ172_2 can be seen to have formed multinucleate syncytia, while the non-transfected cells remained mononucleate.

Figure 5:
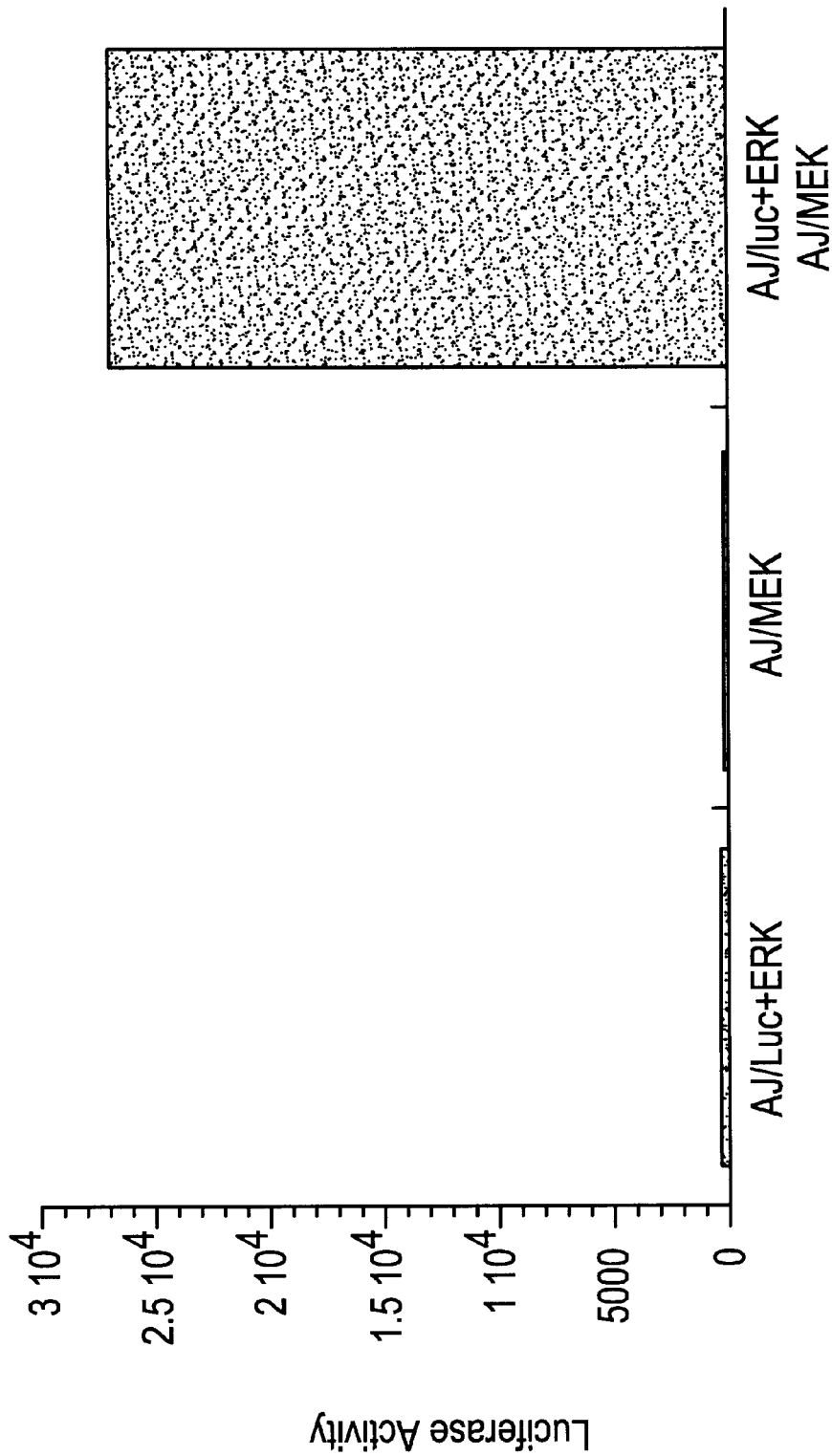
FIG. 5 demonstrates that AJ172_2 mediates actual cell fusion and does not operate through a mechanism of arrested cell division. A first cell line was transfected with AJ172 2, luciferase and ERK. A second cell line was transfected with AJ172_2 and MEK. When the cells were mixed, fusion occurred resulting in production of luciferase activity.

FIG. 5 demonstrates that AJ172_2 mediates actual cell fusion and does not operate through a mechanism of arrested cell division. A first cell line was transfected with AJ172_2, luciferase and ERK. A second cell line was transfected with AJ172_2 and MEK. When the cells were mixed, fusion occurred resulting in production of luciferase activity.

FIG. 6 demonstrates that AJ172_2 can mediate fusion between cells of differing types and between a cell expressing AJ172_2 and a cell not expressing AJ172_2. HELA cells were transfected with a cDNA encoding a P-selectin glycoprotein ligand-1/Fc fusion protein (PSGL-Fc). COS cells were transfected with AJ172_2. Another batch of COS cells was transfected with AJ172_2 in reverse orientation. The transfected HELA cells were mixed with each type of COS cells. As shown in FIG. 6, mixture with the AJ172_ transfected COS cells caused fusion with the HELA cells, resulting in multinucleate fusions. Mixture with the COS cells transfected with AJ172_2 in reverse orientation resulted in no fusion (mononucleate cells remained).

Figure 7:
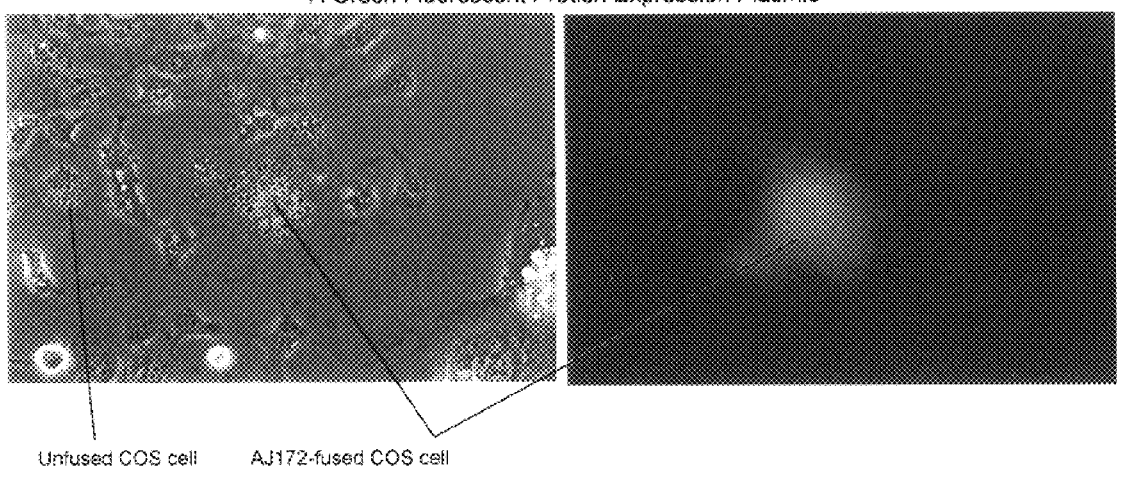
FIG. 7 demonstrates that the mechanism of AJ172_2 induced cell fusion does not require homophilic or heterophilic protein-protein interactions. COS cells transfected with AJ172_2 were mixed with liposomes containing a green fluorescent protein (GFP) expression plasmid.

FIG. 7 demonstrates that the mechanism of AJ172_2 induced cell fusion does not require homophilic or heterophilic protein-protein interactions. COS cells transfected with AJ172_2 were mixed with liposomes containing a green fluorescent protein (GFP) expression plasmid. As shown in FIG. 7, the COS cells fused with the liposomes, took up the expression plasmid, and began expressing GFP.

Cell fusion in the human placenta has been implicated in a number of critical processes. Early in human placental development, embryonic trophoblastic cells are thought to fuse with epithelial cells during blastocyst implantation into the uterine wall. Subsequently, the carefully orchestrated invasion of fetal cytotrophoblast through the maternal decidua into the endometrium is perhaps controlled by cell fusion events, since invasive cytotrophoblasts become non-invasive when they fuse to form multinucleated syncytiotrophoblasts. Choriocarcinomas arise when cytotrophoblast fusion fails to occur and the invasive process continues unabated. Finally syncytiotrophoblasts found in the placental villi form a continuous boundary layer between maternal and fetal tissue. This vitally important structure is responsible for the efficient transfer to the fetus of nutrients, growth factors and antibodies, and for the removal of waste products. It is possible that cytotrophoblast cell fusion is an adaptation to increase the efficiency of these transport and secretory processes.

In 1991 Harris proposed that the invasiveness of the fetal trophoblast was a trait acquired by a mammalian antecedent following an ancient retroviral infection. He went on to suggest that this event may even have been seminal in the evolution of all modern placental mammals. Harris based his hypothesis on circumstantial evidence, namely the frequent observation of retrovirus-like particles in placental preparations, and the presence in placenta of fused cells with a morphology reminiscent of retrovirally-induced syncytia. The ability of AJ172_2 to mediate cell fusion events, its highly specific pattern of expression in placental syncytiotrophoblasts, and its presence in the genome as a part of a cryptic provirus all tend to support Harris's view. AJ172_2 may be the first example of a viral gene co-opted to serve a vital role in a mammalian host.

Although other mammalian placentas possess fused cell types, to date we have found AJ172_2-related sequences only in human and primate genomes. The simplest explanation for this would be that the protypical AJ172_2-like sequence has diverged extensively during the course of mammalian evolution. An alternative explanation would be that sequestration of a retrovirus to perform a role in placental development was a relatively common evolutionary event, and that the antecedents of different mammalian lineages simply used different retroviruses to achieve the same goal. The fact that AJ172_2 needs no other receptor protein to function, the common ability of many known viruses to mediate cell-cell fusions, and the great diversity observed in placental morphology even among closely related mammalian species would all be consistent with this explanation. Notwithstanding this, it is also possible that early primates acquired the AJ172_2 provirus for some unknown, primate-specific reason.

Trophoblast syncytia may make a number of important contributions to overall placental efficiency. One of these may simply be to provide an extended surface area for maternal/fetal exchange. In this regard the theoretical geometry of syncytia formation predicts that the ratio of overall cell surface area to cytoplasmic volume will decrease progressively as cells fuse together. If overall cytoplasmic volume and cell surface area remain constant during cell fusion, then the growing syncytium will progressively accumulate "excess" cell membrane over and above that which is required simply to enclose the cytoplasmic contents. This extra membrane should enable the syncytium to "spread" and cover a larger area of the substratum than would the equivalent number of unfused cells. Thus in the placenta the formation of syncytia would tend to increase placental efficiency by enlarging the area of the exchange surface. In support of this theoretical prediction we have observed in vitro that COS cells fused as a result of AJ172_2 expression adopt a "fried egg" appearance, with the nuclei gathered tightly together in one location and the cytoplasm covering an extended surface area.

Antagonists to AJ172_2 (either antibodies, antibody fragments, nucleotide aptamers, peptide aptamers, antisense nucleotides or small molecules) may be useful as birth control agents, either by preventing initial implantation of embryos into the uterine wall or by interrupting normal placental development and leading to abortion of the conceptus.

Since the regulation of AJ172_2 expression is very tight, small molecules designed to positively or negatively modulate the control of AJ172_2 gene expression may be useful as birth control agents. They may also be useful in treatment of placental pathologies such as pre-eclampsia or choriocarcinoma, where aberrant cytotrophoblast fusion events have been observed.

AJ172_2 as a cell fusion agent may have applications as a means of increasing DNA transfection efficiencies in vitro (research applications, moving genes into cultured cell lines or primary cell lines with greater efficiency) or in vivo (gene therapy applications, moving genes into cells in the intact organism with greater efficiency).

AJ172_2 may also be implicated in osteoclast fusion. Therefore, AJ172_2 antagonists or small molecules directed to control of AJ172_2 gene expression may be useful in the treatment of bone disorders such as osteoporosis or osteopetrosis.

EXAMPLE 2

Additional Evidence for AJ172 Expression in Choriocarcinoma Lines

Figure 8:
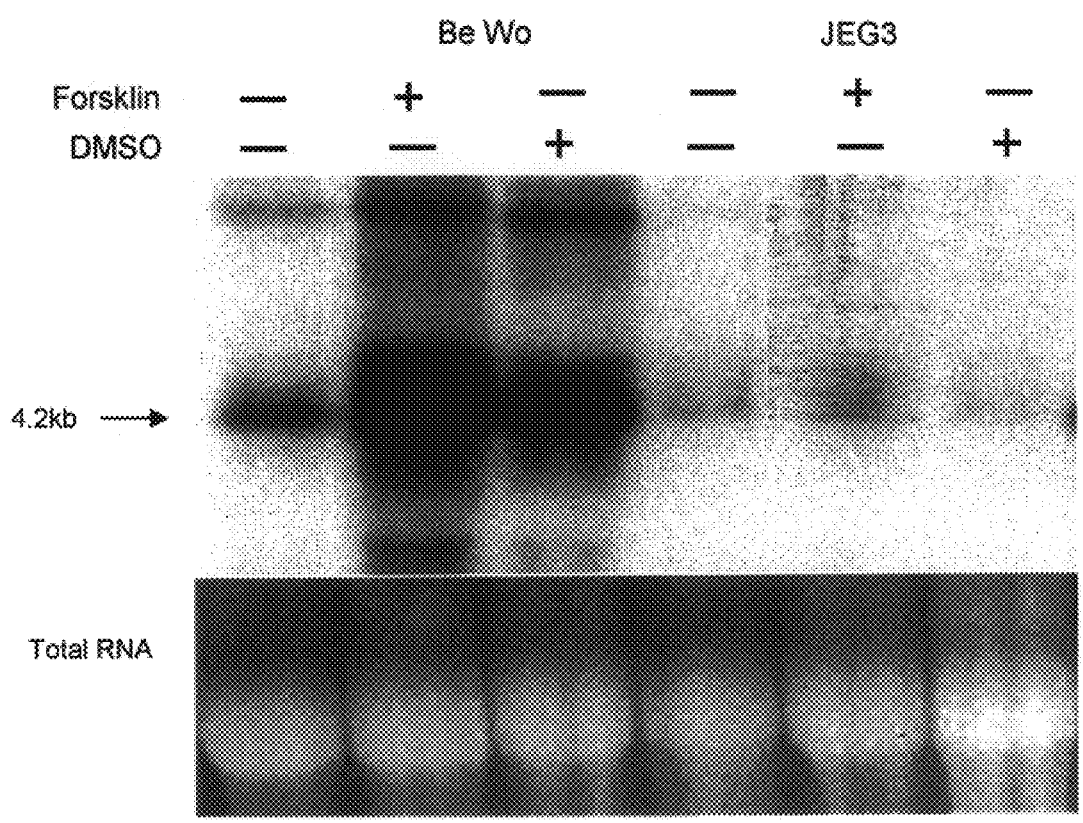
FIGS. 8–10 present data which demonstrate that AJ172_2 is expressed in the formation of cytotrophoblasts associated with choriocarcinoma (see Example 2).
Figure 9:
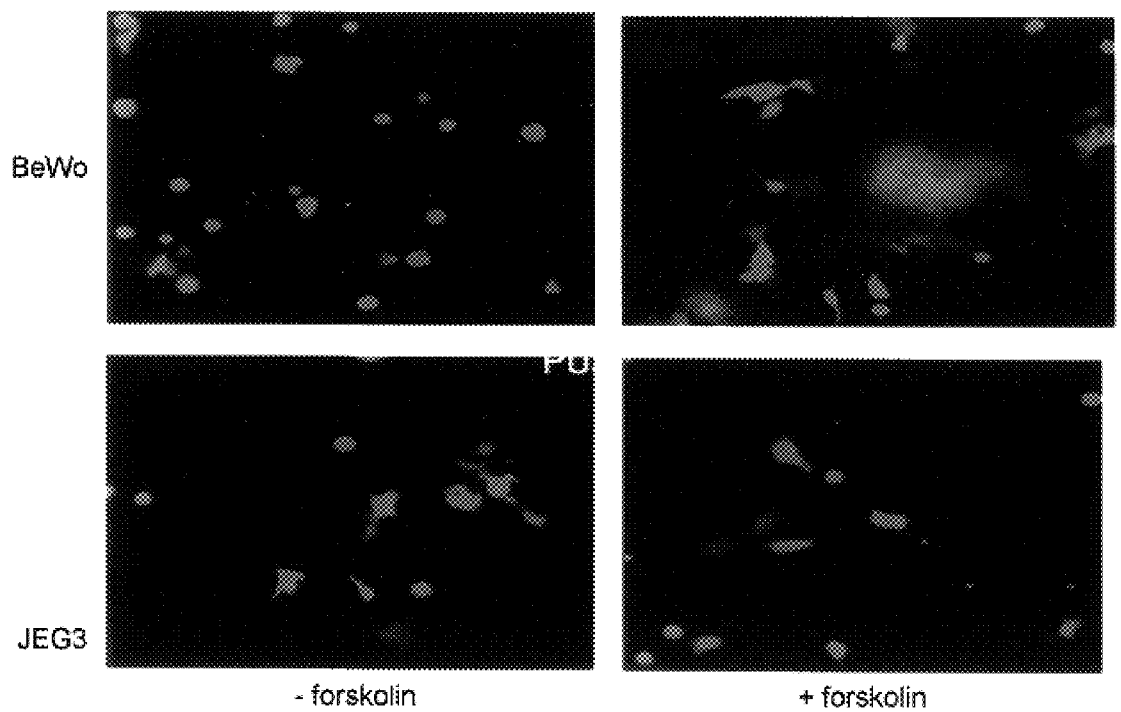
Figure 10:
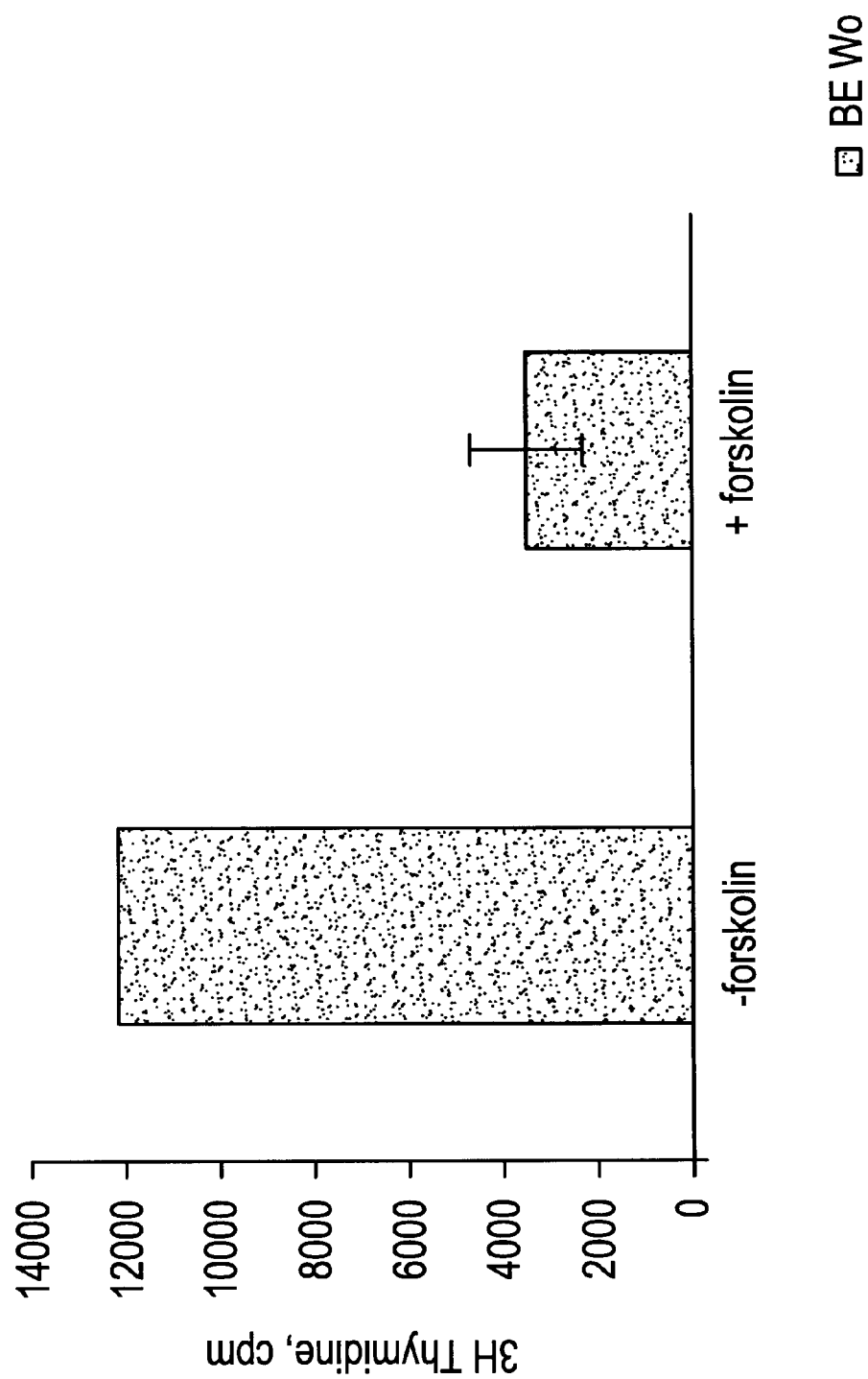

Although the above experiments demonstrate that AJ172_2 can induce cell fusion, to establish that AJ172_2 expression could be correlated with cytotrophoblast fusion, we examined in vitro the fusion of BeWo cells, and monitored levels of AJ172_2 transcription in response to forskolin treatment. BeWo is a human trophoblastic choriocarcinoma line which can be induced by forskolin to form syncytiotrophblasts. (BeWo-derived syncytiotrophblasts are morpologically very similar to AJ172_2-fused COS cells). FIG. 8 shows that AJ172_2 transcription in BeWo cells increases at least five fold in response to forskolin treatment, correlating well with cell fusion (FIG. 9). In contrast a control choriocarcinoma line which fails to fuse in response to forskolin, JEG3, showed no expression of AJ172_2. Taken together these results establish that AJ172_2 can indeed mediate cell fusion in a trophoblastic cell type. Moreover DNA synthesis is arrested in BeWo cells which have been treated with forskolin (FIG. 10), perhaps as a result of AJ172 expression and induction of cell fusion. Thus induction of AJ172 synthesis in vivo may be a therapy useful for controlling the growth of choricarcinomas.

EXAMPLE 3

Additional Evidence for AJ172 Disregulation in Pre-eclampsia

Figure 12:
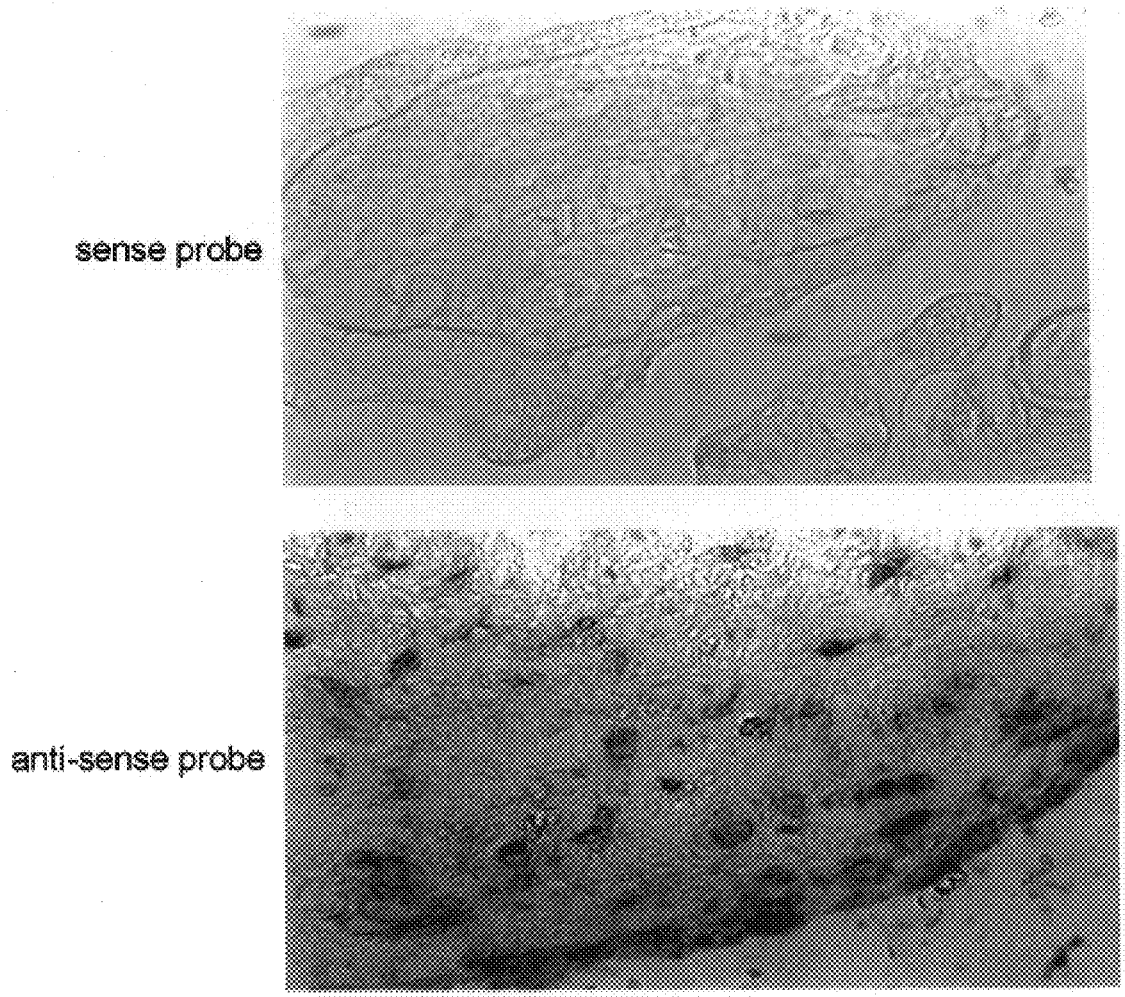

We performed in situ hybridizations on tissue sections prepared from the villous region of human pre-eclamptic placenta to examine if there were differences in the distribution of AJ172 expression compared to normal placenta. In the normal situation hybridization of a digoxygenin-labelled antisense AJ172_2 RNA probe is observed only to syncytiotrophoblasts comprising the layer of fused cells on the edges of the villi, bordering on the maternal blood space (FIG. 11). In contrast for pre-eclamptic samples hybridization was observed in patches of fused cells throughout the placental villi (FIG. 12). Thus it appears that AJ172 expression is disregulated in pre-eclampsia. This would indicate that pre-eclamsia and other diseases of placental morphogenesis may be caused by temporal or spatial disregulation of AJ172 expression, quantitative disregulation in AJ172 expression levels, or by mutations in the AJ172 gene.

In addition to uses and therapies discussed above, antibodies to AJ172 are useful in detecting serum levels of AJ172, and thus are useful as a dignostic tools to monitor for pre-eclampsia, for other placental pathologies or for cancerous conditions. Agents modulating AJ172 expression or function have therapeutic potential in treatment of neoplastic diseases in addition to choriocarcinoma.

EXAMPLE 4

Figure 13:
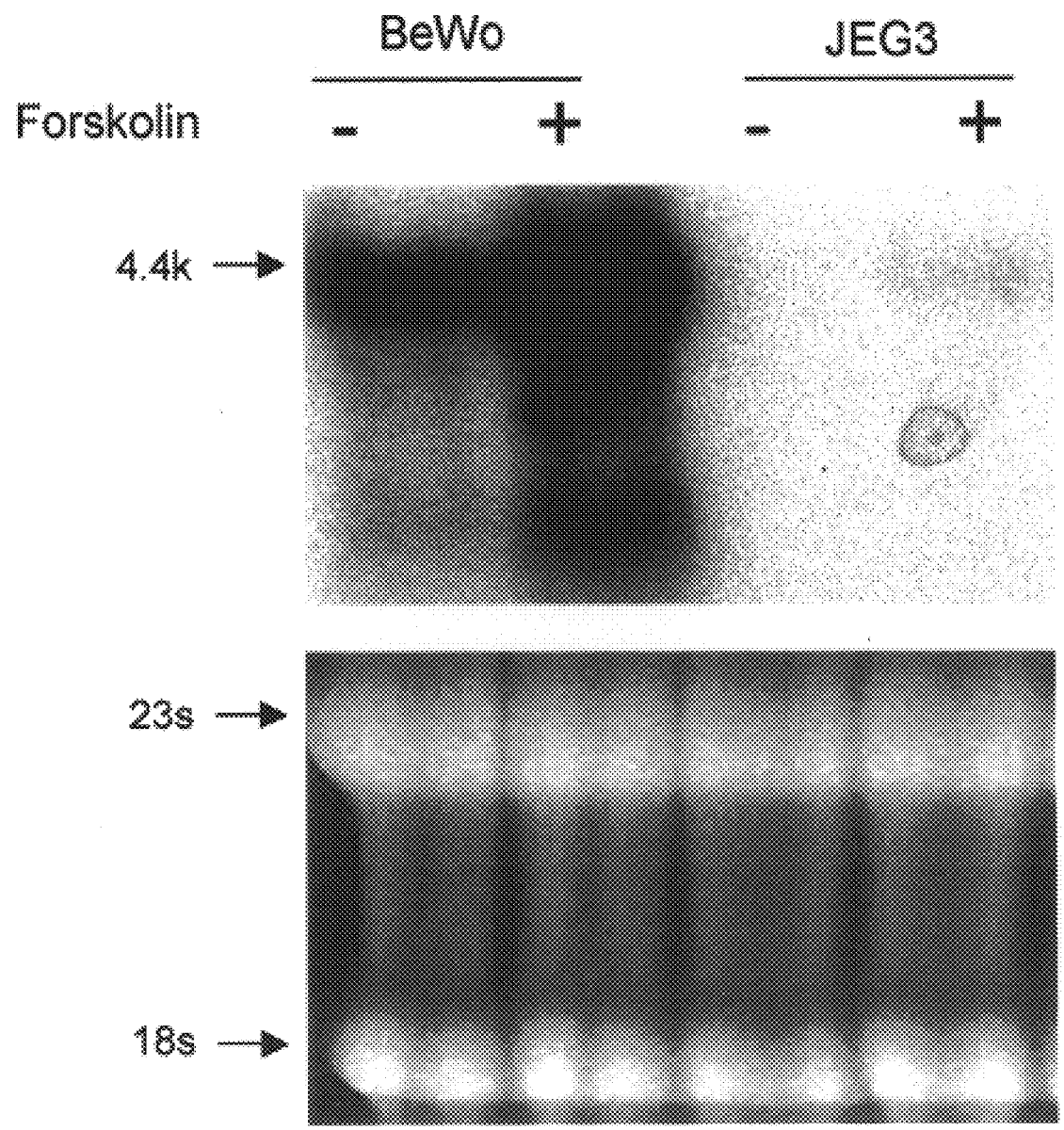

Additional Data Supporting a Role for AJ172 in Tissue Remodelling and Extracellular Matrix Degradation We have observed that in BeWo choriocarcinoma cells, following treatments with forskolin and resulting in induction of both AJ172 and cell fusion, an increase in collagenase A expression at the RNA (FIG. 13) and protein levels (FIG. 14). These changes in expression may reflect the normal course of events in placenta, where it is known that a large amount of extracellular matrix remodelling occurs during placental morphogenesis. We see similar changes in COS cells transfected with AJ172, leading to the conclusion that changes in collagenase A expression levels may be a general cellular response to the cell fusion process. It is further possible that disregulated AJ172 expression, leading to increased local extracellular matrix breakdown, could be a contributing factor to metastatic processes in certain tumors. Thus, correction of this disregulation using AJ172 DNA, protein and/or antibodies would inhibit such breakdown and the resulting metastases.

Patent and literature references cited herein are incorporated by reference as if fully set forth.

What is claimed is:

1. An isolated polynucleotide which comprises the nucleotide sequence of the full-length protein coding sequence of clone AJ172_2 deposited under accession number ATCC 98115, wherein said polynucleotide is no greater than 3000 nucleotides in length.

2. An isolated polynucleotide which encodes the full-length protein encoded by the cDNA insert of clone AJ172_2 deposited under accession number ATCC 98115, wherein said polynucleotide is no greater than 3000 nucleotides in length.

3. An isolated polynucleotide which comprises the nucleotide sequence of the mature protein coding sequence of clone AJ172_2 deposited under accession number ATCC 98115, wherein said polynucleotide is no greater than 3000 nucleotides in length.

4. An isolated polynucleotide which encodes the mature protein encoded by the cDNA insert of clone AJ172_2 deposited under accession number ATCC 98115, wherein said polynucleotide is no greater than 3000 nucleotides in length.

5. An isolated polynucleotide which encodes a protein comprising the amino acid sequence of SEQ ID NO:4, wherein said polynucleotide is no greater than 3000 nucleotides in length.

6. An isolated polynucleotide of no greater than 3000 nucleotides in length that hybridizes under conditions of 4×SSC at 65 degrees Celsius followed by washing at 65 degrees Celsius in 1×SSC to a complement DNA of the polynucleotide having the nucleotide sequence of SEQ ID NO:3, said polynucleotide encoding a protein which is at least 75% the length of the protein of SEQ ID NO:4 and which mediates cell to cell fusion.

7. An isolated polynucleotide no greater than 3000 nucleotides in length which encodes a protein having an amino acid sequence at least 90% identical to the amino acid sequence set forth as SEQ ID NO:4, wherein said protein mediates cell to cell fusion.

8. An isolated polynucleotide no greater than 3000 nucleotides in length which encodes a protein comprising a fragment of the amino acid sequence of SEQ ID NO:4, said fragment mediating cell to cell fusion.

9. The polynucleotide of claim 8 which comprises the nucleotide sequence of SEQ ID NO:3, from nucleotide 928 to nucleotide 2541.

10. The polynucleotide of claim 8 which comprises the nucleotide sequence of SEQ ID NO:3 from nucleotide 988 to nucleotide 2541.

11. The polynucleotide of claim 8 which comprises the nucleotide sequence of SEQ ID NO:3 from nucleotide 684 to nucleotide 1128.

12. An isolated polynucleotide which comprises the nucleotide sequence of SEQ ID NO:3, wherein said polynucleotide is no greater than 3000 nucleotides in length.

13. The isolated polynucleotide of any one of claims 12 and 1–7 wherein said polynucleotide is operably linked to an expression control sequence.

14. A host cell transformed with the isolated polynucleotide of any one of claims 12 and 1–7, wherein said polynucleotide is operably linked to at least one expression control sequence.

15. A mammalian host cell transformed with the isolated polynucleotide of any one of claims 12 and 1–7, wherein said polynucleotide is operably linked to at least one expression control sequence.

16. A process for producing a protein encoded by the polynucleotide of any one of claims 12 and 1–7, which process comprises:
   (a) growing a culture of a host cell transformed with the polynucleotide of any one of claims 12 and 1–7, wherein said polynucleotide is operably linked to at least one expression control sequence in a suitable culture medium; and
   (b) purifying said protein from the culture.

\* \* \* \* \*